(12) United States Patent
Miron

(10) Patent No.: US 9,784,674 B2
(45) Date of Patent: Oct. 10, 2017

(54) ANALYTES MONITORING BY DIFFERENTIAL SWEPT WAVELENGTH ABSORPTION SPECTROSCOPY METHODS

(71) Applicant: NGP Inc, Pierrefonds (CA)

(72) Inventor: Nicolae Miron, Pierrefonds (CA)

(*) Notice: Subject to any disclaimer, the term of this patent is extended or adjusted under 35 U.S.C. 154(b) by 83 days.

(21) Appl. No.: 14/860,089

(22) Filed: Sep. 21, 2015

(65) Prior Publication Data

US 2016/0084757 A1 Mar. 24, 2016

Related U.S. Application Data

(60) Provisional application No. 62/071,312, filed on Sep. 22, 2014.

(51) Int. Cl.
| | | |
|---|---|---|
| *G01N 21/00* | (2006.01) | |
| *G01N 21/39* | (2006.01) | |
| *G01J 3/42* | (2006.01) | |
| *G01N 21/03* | (2006.01) | |
| *G01J 3/10* | (2006.01) | |
| *G01N 21/05* | (2006.01) | |

(52) U.S. Cl.
CPC ............... *G01N 21/39* (2013.01); *G01J 3/10* (2013.01); *G01J 3/42* (2013.01); *G01N 21/031* (2013.01); *G01J 2003/423* (2013.01); *G01N 21/05* (2013.01); *G01N 2021/399* (2013.01)

(58) Field of Classification Search
CPC ........ G01N 21/61; G01N 21/31; G01N 21/39; G01N 33/00; G01N 21/88; G01N 21/59; G01N 21/17; G01N 30/02; G01N 21/031; G01N 21/3504; G01N 21/00; G01N 21/35; G01B 9/02; G01J 3/02; G01J 3/4338; G01J 3/433

See application file for complete search history.

(56) References Cited

U.S. PATENT DOCUMENTS

| | | | | |
|---|---|---|---|---|
| 5,973,782 | A * | 10/1999 | Bomse | G01J 3/4338 356/451 |
| 6,040,914 | A * | 3/2000 | Bortz | G01J 3/433 250/345 |
| 2006/0044562 | A1* | 3/2006 | Hagene | G01N 21/39 356/437 |
| 2006/0119851 | A1* | 6/2006 | Bounaix | G01N 21/031 356/437 |
| 2008/0198027 | A1* | 8/2008 | Bugge | G01N 21/3504 340/632 |
| 2012/0287418 | A1* | 11/2012 | Scherer | G01N 21/61 356/51 |
| 2014/0192343 | A1* | 7/2014 | Harrison | G01J 3/02 356/51 |
| 2015/0177131 | A1* | 6/2015 | Liu | G01N 21/39 356/326 |

* cited by examiner

*Primary Examiner* — Jamil Ahmed
(74) *Attorney, Agent, or Firm* — Eugene Gierczak; Miller Thomson LLP

(57) ABSTRACT

The present invention relates to a method, apparatus and system for measuring the content of either one or more gas analytes that may be part of a gas. The present invention applies a spectroscopic method that utilizes an extremely narrow linewidth laser beam that is absorbed when its wavelength is swept across the interval containing the absorption line of the analyte. The method, apparatus and system of the present invention is applicable to any analyte in gas phase that is part of a gas mixture, or to any analyte in a plasma phase, as well as analytes in other environments.

20 Claims, 22 Drawing Sheets

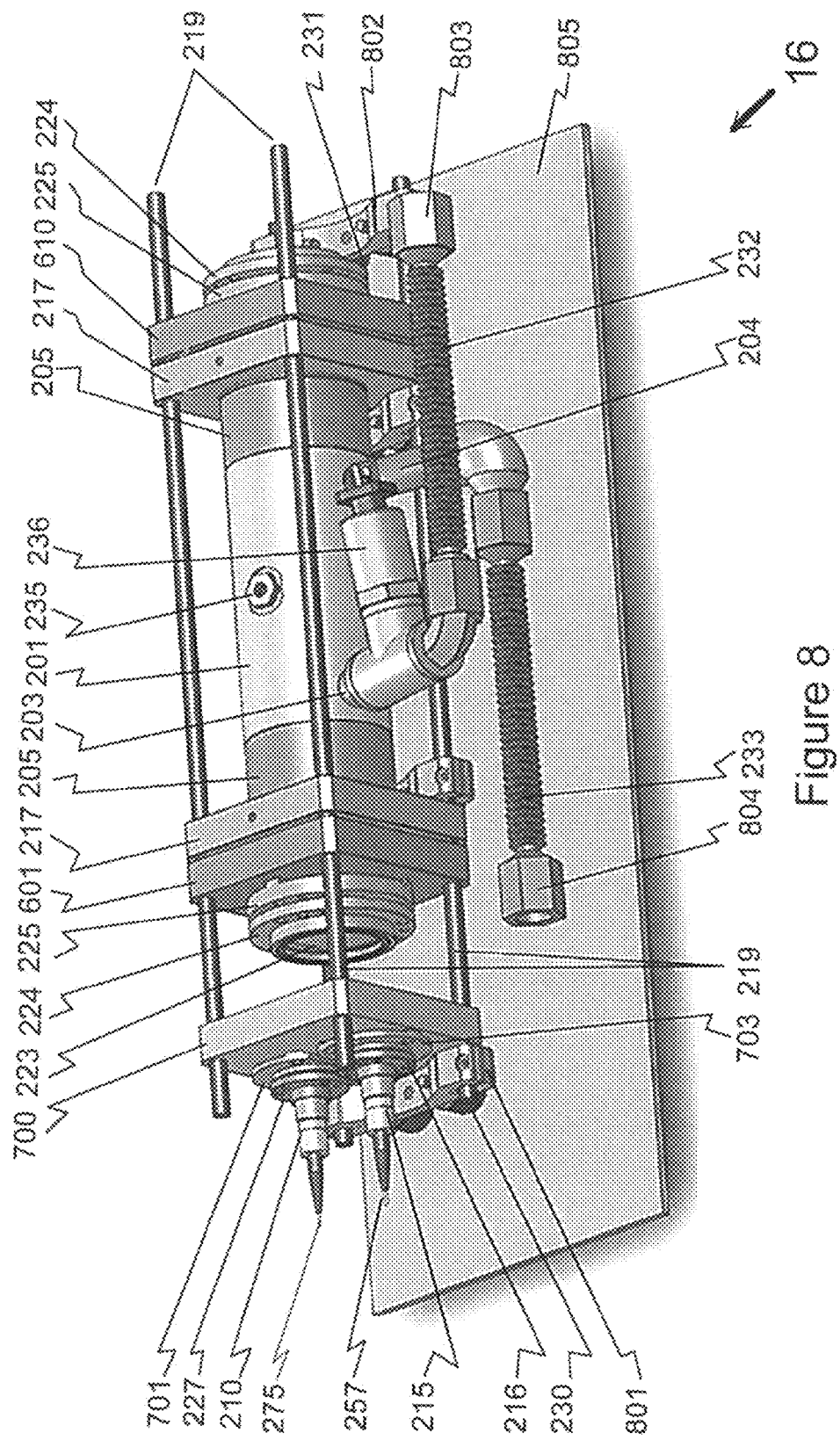

ANALYTES MONITORING BY DIFFERENTIAL SWEPT WAVELENGTH ABSORPTION SPECTROSCOPY METHODS

This application claims the benefit of U.S. Provisional Patent Application Ser. No. 62/071,312 filed Sep. 22, 2014.

FIELD OF INVENTION

This invention relates in general to the field of analyte detection and more particularly to quantitative measurement of one or more analytes for commercial and space station applications.

BACKGROUND OF THE INVENTION

Industries such as natural gas, oil, thermoelectric power plants, chemistry, pharmaceutics, medicine and other industries face many situations when the following activities are critical: detection of the presence of one or more analytes; and quantitative measurement of one or more analytes. Space exploration requires also accurate and reliable instrumentation for measuring the concentration of various analytes such as methane (CH4), water (H2O), carbon monoxide (CO) and other analytes. There are several known methods for detecting analytes, including those discussed herein.

Some known methods of detection and quantitative measurement of one or more analytes involve resonant absorption by the analyte of a very narrow band laser beam. Such methods are preferred over other methods due to the high selectivity, sensitivity, accuracy and reliability that such methods achieve. For example, tunable diode laser absorption spectroscopy ("TDLAS") is used extensively and is spreading progressively in spectroscopic analytical instrumentation (see: C. R. Webster, S. P. Sander, R. Beer, R. D. May, R. G. Knollenberg, D. M. Hunten, J. B.; "Tunable diode laser IR spectrometer for in situ measurements of the gas phase composition and particle size distribution of Titan's atmosphere", *Appl. Opt.*, 29, 7, (1990), pp. 907-917). In methods of TDLAS, the narrow band output beam generated by a tunable distributed feedback Bragg grating ("DFB") laser is scanned across a spectral interval containing the preferred absorption line of the analyte. The absorption detection within the scanning interval indicates the existence of the analyte. The amount of absorption is dependent on the analyte concentration within the measuring volume.

One known method of TDLAS is harmonic spectroscopy, whereby the bias current of the DFB laser is modulated simultaneously with small amplitude, high frequency sine wave signal with frequency f, overlapped on low frequency sawtooth signal (see: Silver J. A; "Frequency-modulation spectroscopy for trace species detection: theory and comparison among experimental methods"; *Appl. Opt.* 31, 6, pp. 707-717; U.S. Pat. No. 7,339,168 issued 2008 Mar. 4 to Spectrasensors, Inc.; U.S. Pat. No. 6,657,198 issued 2003 Dec. 2 to Spectrasensors, Inc.; U.S. Pat. No. 7,132,661 issued 2006 Nov. 7 to Spectrasensors, Inc.; U.S. Pat. No. 8,547,554 issued 2013 Oct. 1 to General Electric Company). This method is known as 2f harmonic wavelength modulated spectroscopy ("WMS-2f"). The second harmonic (2f) component of the modulated laser beam has a peak coincident with the absorption peak of the analyte and has also two adjacent dips. The absorption by the analyte is proportional with the difference in amplitude between the peak and one adjacent dip, which is a floating reference. The analyte concentration is a function of this difference. The function coefficients are defined during calibration.

Harmonic spectroscopy has several disadvantages, including the following: (i) it involves a floating reference that introduces measurement uncertainty at low analyte concentration; (ii) widening the absorption linewidth during signal processing as is involved in harmonic spectroscopy results in overlapping narrowly spaced peaks; (iii) it does not offer any possibility for measuring the baseline, or limiting the detection of low analyte concentrations; and (iv) it does not offer any means of minimizing the influence of inherent laser power changes during the wavelength tuning by direct measurement. U.S. Pat. No. 7,586,094 issued 2009 Sep. 8 to Spectrasensors, Inc., claims baseline computation by extrapolation of measured absorption values beyond the two sides of the absorption peak. WMS-2f has non-linear changes with temperature, pressure, coexisting gas components and the like (see: U.S. Patent Application Publication No. 2013/0135619 filed 2012 Nov. 28 naming assignee Yokogawa Electric Corporation). The minimum detectable analyte concentrations are reported in the range of 10 ppb (see: Silver J. A; "Frequency-modulation spectroscopy for trace species detection: theory and comparison among experimental methods"; *Appl. Opt.* 31, 6, pp. 707-717).

Another known method is the spectrum area method, which considers the analyte concentration function of the area delimited by the shape of the absorption line of the analyte (see: U.S. Patent Application Publication No. 2013/0135619 filed 2012 Nov. 28 naming assignee Yokogawa Electric Corporation; U.S. Pat. No. 8,482,735 issued 2013 Jul. 9 to Yokogawa Electric Corporation; U.S. Patent Application Publication No. 2013/0021612 filed 2012 Jul. 20 naming assignee Yokogawa Electric Corporation). According to the inventions disclosed in U.S. Pat. No. 8,482,735 and U.S. Patent Application Publication Nos 2013/0135619 and 2013/0221612, the spectrum area changes linearly with the pressure changes and does not depend on temperature and on coexisting gases. A calibration is required for finding the dependence of analyte concentration on the area of the absorption line.

One disadvantage of the spectrum area method is that the overlap of closely spaced absorption lines causes the absorption lines to be either difficult or impossible to separate. U.S. Patent Application Publication No. 2013/0135619 (filed 2012 Nov. 28 naming assignee Yokogawa Electric Corporation) teaches that the separation of the absorption lines with strong overlapping between the spectrum areas is not possible. This patent application also describes a method for computing the spectrum area by defining the bottom part of the absorption line toward the noise region. One embodiment of the invention disclosed in this patent application uses a reference light for normalizing the intensities at the input and the output of the gas cell, making the measurements insensitive to the changes of the laser output power. Yet another embodiment of the invention described in this patent application has a sealed reference cell containing the analytes used as reference for spectrum areas. The measured spectra areas are compared to spectra areas of the analytes inside the reference cell. Thus, the spectrum area method introduces significant complications in data processing.

There are several additional disadvantages of the spectrum area method including the following: (i) the analyte concentration is related to the area of the absorption line, rather than being related to the peak value of the absorption line after subtracting the noise; (ii) the same absorption peak value can have different spectrum areas, leading to a wrong absorption value; and (iii) absorption line widening causes overlapping of narrowly spaced absorption peaks.

Another known method is the coherent ring-down spectroscopy ("CRDS"), which is based on measuring the decay rate of the power at the output of an optical ring cavity containing the analyte when a pulsed laser beam is incident into the cavity (see: Picarro, "G2401 CRDS Analyzer CO2, CO, CH4, H2O"; https://picarro.app.box.com/shared/3ncm4atiot; U.S. Pat. No. 5,528,040 issued 1996 Jun. 18 to Trustees Of Princeton University; U.S. Pat. No. 7,646,485 issued 2010 Jan. 12 to Picarro, Inc.; U.S. Pat. No. 8,537,362 issued 2013 Sep. 17 to Picarro, Inc.). CRDS is a two-step process. The initial build-up step involves a laser pulse being sent to the cavity, where it is reflected multiple times. The number of reflections depends on the quality factor of the cavity. The subsequent ring-down step involves the laser beam being turned-off. If the laser wavelength is not coincident with an absorption line of an analyte inside cavity, the decay time is very short. If there is a resonant absorption inside the cavity by the analyte, the decay time is proportional with the analyte concentration.

The known methods do not achieve measurement accuracy for the detection of the presence of one or more analytes, and quantitative measurement of one or more analytes. What is needed is an invention that is operable to achieve such measurement accuracy.

SUMMARY OF THE INVENTION

In one aspect, the present disclosure relates to an apparatus operable to measure the content of one or more gas analytes within a gas mixture, said apparatus comprising: a measuring module, comprising: a controller operable to activate a laser beam generator to generate a laser beam; a processor operable to determine the content of the one or more gas analytes within the gas mixture based upon information collected from one or more sensors; a gas cell module connected to the measuring whereby information and commands are transferable between the measuring module and the gas cell module, said gas cell module comprising: a closed gas cell containing the gas mixture and the one or more analytes, said closed gas cell having two transparent windows therein on opposite sides of the closed gas cell; two mirrors having reflective surfaces facing each other positioned on opposite sides of the closed gas cell and each being positioned proximate to one of the transparent windows; the laser beam generator operable to generate or direct a laser beam, said laser beam generator being positioned in proximity to one of the two mirrors, when generated the laser beam being directed towards the mirror on the side of the closed gas cell opposite the laser beam generator, the laser beam being directed so is reflected one or more times between the two mirrors, and in each reflection it passes through all of following: the window in the closed gas cell closest to the laser beam generator; the gas mixture inside the closed gas cell; and the other window in the closed gas cell; a laser beam output operable to receive the laser beam after it has been reflected; and the one more sensors being operable to sense and transfer information pertaining to the laser beam, the gas mixture, and the one or more analytes interaction with the laser beam.

Such an embodiment of the present invention further relates to the gas cell module further comprising: the laser beam generator being an input collimator; a low loss input optical port positioned as integrated in the mirror proximate to the input collimator; the laser beam output being a low loss optical output port positioned as integrated in the mirror opposite the mirror wherein the low loss input optical port is integrated; the laser beam being a collimated input optical beam that is directed through the low loss input optical port at an incidence angle that is in relation to a gas cell axis of the gas cell so that the one or more reflections of the input optical beam between the mirrors gradually direct the collimated input optical beam towards the low loss optical output port; an output collimator operable to collect the optical beam passing through the low loss output optical port; and the one or more sensors including the following: a temperature transducer operable to emit a signal proportional to a temperature of at least one of one or more the analytes; and a pressure transducer operable to emit a signal proportional to the pressure of at least one of one or more the analytes.

Such an embodiment of the present invention further relates to the gas cell module further comprising: the laser beam generator being an input collimator; a low loss input optical port and the laser beam output being a low loss optical output being positioned as integrated in the mirror proximate to the input collimator; the laser beam being a collimated input optical beam that is directed through the low loss input optical port at an incidence angle that is in relation to a gas cell axis of the gas cell so that the one or more reflections of the input optical beam between the mirrors gradually direct the collimated input optical beam towards the low loss optical output port; an output collimator operable to collect the optical beam passing through the low loss output optical port; and the one or more sensors including the following: a temperature transducer operable to emit a signal proportional to a temperature of at least one of one or more the analytes; and a pressure transducer operable to emit a signal proportional to the pressure of at least one of one or more the analytes.

Such an embodiment of the present invention further relates to the measuring module further comprising: the processor receiving information from the gas cell module being operable to determine a single absorption line of the analyte that is unique among all the absorption lines of the gases contained in the gas cell; one or more tunable lasers operable in a spectral interval broader than the absorption linewidth of the analyte to deliver one or more tunable laser beams through a tunable laser single mode optical fiber; one or more reference lasers operable to generate a single line delivery of one or more reference beams through a reference laser single mode optical fiber; a beam combiner operable to merge into a single laser source optical fiber the one or more tunable laser beams and the one or more reference laser beams as a combined beam; a beam splitter operable to receive the combined beam having a tap output through which a fraction of optical power of the combined beam is directed as a fraction beam and a main output through which the balance of the optical power of the combined beam is directed as an output beam, said output beam being directed to the laser beam generator; a reference photodiode operable to receive the fraction beam; a signal photodiode operable to receive the laser beam from the gas cell; a reference logarithmic amplifier operable to convert to reference voltage a high dynamic range photocurrent generated by the reference photodiode; a signal logarithmic amplifier operable to convert to signal voltage a high dynamic range photocurrent generated by the signal photodiode; a DLOG differential amplifier connected at its non-inverting input to the reference logarithmic amplifier, and connected at is inverting input to the signal logarithmic amplifier, said DLOG differential amplifier being operable to generate a referenced absorption signal proportional to the difference between reference voltage at output from reference logarithmic amplifier and signal voltage at output of the signal logarithmic amplifier; the controller being operable to: receive analog signals from the DLOG differential amplifier, and at least one of the one or more sensor; convert analog input voltages to digital output; generate control signals for the one or more tunable lasers and for the one or more reference lasers; communicate with a host processor; and perform determinations; a real time clock; and a non-volatile memory operable to store data that is determinations and information generated by the apparatus.

Such an embodiment of the present invention further relates to the closed gas cell being formed of corrosion resistant material shaped in a tubular form and the windows are positioned at each end of the tubular form on an optical axis of the tubular form, said optical axis being collinear with a geometric axis of the tubular form, said tubular form incorporating a gas input port whereby the gas mixture enters the gas cell, and a gas output port operable as a gas exhaust for the gas mixture, and said closed gas cell being operable to prevent contact of the one or more analytes with optical elements of the apparatus, and said closed gas cell being positioned between the mirrors so as to be perpendicular to each mirror.

Such an embodiment of the present invention further relates to the mirrors being positioned to be parallel and each comprise a circular mirror substrate having a reflective flat surface coated with a low loss coating, and having an anti-reflective surface another surface coated with a low loss antireflective coating, the reflective surface of one mirror incorporating one or more transparent optical ports operable to direct input and output laser beams.

Such an embodiment of the present invention further relates to a display being connected to the measuring module, whereby output information generated by the measuring module is communicated to a user.

Such an embodiment of the present invention further relates to the measuring module being formed of bulk optical components.

In another aspect, the present disclosure relates to an apparatus for measuring the content of one or more gas analytes within a gas mixture, said apparatus comprising: a measuring module, comprising: a controller operable to activate a laser beam generator to generate a laser beam; a processor operable to determine the content of the one or more gas analytes within the gas mixture based upon information collected from one or more sensors; an open gas cell module comprising: an open gas cell wherein the gas mixture and the one or more analytes are present; a reflecting target positioned on one side of the open gas cell; the laser beam generator operable to generate or direct a laser beam, said laser beam generator being positioned opposite to the reflecting target having the one or more analytes between the laser beam generator and the reflecting target, the laser beam being directed from the laser beam generator towards the reflecting target and being reflected from the reflecting target; and a telescope integrated with a transceiver, said telescope being operable to collect the laser beam reflected by the reflective target.

Such an embodiment of the present invention further relates to the open gas cell having at one end the transceiver that is an optical transceiver composed of an input collimator and an output collimator, the input and output collimators facing the reflective target that is a retro-reflector.

Such an embodiment of the present invention further relates to the open gas cell being defined as the space between the reflecting target and the transceiver and can contain any of the following: the one or more analytes; vapors of the one or more analytes; or plasma or liquid containing the one or more analytes.

Such an embodiment of the present invention further relates to converting elements being incorporated in the open gas cell module operable to convert the plasma or the liquid to a gas mixture.

In another aspect, the present disclosure relates to a method for measuring the content of one or more gas analytes within a gas mixture, said apparatus comprising: a method for measuring the content of one or more gas analytes within a gas mixture and monitoring the mass of the one or more analytes, said method comprising the steps of: generating a laser beam from a laser beam generator and gathering the input power of the laser beam; directing the laser beam through a gas cell having a gas mixture containing the one or more analytes therein, the laser beam further being directed to a reflective surface, said reflective surface being operable to reflect the laser beam through the gas cell at least one more time; gathering the output power of the laser beam at the point when the laser beam passes from the gas cell for the last time; transferring the output power and input power to a measuring module; one more sensors generating sensor information related to the laser beam, the gas mixture, and the one or more analytes interaction with the laser beam, and the one or more sensors transferring such sensor information to the measuring module; and the measuring module utilizing the input power, the output beam and any of the sensor information to determine the absorption of the one or more analytes.

Such an embodiment of the present invention further relates to the steps of: sweeping a tunable laser beam wavelength from a minimum wavelength to a maximum wavelength in a spectral region containing the absorption line of the analyte, and sensing the output power of the tunable laser beam upon completion of the sweeping; obtaining a maximum analog voltage at the output of a DLOG differential amplifier dependent on the transmittance of at least one of the one or more analytes at a resonance wavelength; converting of a peak voltage at the output of the DLOG differential amplifier to a digital value with high resolution representing a non-compensated resonant peak absorption by at least one of the one or more analytes; storing the non-compensated resonant peak absorption into a temporary peak register, said non-compensated resonant peak absorption containing a background noise; disabling the tunable laser and activating a reference laser, said reference laser lasing in a spectral range wherein at least one of the one or more analytes are located, and further lasing in a spectral range wherein other gases of the gas mixture contained in the gas cell have negligible absorption, said reference laser beam utilizing the same photodiodes, logarithmic amplifiers, the DLOG differential amplifier and other components as the tunable laser beam; and converting output of the DLOG differential amplifier to high resolution numerical value representing the background noise, and storing said high resolution numerical value in a temporary background noise register.

Such an embodiment of the present invention further relates to the gas cell being a closed gas cell or an open gas cell.

Such an embodiment of the present invention further relates to the steps of the measuring module: determining a compensated absorption utilizing at least one of the one or more analytes by subtracting background noise stored in the temporary background noise register from a peak absorption stored in the temporary peak register; and determining the mass of at least one of the one or more analytes contained in the gas cell utilizing a compensated absorption of the at least one of the one or more analytes, temperature and pressure of the at least one of the one or more analytes, volume of the gas cell, and constants of the one or more sensors as collected by the during a calibration process.

Such an embodiment of the present invention further relates to the steps of: determining a peak absorption of at least one of the one or more analytes to a wavelength accuracy limited by a linewidth of the a laser beam that is generated by a tunable laser; determining a wavelength and a peak absorption value of at least one of the one or more analytes independent of other gases in the gas cell and of total pressure of the gas mixture in the gas cell; and determining statistical information utilizing one or more true absorption values for increasing the sensitivity of the instrument.

Such an embodiment of the present invention further relates to the step of utilizing one absorption line of at least one of the one or more analytes that overlap partially with another absorption line of other gas components contained in the gas cell.

Such an embodiment of the present invention further relates to any one or more of the following: a laser source is utilized that matches a selected absorption line of at least one of the one or more analytes as the laser generator; a laser generator is utilized that is one or more tunable lasers generators for generating multiple tunable laser in different narrow spectral ranges; the laser beam is multiple laser beams including laser beams that are tunable in a narrow tuning range and laser beams that are tunable in a broad tuning range; the multiple laser beams covering a broad tuning range; and multiple reference laser are utilized for measuring background noise.

Such an embodiment of the present invention further relates to a measuring module comprising bulk optical elements, further comprising the steps of: combining the laser beams that are tunable laser beams and a reference laser beam into a combined laser source beam, said tunable laser beams being generated by a tunable laser generator and said reference laser beam being generated by a reference laser generator; transmitting a sample of the laser source beam to a reference photodiode and transmitting the laser source beam content other than the sample to an input collimator of the gas cell; collimating the laser beam directed to the gas cell; and collecting the laser beam emerging from the gas cell and sending it to a signal photodiode.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The invention will be better understood and objects of the invention will become apparent when consideration is given to the following detailed description thereof. Such description makes reference to the annexed drawings wherein:

FIG. 8 is a perspective view of the gas cell module of the apparatus of the present invention.

Figure 1:
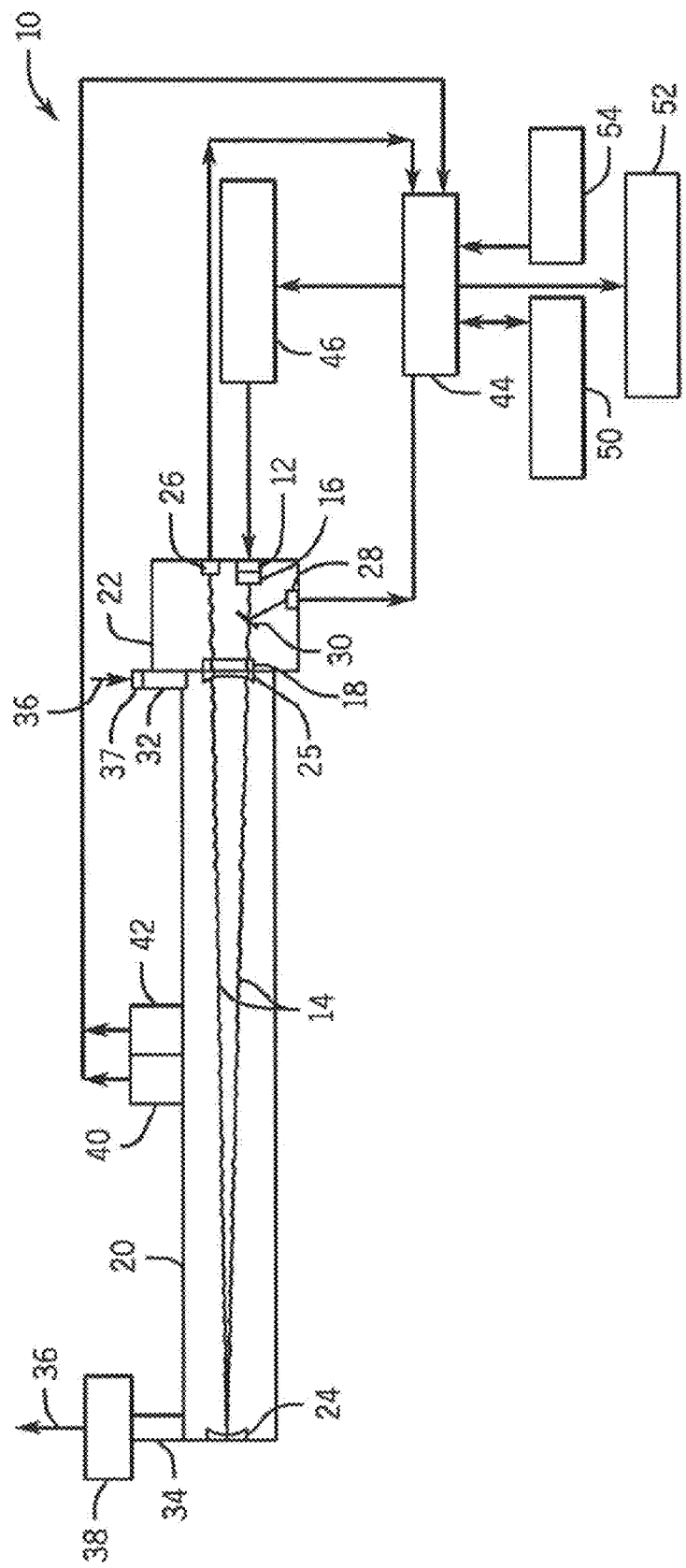
FIG. 1 is a schematic drawing of an example of the prior art.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION OF THE INVENTION

The present invention relates to a method, apparatus and system for measuring the content of either one or more gas analytes that may be part of a gas mixture. The present invention applies a spectroscopic method that utilizes an extremely narrow linewidth laser beam that is absorbed when its wavelength is swept across the interval containing the absorption line of the analyte. The method, apparatus and system of the present invention is applicable to any analyte in gas phase that is part of a gas mixture, or to any analyte in a plasma phase, as well as analytes in other environments.

The present invention provides a method, apparatus and system operable to achieve high sensitivity measurement of the mass of an analyte within a gas mixture, such measurement being provided to a user of the method, apparatus and/or system as a delimited volume defined by a gas sampling cell. Embodiments of the present invention achieve this measurement by undertaking several steps. The present invention is operable to split an incident narrow linewidth optical beam into a measuring beam going through a gas sampling cell and a reference beam propagating outside of the gas sampling cell. The present invention further is operable to find the absorption in the gas cell by determining the ratio between the optical power of the measuring beam at the exit of the gas cell and the optical power of the reference beam. The present invention is also operable to sweep the wavelength of a tunable laser within a wavelength range broader than the absorption linewidth of the analyte to find the absorption peak of the analyte. The present invention is additionally operable to find the background absorption of optical elements and of photo detection channels by using a reference laser to generate a narrow linewidth at which the analyte as well as all other gases of the gas mixture have an insignificant absorption. The present invention is further operable to find the true absorption of the analyte by subtracting the background absorption from the absorption peak of the analyte.

The method applied in embodiments of the present invention is a Differential Swept Wavelength Absorption Spectroscopy ("DSWAS") method. The DSWAS method is applied to cause the present invention to be operable to monitor the mass of the analyte contained in a gas mixture and calculate the results of this monitoring as a delimited volume. Such delimited volume is referenced herein as a gas sampling cell, or simply a gas cell.

Embodiments of the apparatus of the present invention are operable to apply the DSWAS method, and contain a measuring module and a gas cell module for monitoring the content of an analyte. The gas cell may be a closed gas cell that is formed as a cylindrical tube with highly transmissive optical windows at each end of the tube. An optical axis exists between the optical windows. The closed gas cell may be positioned perpendicular or collinear to the cylinder axis, which is also the gas cell axis. The optical windows function to allow a light beam to reach inside the gas cell and interact with the gas mixture containing the analyte inside the gas cell. The cylindrical tube may incorporate a gas intake port and a gas exhaust port operable to achieve the circulation of the gas mixture containing the analyte through the gas cell. The intake gas port and exhaust gas port may both be connected to the gas cell by flexible elements such as bellows operable to minimize the influence of external shocks and vibrations upon the apparatus from affecting the positioning of the optical windows and/or any light beam passing through such windows into the closed gas cell. The flexible connections thereby protect the monitoring process and the accuracy of the measurements performed by the method, apparatus and system of the present invention. The gas cell may be removable from the optical system for maintenance purposes and repositioned with minimum repositioning effort or steps. A controller may be integrated in the apparatus of the present invention that is operable to monitor the operation of the entire apparatus, and to communicate with a host or a user of the apparatus.

In embodiments of the present invention the closed gas cell may be located between two parallel or virtually parallel reflective mirrors. Each of the mirrors may be positioned perpendicular to the optical axis that is coincident with the cylinder axis. A light beam incident at small angle with the optical axis is reflected multiple times by both mirrors without interference. The light beam is operable to pass through each of the optical windows and inside the cylinder between the optical windows at each pass between the mirrors. An optical interaction path is formed inside the closed gas cell where the light beam crosses within the closed gas cell, and the path includes the lengths of the light beam within the closed gas cell that are formed each time the light beam is reflected. As the optical interaction path is formed from the multiple reflections of the light beam within the closed gas cell, the optical interaction path is much longer than the length of the closed gas cell. The light beam interacts with the analytes along the optical interaction path. As the mirrors are positioned outside the closed gas cell, the mirrors are not contaminated by the gas that flows through the gas cell.

In embodiments of the present invention the gas cell may have an open configuration consisting of an optical transceiver composed by an optical transmitter, as well as an optical receiver and a back reflector for monitoring the analyte contained in the space between the transceiver and the back reflector.

In embodiments of the present invention the closed gas cell and the open gas cell may incorporate temperature and pressure sensors for monitoring the temperature and pressure of the gas mixture within the closed gas cell or open gas cell. The same optical layout for generating and handling the beam can be used either with the closed gas cell or with open gas cell. The optical layout may be altered in embodiments of the apparatus of the present invention, for example, such as the back mirror facing the input fiber optic collimator being replaced with a retro reflector, the input fiber optic collimator being replaced with a bulk optics collimator, the output fiber optic collimator being replaced with an output fiber coupled telescope, while the temperature sensor and the pressure sensor may remain the same or essentially the same.

The optical layout of the measuring module may consist of beam combiners, beam splitters, beam collimator and the receiving lens. In embodiments of the present invention the optical layout of the measuring module may be formed with bulk optical elements when using either the closed gas cell or opened gas cell.

In an embodiment of the present invention the apparatus may be configured so that the optical layout of the measuring module is formed of bulk optical elements, the opened gas cell elements is configured to produce free space propagation, the back mirror facing the input fiber optic collimator and the output fiber optic collimator is replaced with a retro reflector, the input fiber optic collimator is replaced with a bulk optics collimator, the receiving fiber optic collimator is replaced with output telescope, and the temperature sensor and the pressure sensor monitor the respective ambient temperature and the ambient pressure of the gas in the gas cell.

In embodiments of the present invention a single resonant absorption line of each analyte may be utilized for monitoring the content of the analyte, providing that this line is unique among all the absorption lines of the gas mixture existing either in the closed gas cell or in the open gas cell. Various lasers may be incorporated in the present invention that are operable to scan the wavelength across the absorption peaks or the transmission dips of multiple analytes, for example, such as, a single tunable laser source ("TLS"), multiple TLS's for multiple analytes, or a broad tuning range laser ("BTRL"). A TLS or DFB laser incorporated in the present invention must have a tuning range that contains the selected resonant absorption line of the analyte. The light absorption in the gas cell may be measured as the difference between the logarithm of the optical power at the output of the gas cell and the logarithm of the output power at the input of the gas cell at any wavelength of the tunable laser. The absorption peak ("AP") value may be proportional with the mass of the analyte inside the gas cell. The difference between the logarithm of the optical power at the output of the gas cell and the logarithm of the output power at the input of the gas cell at any wavelength of the tunable laser, or the power ratio, may be independent of the beam power and of its wavelength. This is an aspect of the DSWAS method.

Embodiments of the present invention may be operable to measure the noise of the optical layout and of the photo detection channels across the spectral interval of interest or close to this spectral interval. Such noise may be identified as background noise. The measurement of noise is calculated by measuring the absorption at a reference wavelength where there is very insignificant absorption of the analyte as well as of the other gases of the mixture in the gas cell. The background noise may be subtracted from the measured absorption peak to determine the true or compensated absorption peak, free of residual absorption of the optical layout as another aspect of the DSWAS method.

In embodiments of the present invention the wavelength of the reference laser must be in a spectral region with the lowest possible absorption by analyte and other gases of the gas mixture in the gas cell.

In embodiments of the present invention light absorption can be measured by incorporating photodiodes connected either to logarithmic amplifiers, or to a combination of logarithmic and linear amplifiers and lock-in amplifiers, in the apparatus of the present invention. The photodiodes so connected are operable to achieve increased dynamic range and sensitivity and thereby are operable to produce measurements of light absorption.

In one embodiment of the present invention a module comprises the closed gas cell, two flat mirrors, an input fiber optic collimator and an output fiber optic collimator. The module is mountable in a high stability optical cage system. The optical cage may incorporate vibration dampers operable to minimize the influence of environmental shocks and vibrations that occur upon the optical system. Mirror holders may be mounted on the optical cage, and the mirrors may each to be held within its respective mirror holder.

The closed gas sampling cell of the present invention may be formed of corrosion resistant material, for example, such as stainless steel, alumina silicate, ceramics, glass ceramics, high density magnesium oxide, or other corrosion resistant materials. The closed gas sampling cell may incorporate windows, such as transparent windows, and the windows may be made of a corrosion resistant substrate, for example, such as fused silica, silicon, germanium, or other corrosion resistant substrate. The gas cell may further be configured so that the gas cell may be serviced without dismantling the entire optical setup (e.g., the laser beam, the positioning of the mirrors, the positioning of the gas cell between the mirrors, etc.).

A high transmittance input optical port may be incorporated in each mirror whereby the incident optical beam passes inside the gap between each mirror and the gas cell. Each mirror further may incorporate an output optical port whereby the optical beam emerging from the closed gas cell exits therefrom with minimum losses. The present invention may further incorporate an input beam collimator operable to provide the input light beam into the closed gas cell, and an output beam collimator operable to collect the light beam emerging from the closed gas cell. The input beam collimator may be either coupled with single mode optical fiber, or formed to incorporate bulk optical components. The output beam collimator or telescope may be either coupled with optical fiber, or formed to incorporate bulk optical components. The input beam collimator and output beam collimator may be fiber optic collimators, and may be mounted in collimator holders that are incorporated in the optical cage.

Embodiments of the present invention may incorporate multiple optical elements in the apparatus, for example, such as lasers, beam splitters, beam combiners and photodiodes. These optical elements may be integrated into an optical setup that is formed to incorporate either single mode optical fibers, or bulk optical components. The apparatus may be reconfigurable for any analyte by selecting the lasers, the photodiodes, the windows of the closed gas cell, fiber optic components and bulk optical elements required for matching the spectral interval of the specifically identified analyte. In such an embodiment of the present invention the DSWAS method operating principle is consistent with that of configurations of the apparatus for detections of other analytes.

In embodiments of the present invention, the gas mixture flowing through the gas cell may be derived from an evaporating liquid the vapours of which are recirculated by fans through the closed gas cell.

In embodiments of the present invention the apparatus operable to apply the DSWAS method is further operable to monitor the analyte in solid phase by converting the analyte to plasma phase and to gas phase through laser induced breakdown ("LIB") either inside the closed gas cell, or in an open gas cell configuration.

The present invention is operable to monitor the content of an analyte or gas component within a gas mixture. One embodiment of the apparatus of the present invention (referenced herein as an Apparatus Embodiment), comprises:

a gas cell module that is a closed gas sampling cell consisting of a corrosive resistant tube with two parallel highly transparent windows at opposite ends of the tube that are held in place by their respective window caps, the tube and the windows delimiting a measuring volume for the analyte;

two parallel highly reflective layers perpendicular to the axis of the gas cell that is contained between these layers which are coated on mirrors' substrate;

an input fiber optic collimator sending a collimated laser beam into the gap between the mirrors at small but not a zero incidence angle, for example, such as 0.1 degrees or another angle, the beam from the input fiber optic collimator being reflected multiple times between the reflective layers and said beam passing through the gas cell at each reflection path between the mirrors;

an output fiber optic collimator for collecting the low divergence light beam emerging from the gas cell after numerous reflections on reflective layers;

a cage system holding the gas cell mounted in its holders, the cage system also incorporating mirror holders wherein each of the two mirrors are mounted, and collimator holders wherein each of the input collimator and output collimator are mounted;

an intake tube and an exhaust tube connected to the gas cell, each of the intake tube and the exhaust tube incorporating vibration damping means;

a measuring module comprising at least one tunable laser source ("TLS") operable to controllably sweep its wavelength across a spectral interval containing the absorption line of the analyte;

a combination of fiber optic couplers and splitters for directing a specific small fraction of the TLS beam to a reference photodiode operable to monitor the optical power at the gas cell input, most of the optical power being directed towards the input fiber optic collimator and further towards the entrance of the gas cell;

an output photodiode operable to monitor the optical power at gas cell output;

one or more logarithmic amplifiers operable to convert to voltage the high dynamic range photocurrent from each photodiode;

a DLOG differential amplifier operable to calculate at the output the difference of signals from logarithmic amplifiers' outputs independent of the laser output power and its wavelength, the peak value of the difference being used for computing the optical absorption inside the gas cell up to two constants defined during calibration;

a means for computing the mass of the analyte being computed from optical absorption;

at least one reference laser ("REFL") having its wavelength directed into a spectral region with negligible absorption by the analyte and also absorption by the other gases of the gas mixture inside the gas cell, the REFL beam having the same optical path as the TLS beam, the REFL beam being utilized to determine the background noise of the optical layout and of the photo detection channels and being utilized to determine the quality of the optical layout; and a controller operable to generate the required commands for the operation of the lasers, and operable to: receive signals from the lasers; convert the analog peak value of the DLOG differential amplifier to digital format; subtract the bias noise from the peak of the DLOG differential amplifier output to determine the compensated value of the analyte absorption; receive analog signals from temperature and pressure sensors and convert such signals to numerical format; and communicate with a host unit through digital and analog signals in a two-way format.

The apparatus of the present invention may be utilized so that a pipe or an equivalent element carrying a gas mixture containing the analyte to be monitored is attached or otherwise directed to the closed gas cell intake so that the gas will flow through the pipe into the closed gas cell intake port. The output port of the gas cell may be utilized to expel gas from the gas cell, for example, such as gas being expelled from the gas cell into a gas container, such as a pipe. It is also possible that the gas mixture may be generated from a liquid containing the analyte, and may be vapours from the liquid. The gas mixture may also be generated from a laser induced breakdown ("LIB") plasma and vapors containing the analyte.

In one embodiment of the present invention (referenced herein as the "Measuring Embodiment"), the measuring module is formed of bulk optical components operable to do all of the following:

combine the beams from two or more tunable lasers ("TLS") into a single swept wavelength beam;

combine the beams from two or more reference lasers ("REFL") into a single reference wavelength beam;

combine the single swept wavelength beam with the single reference wavelength beam on the same interrogation beam;

split the interrogation beam in two beams with different intensities, the high intensity beam being directed to the input of the gas cell and the low intensity beam being directed to a reference photodiode for monitoring the optical power at the input of the gas cell;

collimate the beam directed to the entrance of the gas cell; and collect the beam emerging from the gas cell and for directing it to the output photodiode used for monitoring the beam power at the gas cell output.

The measuring module may incorporate:

one or more logarithmic amplifiers operable to convert the high dynamic range photocurrents from each photodiode to output voltages;

a DLOG differential amplifier operable to cause the difference of signals coming from logarithmic amplifier outputs to be proportional to the optical absorption inside the cell up to two constants defined during calibration, and the absorption of the analyte being indicated by the peak value at the output of the DLOG differential amplifier when sweeping the TLS wavelength across the absorption linewidth of the analyte;

a reference laser ("REFL") operable to determine the bias noise of the optics and of the photo detection channels, and also operable to determine the quality of the optical layout, the REFL wavelength belonging to a spectral region with negligible absorption by the analyte and also by the other gases of the gas mixture inside the gas cell, the REFL beam having the same optical path as the beam from tunable lasers;

a controller operable to: generate all the required commands for the operation of the lasers; receive the feedback signals from the lasers; convert the analog peak of the DLOG differential amplifier to digital format; subtract the bias noise from the peak of the DLOG differential amplifier to determine the compensated value of the analyte absorption; convert the analog signals from temperature and pressure sensors to numerical format; and communicate with a host through digital and analog signals;

a pipe or tube of gas provided by a user, such as a user from an industrial plant that contains a gas mixture containing the analyte that is be monitored, and the pipe or tube is attached or otherwise directed to the gas cell intake so that at least a portion of the gas will flow through the pipe into the closed gas cell intake port gas and into the gas cell, and in a closed cell embodiment of the present invention, the gas can also be vapors of a liquid containing the analyte, or laser induced breakdown ("LIB") plasma and vapors containing the analyte.

In an embodiment of the present invention, the measuring module is formed of fiber optic components of the Apparatus Embodiment (as discussed herein), excepting the closed gas cell element which, and instead the gas cell module is an open gas cell consisting of a transceiver module comprising as major elements (referenced herein as the "Open Apparatus Embodiment"): a bulk optics beam collimator for sending the beam toward a target; a retro reflecting target sending back to the transceiver the incident beam; and a telescope as part of the transceiver for collecting the beam reflected by the target. The gas mixture to be monitored can contain one or more of the following: the analyte within the free space between the transceiver and the retro reflector; vapors of the analyte either existing or produced in the space between the transceiver and the retro reflector; and LIB plasma or vapors containing the analyte generated in free space between the transceiver and the retro reflector.

In an embodiment of the present invention, the measuring module is formed of bulk optical components as in the Measuring Embodiment (as discussed herein), and the gas cell module is an open gas cell as in the Open Apparatus Embodiment (as discussed herein), and gas mixture to be monitored can be one or more of the following: the analyte within the free space between the transceiver and the retro reflector; vapors of the analyte either existing or produced in the space between the transceiver and the retro reflector; and LIB plasma or vapors containing the analyte generated in free space between the transceiver and the retro reflector.

In embodiments of the present invention the gas mixture to be monitored may be any of the following: a gas mixture flowing through a pipe; a vapor phase of the analyte flowing either through a closed gas cell or through an open gas cell; plasma of any solid target produced by LIB containing the analyte produced either inside a closed gas cell or into an open gas cell.

In embodiments of the present invention, the wavelength of TLS with linewidth much narrower than the absorption line of the analyte may be swept across a wavelength interval wider than the absorption linewidth of the analyte to determine the absorption peak of the analyte independent of the wavelength and of the power of the laser beam.

In embodiments of the present invention, the wavelength of the reference laser ("REFL") having negligible drift may be in the spectral region where there is no significant absorption either of the analyte or of any other gas component of the gas mixture.

In embodiments of the present invention, the absorption measured at the wavelength of the REFL may be considered to be the background noise level (BSN).

In embodiments of the present invention, the compensated absorption peak may be obtained by subtracting BSN from the absorption peak ("AP").

In embodiments of the present invention, there may be an embedded controller with input-output ports and digital-to-analog converters operable to undertake one or more of the following: activate the lasers in appropriate time sequence; sweep the wavelength of one or more tunable lasers TLS; convert to digital value the peak output of the DLOG differential amplifier; convert to digital value the output of the DLOG differential amplifier when the REFL is active to determine the background noise; numerically subtract the background noise from the peak of the DLOG differential amplifier; convert to digital value the analog signals from the temperature sensors and from the pressure sensors; and compute the analyte mass and communicate the analyte mass in both numerical format and analog format to a host unit.

In embodiments of the present invention, the monitoring unit may be configurable to be operable to undertake one or more of the following: use any tunable wavelength range; perform any possible use of multiple tunable wavelength ranges; use any reference wavelength and perform possible uses of multiple reference wavelengths.

In embodiments of the present invention, all the lasers of the measuring module may be continuous wave lasers.

In embodiments of the present invention, a single unit may monitor either a single analyte or multiple analytes.

The method, apparatus and system of the present invention function in accordance with at least the following assumptions: (i) the analyte in gas phase has a discrete absorption spectrum; (ii) the selected absorption line of the analyte is unique among all the absorption lines of all components of the gas mixture containing the analyte; and (iii) a single absorption line of the analyte is sufficient for detection of the existence of the analyte within a defined volume and also for measuring the analyte mass contained in that volume.

One embodiment of the present invention incorporates an apparatus that is operable to achieve a differential swept wavelength absorption spectroscopy ("DSWAS") method. The apparatus comprises analytical instruments operable to monitor the mass of an analyte. The apparatus comprises: a gas cell module that incorporates: a closed gas cell containing a gas mixture wherein there is at least one analyte; at least one mirror substrate with at least one port therein, having flat, parallel surfaces; at least one mirror substrate devoid of any port, having flat, parallel surfaces; an input collimator; a collimated input beam; an output collimator; a temperature transducer; a pressure transducer; a measuring module operable to monitor the content of an analyte that incorporates at least one tunable laser; at least one reference laser; a beam combiner, a beam splitter; a reference photodiode; a signal photodiode; a reference logarithmic amplifier; a signal logarithmic amplifier; a DLOG differential amplifier; and a controller. Each of these elements are discussed in more detail below.

The closed gas cell is preferably formed of corrosion resistant materials shaped in a tube having one transparent optical window at each end that are positioned perpendicular to the optical axis of the tube. Said optical axis of the tube is collinear with the geometric axis of the tube. The closed gas cell having one port for gas entrance and another port for gas exhaust, whereby flow of the gas analyte through the closed gas cell is facilitated. The closed gas cell prevents the contact of the corrosive analyte with the optical elements of the apparatus. The closed gas cell may be removeable from the apparatus, for example, such as for maintenance or cleaning, and the gas cell may be repositionable with minimal affect to or influence on the optical alignment of the gas cell. The gas cell may be configured so as to facilitate interaction between a gas analyte and a laser beam, and to define an interaction volume in the interior of the gas cell.

The mirror substrate with at least one port therein may have one surface that incorporates a low loss (e.g., maximum 0.1% loss) and highly reflective (e.g., minimum 99% reflective) layer. The layer may be a coating, for example, such as a dielectric coating. The surface may have one or two transparent optical ports for input and output beams. The other surface of the mirror may have a low loss anti-reflective coating. The mirror may be circular in shape.

The mirror substrate without any port therein may have one surface that incorporates a low loss (e.g., maximum 0.1% loss) and highly reflective (e.g., minimum 99% reflective) layer. The layer may be a coating, for example, such as a dielectric coating. The other surface of the mirror may have a low loss anti-reflective coating. The mirror may be circular in shape.

The closed gas cell is positioned between the reflective layers of mirrors, the optical axis of the gas cell being perpendicular to each of the reflective layers. The mirrors may be positioned to be parallel or virtually parallel to each other.

The input collimator is operable to deliver a collimated input optical beam in the spacing between the reflective layers of the mirrors. The optical beam may be delivered at a small incidence angle (0.1 degree or less) in relation to the gas cell axis.

The collimated input beam is directed so as to enter a space between the reflective surfaces of the mirrors through a low loss input optical port located on the input mirror optical substrate. The entrance of the collimated input beam does not pass through any reflective layer. The beam is reflected between the reflective surfaces of the mirrors. There may be multiple reflections of the input optical beam between the reflective layers. Each reflection may gradually direct the beam towards a low loss optical output port located on the substrate of the output mirror (e.g., the mirror that incorporates at least one port). The beam is directed through the output port without passing through any reflective layer or through any part of any reflective layer. The path of the optical beam going as it is reflected between the mirrors passes through the gas cell. As the beam may be reflected multiple times, the path of the beam may include passes through the gas cell. The total length of the path of the beam is of a greater length than the length of the gas cell.

The interaction length between the light beam and the analyte will depend on several factors, including at least the following: the length of the gas cell; and the incidence angle of the input beam where it enters the spacing between the reflective layers.

The output collimator is operable to collect the optical beam passing out of the gas cell and through a low loss output optical port located on the mirror optical substrate.

An embodiment of the present invention may incorporate an opened gas cell having at one end an optical transceiver composed of an input collimator and an output collimator. Each of the collimators may be positioned to be facing a retro-reflector. An analyte may be positioned between the optical transceiver and the retro-reflector.

The temperature transducer may be operable to produce a signal proportional to the temperature of the analyte. The pressure transducer may be operable to produce a signal proportional to the pressure of the analyte.

The method of the present invention may utilize a single absorption line of the analyte that is unique among all the absorption lines of the gases contained in the gas cell.

The tunable laser may be operable in a spectral interval broader than the absorption linewidth of the analyte. The interval contains the selected absorption line of the analyte. The laser linewidth may be in the 0.01 pm range, and be much narrower than the absorption linewidth of the analyte.

The absorption linewidth of the analyte may be between 10 pm and 150 pm. The tunable laser may deliver a beam through a single mode optical fiber.

The reference laser may be operable to generate a single line. The line may be below 1 pm linewidth. Preferably the reference laser delivers its beam through a single mode optical fiber.

The beam combiner is operable to merge the beam directed from the tunable laser and the beam directed from the reference laser into the same laser source optical fiber.

The beam splitter being operable to receive as input the beam from the beam combiner. The beam splitter is further operable to provide at its tap output a small fraction, for example, such as about 1%, of the power of the input beam. The beam splitter provides at its main output the balance of the optical power directed to the input collimator of the gas cell.

The reference photodiode is operable to receive at its input the reference beam from the tap output of the beam splitter. The signal photodiode is operable to receive at its input the output beam from the gas cell.

The reference logarithmic amplifier is operable to convert to reference voltage the high dynamic range (for example, such as about six decades or more) photocurrent generated by the reference photodiode according to a logarithmic function. The signal logarithmic amplifier is operable to convert to signal voltage the high dynamic range (for example, such as about six decades or more) photocurrent generated by the signal photodiode according to the same logarithmic function as the reference logarithmic amplifier.

The DLOG differential amplifier is connected at its non-inverting input to the output of the reference logarithmic amplifier, and at its inverting input to the output of the signal logarithmic amplifier. The DLOG differential amplifier is operable to generate at its output the referenced absorption signal proportional with the difference between the reference voltage at the output of the reference logarithmic amplifier and the signal voltage at the output of the signal logarithmic amplifier. The DLOG amplifier may also incorporate a lock-in amplifier for increasing sensitivity.

The controller is operable to receive the analog signals from the DLOG differential amplifier, and the signals from the temperature and pressure sensors. The controller is further operable to convert all analog input voltages from analog to digital, including performing conversions of high accuracy (for example, such as minimum 16-bit) analog to digital. The controller is also operable to generate the control signals for the tunable laser and for the reference laser. The controller is additionally operable to communicate with a host processor or user. The controller may incorporate a real-time clock. The controller may also incorporate a non-volatile memory operable for storing all measured data received by the controller. The controller may be operable to incorporate a time stamp in the data for reference purposes.

The controller sweeps the wavelength of the tunable laser across the spectral interval containing the absorption line of the analyte. The controller 290 detects the peak of the RDLO output 268 of the DLOG amplifier 256 as voltage proportional with the transmittance through the gas cell independent of laser power. Upon such detection the controller undertake the following steps: it stops the wavelength sweep and converts the RDLO peak to a digital value of minimum 16-bits accuracy; it determines the raw mass of the analyte $rm_W$ inside the gas cell using equation (15); it determines the partial pressure of the analyte $p_W$ inside the gas cell or another user defined parameter; it displays the concentration of the analyte in a format selected by the user; and it communicates the results of its determinations with a host in digital format. The communication between the controller and the host may be utilize serial communication, for example, such as RS232, RS485, Modbus, Ethernet, or be in analog format such as a 4-20 mA current loop, 0-10V.

In another embodiment of the present invention the DSWAS method operable to monitor the mass of an analyte, may incorporate the following steps:

the controller may trigger a monotonic sweep of tunable laser's wavelength from a minimum wavelength to a maximum wavelength within a spectral region containing the absorption line of the analyte, without additional wavelength modulation;

the absorption peak may be detected at the output of the DLOG differential amplifier when the wavelength of the tunable laser equals the resonance wavelength of the absorption peak of the analyte;

the maximum analog voltage may be obtained at the output of the DLOG differential amplifier dependent only on the transmittance of the analyte at the resonance wavelength, being independent on the power of the laser beam which is rejected at common mode;

the controller may convert the peak voltage at the output of the DLOG differential amplifier to digital value with high resolution (minimum 16-bits) representing the non-compensated resonant peak absorption by the analyte, storing this value into a temporary peak register, and the peak absorption value may contain a background noise;

the controller may disable the tunable laser and activate the reference laser lasing in a spectral range where the analyte and eventually other gases of the gas mixture contained in the gas cell have negligible absorption (the reference laser beam may follow the same optical path as the beam of the tunable laser);

the controller may use the same photodiodes, logarithmic amplifiers, the DLOG differential amplifier and other components as the beam generated by the tunable laser, and the controller may convert the output of the DLOG differential amplifier to high resolution (for example, such as minimum 16-bit) numerical value representing the background noise, and store the numerical value representing the background noise in a temporary background noise register.

In such a method the reference laser must have a narrow linewidth in a spectral region with the lowest possible absorption.

The DSWAS method may further include the following steps:

subtracting the background noise stored in the temporary background noise register from the peak absorption stored in the temporary peak register to determine the compensated absorption by the analyte; and determining the mass of the analyte contained in the gas cell utilizing as inputs to the determination the compensated absorption of the analyte, the temperature and pressure of the analyte, the volume of the gas cell and the constants of the sensors identified during the instrument's calibration.

The DSWAS method may further include the following steps:

determining the peak absorption of the analyte utilizing the wavelength accuracy that is limited by the linewidth of the tunable laser, without widening the analyte's absorption peak, independent of the absorption linewidth;

measuring the peak absorption of the analyte without virtual widening the analyte's absorption linewidth;

finding the wavelength and the value of the peak absorption of any analyte independent of the presence of other gases in the gas cell and of the total pressure of the gas mixture in the gas cell; and performing statistical computations with the calculated true absorption values for increasing the sensitivity of the apparatus;

The DSWAS method may further optionally use any of the following:

only one absorption line of the analyte, not overlapping completely another absorption line of other gas component contained in the gas cell;

any tunable laser source matching the selected absorption line of either one analyte or of multiple analytes;

multiple lasers tunable in different narrow spectral ranges;

one or more tunable lasers covering a broad tuning range;

a combination of lasers tunable in a narrow tuning range with lasers tunable in a broad tuning range; and more than one reference laser for measuring the background noise;

The DSWAS method may utilizes a measuring module comprising bulk optical elements to achieve the following in addition to steps for monitoring the mass of an analyte described herein:

combining the beams generated by tunable and reference lasers into a laser source beam;

sending a sample of the laser source beam to the reference photodiode and the balance of the laser source beam to the input collimator of the gas cell;

collimating the beam delivered to the gas cell; and collecting the beam emerging from the gas cell and sending it to the signal photodiode;

The apparatus of the present invention may incorporate one or more of the following elements in addition to the elements discussed herein:

a measuring module comprising with fiber optic elements;

an open gas cell module comprising an input fiber optic collimator operable to direct the collimated incident input optical beam to free space containing the analyte;

a remote retro-reflector operable to achieve back reflection of the input incident optical beam as it passes again through the same free space containing the analyte;

a fiber optic telescope operable to collect the back reflected beam passing twice through the free space containing the analyte;

a closed gas cell module connected to an evaporator containing the analyte in a liquid phase the evaporator being operable to bring the analyte to a gas phase by evaporating the liquid into a gas, and to circulating the analyte continuously through the gas cell;

a closed gas cell module containing a nacelle for holding a solid matter embedding the analyte, and a transparent window, and a pulsed high energy laser operable to generate a beam to pass through the transparent window of the gas cell to produce laser induced breakdown (LIB) at the incidence of the beam on the solid matter target inside the gas cell, so that the LIB is confined by the gas cell containing plasma to produce vapors of the analyte embedded into the solid matter and a means of circulating the vapors within the gas cell;

one or more delivery means operable to deliver the beams of tunable laser and of reference laser inside the gas cell;

a gas cell module comprising bulk optics operable to deliver the input beam into the gas cell, and the gas cell further comprising bulk optics operable to collect the beam emerging from the gas cell;

an open gas cell module wherein the analyte is either a plasma or vapors produced by LIB when a high energy beam from a pulsed laser is incident on a solid matter embedding the analyte; and a gas cell incorporating a input fiber optic collimator and a output fiber collimator positioned on opposite sides of the gas cell;

a gas cell incorporating a nacelle operable to hold a solid state sample containing the analyte, and the gas cell further incorporating a transparent window whereby a beam from a pulsed high energy laser may be pass to be directed to the solid state sample;

The apparatus may incorporate mirrors formed from an optical transparent substrate having high quality flat and parallel surfaces, being a first and a second surface, that are coated in accordance with one of the following: a first surface of the optical transparent substrate having a high reflectivity, low loss optical coating across the entire aperture except one clear optical port for light entrance inside the gas cell and another clear optical port for light exit from the gas cell, preferably these ports being opposed on the same diameter; a first surface of the optical transparent substrate having a high reflectivity coating covering the entire area of the aperture except one clear optical port used either as entrance port of the light inside the gas cell, or exit port from the gas cell; or a first surface of the optical transparent substrate having a high reflectivity, low loss coating covers the entire aperture of the substrate; and the second surface of the optical transparent substrate having an anti-reflective coating thereon.

The apparatus of the present invention incorporating a front mirror assembly for use with a gas cell having at least two optical collimators located on the same side of the gas cell, said front mirror assembly comprising: a mirror plate operable for attaching a mirror mount on its surface and having holes therein, said holes being operable for mounting the front mirror assembly upon a cage system wherein the gas cell is mounted; a mirror holder operable for rigidly mounting either the substrate of the front mirror with one optical port, or the substrate of the back mirror without optical ports, and the mirror holder being movable along two axes on the surface of the mirror plate so as to be perpendicular to the optical axis of the gas cell to achieve optimum alignment of the input and output optical ports facing towards the gas cell; a locking means, operable to lock the mirror holder in a specific position and to angularly angular adjust the mirror substrate in the direction towards the optical axis of the gas cell. The mirror plate and the mirror holder may be of the same design, being operable without any restriction either for the front mirror or for the back mirror.

The apparatus of the present invention incorporating a front mirror assembly for use with a gas cell having two optical collimators located on opposite sides of the gas cell, said front mirror assembly comprising: two mirror plates, each mirror plate to be positioned at opposite ends of the gas cell, each mirror plate being operable to attaching a mirror mount on the surface of the gas cell, and each mirror plate having holder therein, said holes being operable for mounting the front mirror assembly upon a cage system wherein the gas cell is mounted; a mirror holder operable for rigidly mounting either the substrate of the front mirror with one optical port, and the mirror holder being movable along two axes on the surface of the mirror plate so as to be perpendicular to the optical axis of the gas cell to achieve optimum alignment of the input and output optical ports facing towards the gas cell; a locking means, operable to lock the mirror holder in a specific position and to angularly angular adjust the mirror substrate in the direction towards the optical axis of the gas cell. The mirror plate and the mirror holder may be of the same design, being operable without any restriction either for the front mirror or for the back mirror.

The apparatus of the present invention incorporating a collimators assembly for use with a gas cell having two optical collimators located on the same side of the gas cell comprising: a collimator plate at one end of the gas cell that is operable for attaching both collimator mounts on its surface, said collimators plate having holes therein, said holes being operable for mounting the collimators plate upon a cage system wherein the gas cell is mounted; an input collimator mount wherein the input collimator is mountable and may be rigidly held in a position and locked in such position on the collimator plate, and the input collimator mount being movable along two axes on the surface of the collimator plate so as to be perpendicular to the optical axis of the gas cell to achieve optimum alignment of the input collimator facing towards the gas cell; an output collimator mount (which may be of the identical configuration to the input collimator mount) wherein the output collimator is mountable and may be rigidly held in a position and locked in such position on the collimator plate, and the output collimator mount being movable along two axes on the surface of the collimator plate so as to be perpendicular to the optical axis of the gas cell to achieve optimum alignment of the output collimator facing towards the gas cell; and the collimator holder having an adjustment means operable to achieve angular adjustment of the collimator towards the optical axis of the gas cell and for locking it into a variety of positions. The collimator plate, the input collimator mount, the output collimator mount, and also the collimator holder are of the same design for both the input and the output collimators, and are useable without any restriction either for the input collimator or for the output collimator.

An embodiment of the present invention that incorporates collimators positioned on opposite sides of the gas cell may incorporate two collimator plates that are similar to those discussed in the paragraph above, with the distinction that each collimator plate will incorporate only one collimator mount and one collimator holder thereon. A skilled reader will recognize the possible position options for the collimator mounts on each collimator plate to achieve the optical alignment.

One embodiment of the present invention may incorporate: a closed gas cell module having collimators positioned on the same side of the gas cell, and the gas cell comprising two windows at opposite ends of the gas cell, each window being held in place by gas cell caps, and the gas cell further comprising sensors for temperature and pressure, as well as bellows whereby an input port and an output port integrated in the gas cell are connected to a gas mixture holder, said bellows being operable to minimize the influence of vibration of the monitored gas mixture holder to the optical system on the optics of the apparatus of the present invention. The gas cell module may further incorporate one or more gas cell holders operable to mount the gas cell into a cage system. The cage system may also contain mirror assemblies, collimator assemblies, and a number of rods for linking together all the elements of the high stability optical cage system. The gas cell module may incorporate a front mirror assembly, and further incorporate either: two optical collimators positioned on the same side of the gas cell with a back mirror assembly located on the opposite side of the gas cell; or the input optical collimator and the output optical collimator positioned on opposite sides of the gas cell with a back mirror assembly being positioned on the same side of the gas cell as the output optical collimator. The gas cell module may further incorporate shock and vibration absorber elements, in addition to the bellows.

Embodiments of the present invention may be utilized in particular environments, such as with only a single absorption line of the analyte from a multitude of absorption lines of the analyte. Preferably such use would be with the highest absorption peak. The method and apparatus of the present invention may further be used with a selected absorption single absorption line of the analyte that is unique among all the absorption lines of gas mixture contained in the gas cell, with minimal overlapping with other absorption lines of other gases contained in the gas cell. The tunable laser may be changed for any analyte contained in any gas mixture, while the reference laser and the photodiodes, all other major elements remain the same. In this manner the present invention is thereby easily reconfigurable to achieve specific analyte monitoring. The same measuring module can be used with either a closed gas cell or an open gas cell.

Elements of the present invention can be formed specifically to achieve certain outcomes, for example, the optical layout of the measuring module can consist of beam combiners, beam splitter, beam collimator and the receiving lens. The optical layout of the measuring module can also be comprised of bulk optical elements. As another example, the open gas cell elements can be formed to achieve free space propagation. As an additional example, the input fiber optic collimator can be replaced with a bulk optics collimator. As yet another example, the receiving fiber optic collimator may be replaced with an output telescope positioned close to the bulk collimator, wherein both collimators face a retro-reflector. As still another example, a retro reflector may be used for back reflection of the collimated input beam travelling two times through the free space analyte. As another example, the temperature sensor and the pressure sensor may monitor the respective ambient parameters.

In one embodiment of the present invention, the gas mixture flowing through the gas cell may be generated from an evaporating liquid and be directed by a fan to circulate the vapors through the closed gas cell.

An embodiment of the present invention may be directed monitoring the mass of an analyte in solid phase. The analyte in a solid phase may be converted to a plasma phase and to a gas phase through laser induced breakdown ("LIB") either inside the closed gas cell, or in an open gas cell.

In embodiments of the present invention the elements may vary. For example, embodiments of the present invention may incorporate a single tunable laser or multiple tunable lasers, the wavelength range of the tunable laser or lasers may vary, the wavelength and power of the reference laser may vary, and/or the type of logarithmic amplifier incorporated in photo detection channels may vary. A skilled reader will recognize other possible variations in embodiments of the present invention.

Advantages

The present invention offers several advantages and benefits over the known prior art. In particular, analytes monitoring performed in accordance with the DWAS method of the present invention provides a number of advantages over the prior art. Some of these advantages and benefits of the present invention are discussed herein. A skilled reader will recognize that other advantages and benefits are also possible.

Prior methods, such as TDLAS and CRDS methods, measure the absorption in the gas cell using a photo detected signal at the outlet of the gas cell where gas is expelled, as such absorption is affected by the inherent changes of the tunable laser beam power during wavelength modulation and by the uncontrollable drift in the absorption introduced by optical components and by the photo detection channels. Such prior art methods cannot achieve measuring accuracy at low concentration levels of the analyte. The present invention avoids this disadvantage of the prior art by measuring the absorption inside the gas cell as the ratio between the laser power measured at the output of the gas cell and at the input of the gas cell, at any power, and at any wavelength during the wavelength sweep without additional high frequency wavelength modulation. The absorption measurement is based on the laser beam wavelength and is independent of the laser beam power.

The present invention further avoids inaccuracies due to noise from the optics and from the photo detection channels experienced by prior art methods. The baseline value of the present invention is determined by true absorption measurements across the gas sampling cell at a wavelength generated by a reference laser. There may be a negligible absorption by the analyte and also by the other gasses of the gas mixture contained in the gas sampling cell. The compensated absorption by the analyte is the difference between the absorption measured across the gas sampling cell minus the baseline value. This compensation method of the present invention minimizes the contribution of the noise coming from optics and also from the photo detection channels, and it increases significantly the sensitivity and the accuracy of the analyte concentration measurement that the present invention achieves.

The present invention furthermore avoids other inaccuracies of the prior art by scanning a laser beam having a linewidth that is at least 10,000 times narrower than the absorption linewidth of the analyte. This laser beam is scanned to determine the absorption peak with wavelength accuracy of approximately a 0.01 pm range and with absorption accuracy of approximately a $10 \times 10^6$ range. The present invention thereby avoids the overlapping of narrowly spaced absorption lines that hinders prior art methods.

The present invention offers an advantage over the prior art, in that the present invention can achieve a range of at least six orders of magnitude of dynamic range. The present invention incorporates logarithmic amplifiers for the photo detection channels. The integration of the logarithmic amplifiers with the photo detection channels has the result of providing dynamic range of analyte concentration of six orders of magnitude or more.

The DSWAS method of the present invention involves a measuring volume that is either confined within a closed gas cell, or in a remote area with an open gas cell. The method further involves an interaction between a laser beam and an analyte within the gas cell across an optical path that is of a greater length than the length of the gas cell. Two parallel or virtually parallel mirrors, positioned so that the mirrors are on opposite sides of the outside the gas cell, cause the path of the laser beam to include multiple reflections of the laser beam between the two mirrors, whereby the path of the laser beam incorporates multiple passes through the gas cell. The configuration of the present invention avoids contact between the analyte and the optics. The known prior art does not apply the DSWAS method of monitoring the analyte in a gas cell and therefore cannot produce the measurements and determinations achieved by the present invention.

The present invention incorporates temperature and pressure sensors in both the open gas cell and the closed gas cell. Known prior art does not incorporate temperature and pressure sensors in both open and closed holders of gas mixtures and therefore cannot achieve the determinations of the present invention that utilize the output of the temperature and pressure sensors located in the open or closed gas cell.

The closed gas cell of the present invention can be dismantled for maintenance purposes, assembled and placed again in its previous position with minor adjustments, as required. This ease of removing, cleaning, and repositioning the gas cell within the apparatus is not achievable by the known prior art.

The DSWAS receives measurements and performs determinations relating to a single resonant absorption line of the analyte, that is unique among spectral lines of all components of the gas mixture containing also the analyte. This information is not received as measurements or used in the performance of determinations by known prior art.

A tunable laser source with linewidth that is much narrower than the absorption line of the analyte sweeps the absorption line of the analyte in embodiments of the present invention, without additional modulation for determining the resonant absorption peak and without virtual peak widening, independent of the associated gases existing in the mixture, with wavelength accuracy given by the linewidth of the laser line. Known prior art does not include this element and therefore cannot achieve the accuracy of the determinations of the present invention.

The absorption by the selected line of the analyte is measured at the absorption peak in linear scale as the ratio between the power of a laser beam at the output of the measuring volume and the power of the same laser beam at the input of the measuring volume in embodiments of the present invention, independent of the changes of the laser beam power and of wavelength. In the context of a logarithmic scale, this is the difference between the logarithm of beam power at the output of the measuring volume and the logarithm of the power of the same laser beam at the input of the measuring volume measured at the absorption peak. Thus, the analyte absorption value has insignificant dependence on analyte temperature and pressure. This aspect of the method of the present invention is not applied in the known prior art, and therefore the known prior art cannot achieve the determinations of the present invention.

The wavelength scanning across narrow wavelength interval is fast, in hundreds of microseconds range. Known prior art does not incorporate wavelength scanning at the speed of that of the present invention and thus the known prior art cannot achieve the determinations and output of the monitoring of the present invention.

The disclosed DSWAS can measure multiple analytes belonging to the same gas mixture either by using multiple DFB lasers, or by using a single tunable laser covering multiple absorption lines of the analytes of interest. Known prior art is only operable to measure a single analyte in a gas mixture and therefore a greater number of measurements are achievable by the present invention, and consequently the present invention can produce determinations and output not possible for the known prior art due to multiple analyte measurements that are available to the present invention that are not available to known prior art for the purpose of measurements and output.

A reference wavelength is utilized in the spectral range where there is no significant absorption by the analyte to determine the additive background contribution of the other gases, optics, ambient light and photo detection channels, to the absorption peak. The beam from the narrow band reference laser generating the background wavelength is sent on the same optical path as the beam from the tunable laser, after disabling the tunable laser. Background absorption is measured using the same photo detection channels used for absorption measurement. DSWAS can use multiple background wavelengths. The background wavelength eliminates costly vacuum pump and all associated hardware used by the known prior art to measure the background contribution.

DSWAS is operable to determine true analyte absorption by subtracting the background absorption from the measured peak absorption. Known prior art cannot achieve these operations of the present invention.

DSWAS uses logarithmic amplifiers in the photo detection channels for providing minimum six decades dynamic range of absorption by analyte. Known prior art does not utilize logarithmic amplifiers and therefore cannot achieve the method or apparatus of the present invention.

The optical layout of the disclosed DSWAS can be comprised of either single mode optical fiber, or bulk optical components. This causes the present invention to allow for flexibility of the type of optical layout incorporated in the present invention, which is not a flexibility that known prior art can achieve. This aspect of the present invention may also cause the present invention to be more cost-effective to configure and to operate than known prior art because the present invention may incorporate off-the-self elements.

Additionally, the present invention overcomes disadvantages of the prior art in that the present invention achieves good measurement accuracy. Both a significant number of laser pulses and strong averaging are required to achieve the measurement accuracy of the present invention. Embodiments of the present invention further applies known requirements that can cause very precise control of the cavity in the present invention apparatus, including the following: $0.005°$ C. temperature accuracy; $0.0002$ atm pressure accuracy, for measuring interval between 0 and 1000 ppm with less than 5 s measurement interval (see: Kazuto T., Takamatsu Y., Nanko T., Matsuo J.; "TDLS200 Tunable Diode Laser Gas Analyzer and its Application to Industrial Process"; https://www.yokogawa.com/us/technical-library/white-papers/tdls200-tunable-diode-laser-gas-analyzer-and-its-application-to-industrial-process.htm).

A. Configurations of the Present Invention

The embodiments of the present invention function to incorporate resonant absorption of a laser beam propagating into a gas mixture containing the analyte with discrete absorption lines. The terms "maximum absorption" and "minimum transmission" are utilized interchangeably herein, and are applied in accordance with the context of the discussion herein.

In the following description of the embodiments, reference is made to accompanying drawings. Such drawings form a part hereof and show by way of illustration specific embodiments of the invention. A skilled reader will recognize that there are other embodiments of the present invention not shown in the drawings, and that structural, logical, optical, mechanical and electrical changes may be made to the present invention without departing from the spirit and the scope of the present invention.

One purpose of the present invention is to be used to monitor the content of an analyte such as water within a natural gas mixture. The invention may be utilized in natural gas industry and oil industry, but it is not limited to water only. The elements disclosed in the present invention can be used also in space explorations, environmental and natural resources monitoring, health care as well as in any industry requiring very sensitive, very accurate cost effective instrumentation for monitoring analytes.

The Figures are discussed herein with reference to particular elements having specific attributes, however, a skilled reader will recognize that the elements and the attributes of the elements may vary in embodiments of the present invention.

FIG. 1 shows an example of a prior art apparatus for measuring moisture in natural gas or an analyte in a gas mixture. This prior art is shown in accordance with the invention disclosed in U.S. Pat. No. 8,547,554 issued to the General Electric Company on Oct. 1, 2013. The prior art applies harmonic spectroscopy methods to detect moisture in natural gas and analytes in gas mixtures. A tunable laser 2 emits light 4 that is of a narrow bandwidth and is centered on a specific wavelength. The wavelength can be changed to cover a spectral range that is greater than the absorption linewidth of the analyte. Laser light 4 is collimated by the optical element 6, and transmitted through the optical window 18 into the gas sampling cell 20, where is reflected by the mirror 24 towards the photo detector 26. A beam splitter 30 directs part of the incident laser beam towards the photo detector 28. The photo detector monitors the power of the beam generated by the tunable laser 2, or measures the concentration of analyte leaking into the chamber 22. The gas cell 20 has an inlet 32 connected to a gas entrance 36 whereby gas enters the chamber, and an outlet 34 connected to a gas exit 36 whereby gas exits the chamber. The elements 37 and 38 control the gas pressure within the gas cell 20. The pressure sensor 40 and the temperature sensor 42 send signals proportional with their input parameters to the electronic circuitry 44, which may contain one or more processors, microprocessors or similar subassembly for controlling the operation of the entire monitoring unit. The electronic circuitry 44 commands the laser driver 46 and receives the signals from the photo detectors 26 and 28 for computing the analyte concentration in the gas cell 20. The electronic circuitry 44 also has a digital input-output peripheral 50, an input device 54 and a display 52. This prior art cannot achieve the accuracy of the measurements of the present invention.

Figure 2:
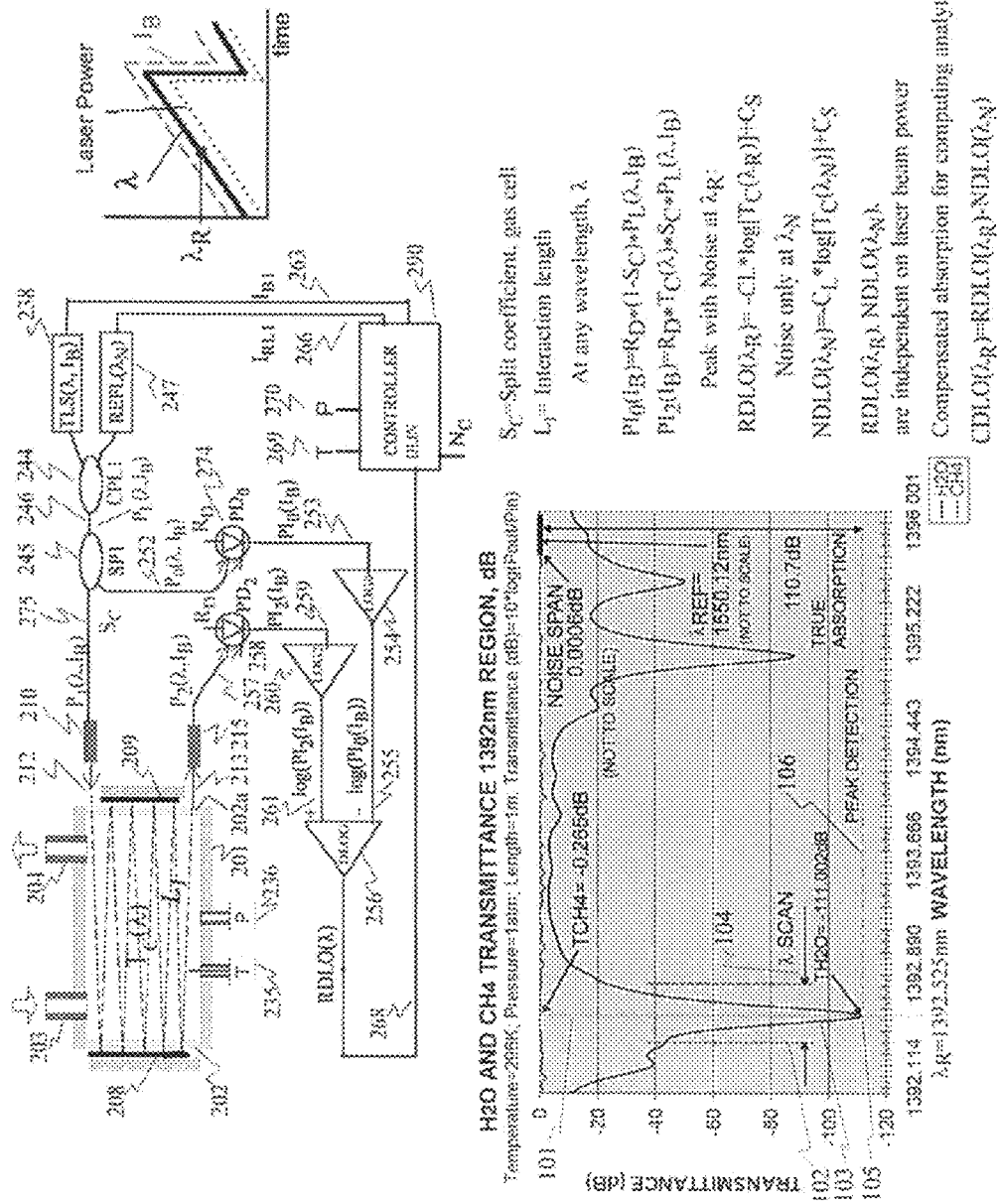
FIG. 2 is a schematic drawing of an embodiment of the apparatus of the present invention and a graph chart.

FIG. 2 shows a simplified schematic of an embodiment of the present invention. FIG. 2 is provided to facilitate easy understanding of the principles of the invention. Additional schematics and descriptions of embodiments of the present invention incorporate elements that are not shown in FIG. 2. The elements of embodiments of the present invention are generally operable to perform a variety of tasks in accordance with the basic overriding operating principles applicable to FIG. 2.

A gas cell 201 contains an analyte in a gas phase. A collimated laser beam 212 incident in the gas cell at a small angle (for example, such as an angle that is less than 1 degree) with the axis of the gas cell, is reflected multiple times between the reflective surfaces 208 and 209. The collimated laser beam passes through the gas cell one or more times, in accordance with the path of the direction of the laser beam and any reflections of the beam. After multiple reflections, the laser beam passes out of the gas cell as the beam 213. For example, the laser beam may pass out of the gas cell at a location that is beyond the edge of the reflective surface 209, so that the beam is not reflected back into the gas cell once it passes out of the gas cell at this specific point. The beam 213 provides the interaction length $L_I$ between the light beam and the analyte. The interaction length of the laser beam is greater than the length of the gas cell, in accordance with equation (1).

One embodiment of this invention measures the absorption of the laser beam by the analyte. The absorption is measured as the ratio between the laser beam power $P_2(\lambda,I_B)$ at the output of the gas cell 215 and the laser beam power $P_1(\lambda,I_B)$ at the input of the gas cell 210 independent of laser beam power. The splitter $SP_1$ provides the reference power $P_0(\lambda,I_B)$. The reference power is a fraction of $P_1(\lambda,I_B)$ at any wavelength and laser beam power. The photodiode $PD_2$ generates the absorption dependent photocurrent $PI_2(I_B)$ in a manner whereby the absorption dependent photocurrent is proportional with the output power $P_2(\lambda,I_B)$. The logarithmic amplifier 260 converts the photocurrent $PI_2(I_B)$ to voltage. The photodiode $PD_0$ generates the reference photocurrent $PI_0(I_B)$ in a manner whereby the reference photocurrent is proportional with the input power $P_1(\lambda,I_B)$ incident in the gas cell. The logarithmic amplifier 254 converts to voltage the photocurrent $P_0(\lambda,I_B)$. The linear DLOG differential amplifier 256 determines the difference between the outputs of the logarithmic amplifiers 260 and 254, producing at its output RDLO($\lambda$) voltage 268. The output RDLO($\lambda$) voltage is proportional with the transmittance through the gas cell independent of laser beam power. This is the ratiometric aspect of the method of the present invention.

As shown in the graph incorporated in FIG. 2 showing $H_2O$ and $CH_4$ transmittance in 1392 nm Region, in dB, the laser wavelength 101 produced by and directed from the tunable laser 238 is swept across the spectral interval 102 that incorporates the absorption line 103 of the analyte. The spectral interval may be of varying widths, for example, such as between 10 pm and 100 pm wide, and the width is indicated as $\lambda$ SCAN 104. The laser wavelength may be of various linewidths, for example, such as a linewidth that can be between 0.004 pm and 0.1 pm. During the wavelength sweep, the laser wavelength $\lambda_R$ corresponds to the resonant absorption peak or transmission dip 105 of the analyte. The resonant absorption peak or transmission dip of the analyte is the peak or dip where the analyte exhibits maximum absorption 106. At $\lambda_R$, the output 268 of the DLOG differential amplifier 256 gives RDLO($\lambda_R$) expressed by the equation (12), also containing the background noise. To measure the background noise, the tunable laser 238 is turned off. The laser 247 is turned on generating $\lambda_N$, into a spectral region where the analyte has negligible absorption. An example of this is shown in the $H_2O+CH_4$ Transmittance 1545 nm-1555 nm, dB graph of FIG. 9c. At $\lambda_N$, the output 268 of the DLOG differential amplifier 256 generates NLDO ($\lambda_N$) proportional with the background noise. The compensated absorption of the analyte CLDO($\lambda_R$) as in equation (15) is used to calculate the compensated mass of the analyte as given by the equation (16).

Figure 3A:
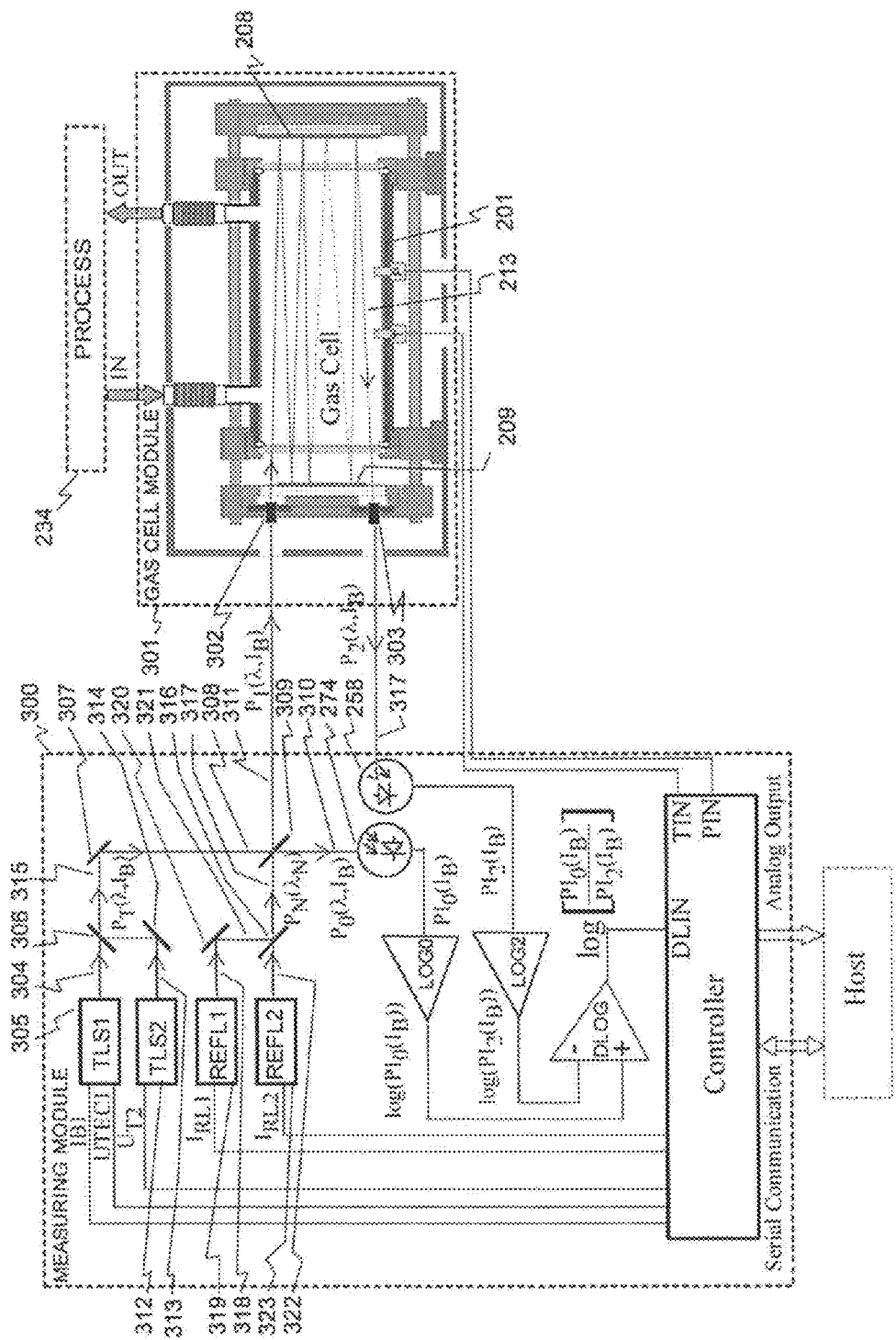
FIG. 3a is a schematic drawing of an embodiment of the apparatus of the present invention wherein the measuring module has an optical layout with bulk optical elements.
Figure 3B:
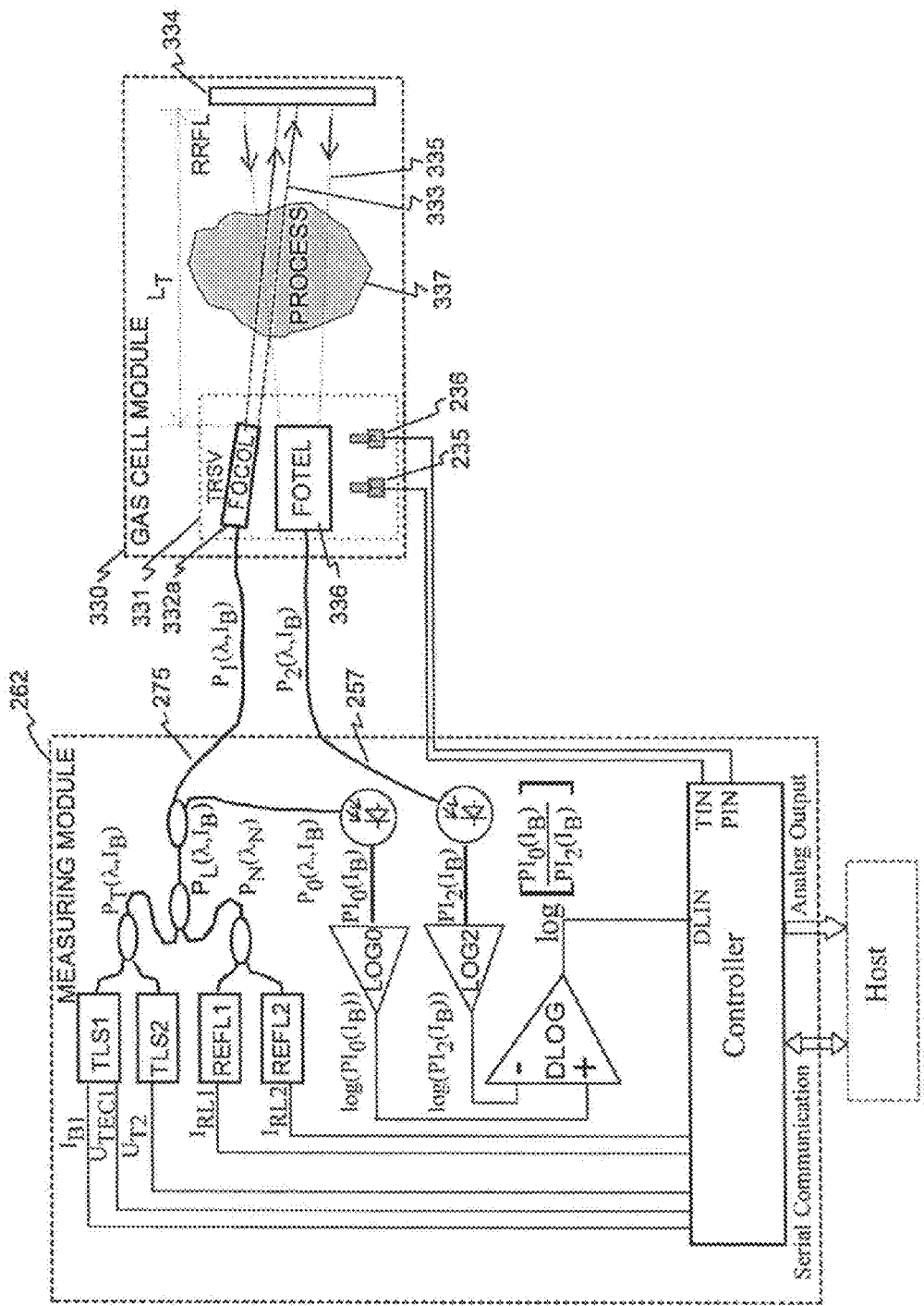
FIG. 3b is a schematic drawing of an embodiment of the apparatus of the present invention, wherein the optical layout of the measuring module has fiber optic elements.
Figure 3C:
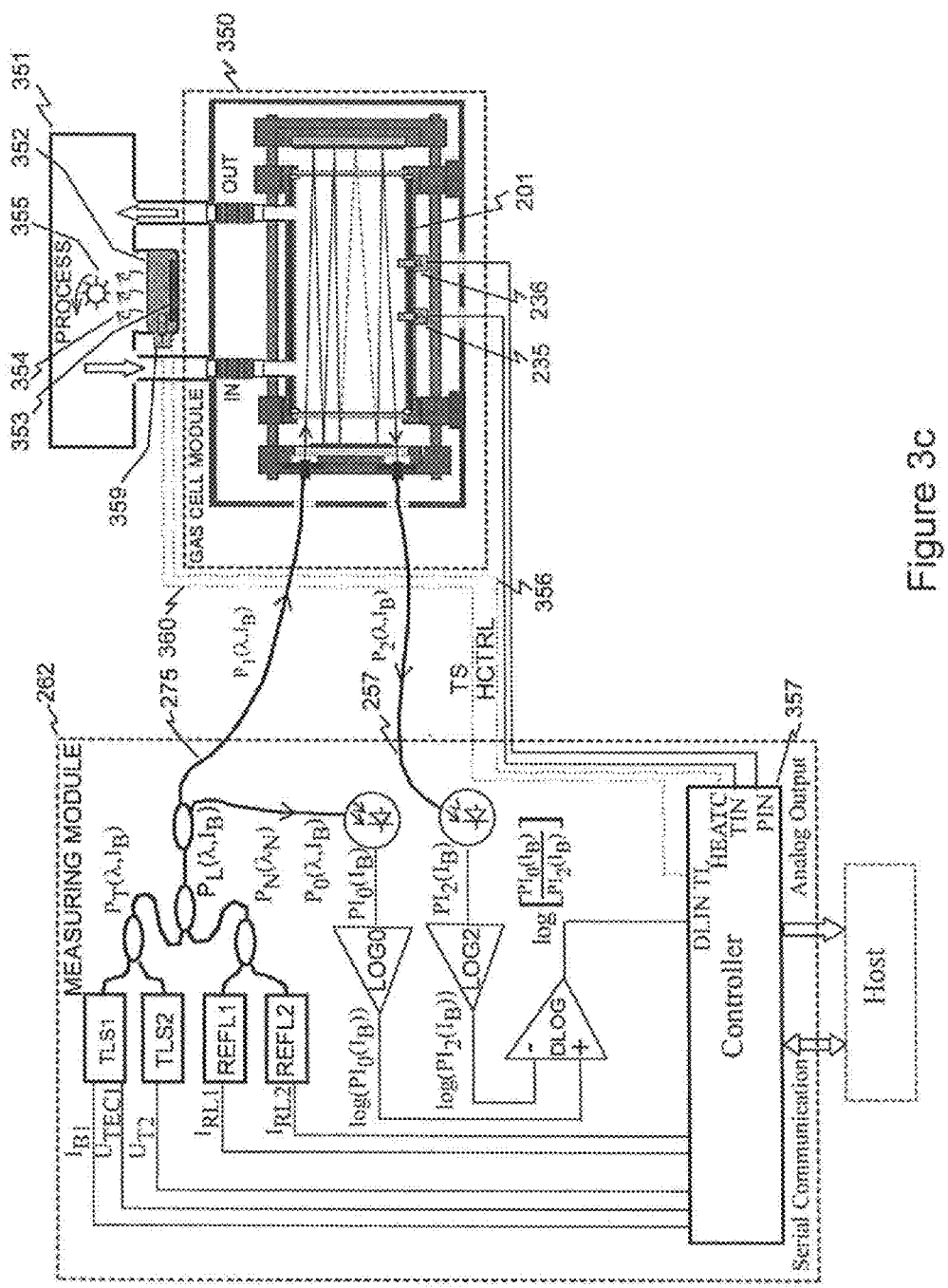
FIG. 3c is a schematic drawing of an embodiment of the apparatus of the present invention, wherein the measuring module has the optical layout built with fiber optic elements.
Figure 3D:
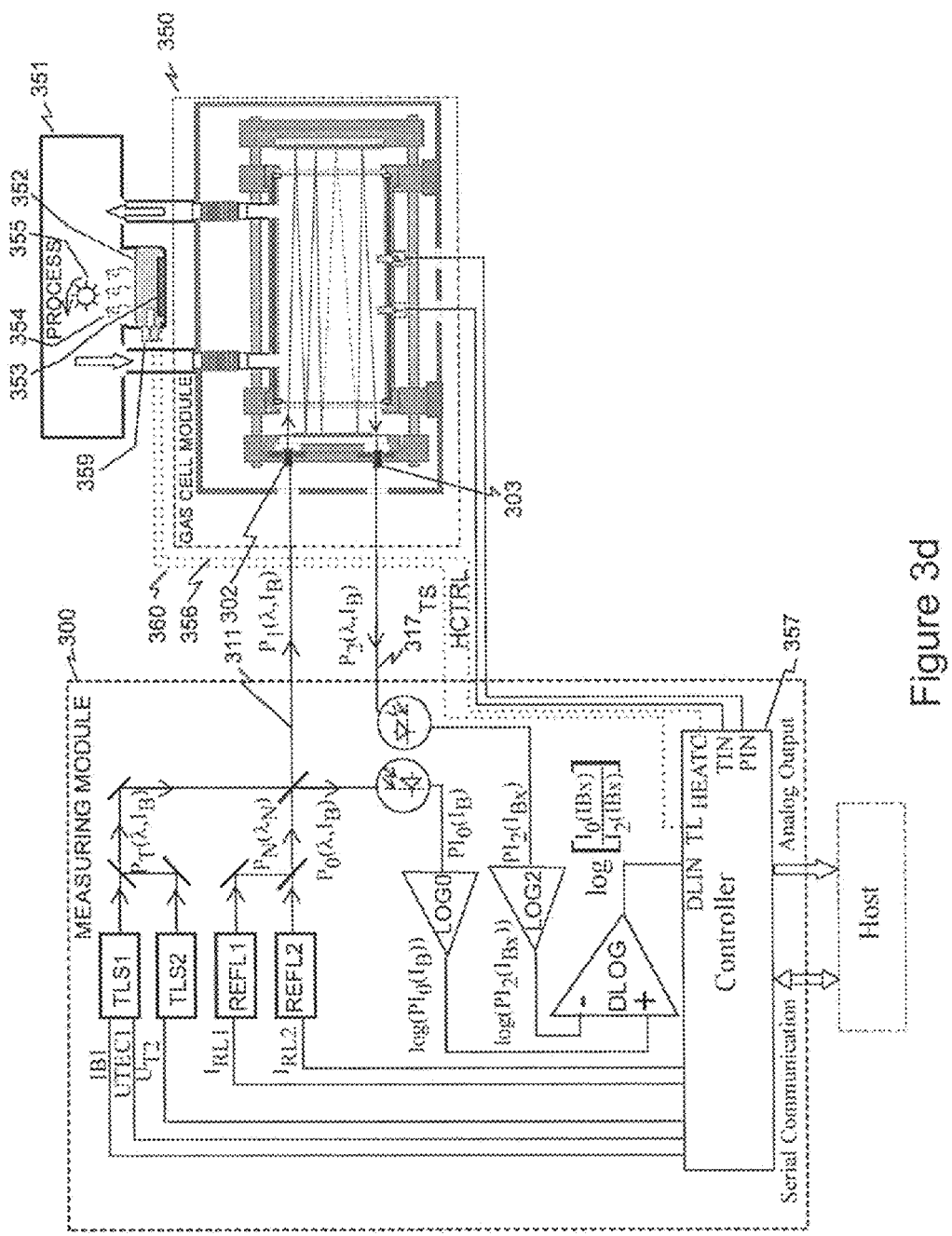
FIG. 3d is a schematic drawing of an embodiment of the apparatus of the present invention, wherein the measuring module is built with bulk optical elements.
Figure 3E:
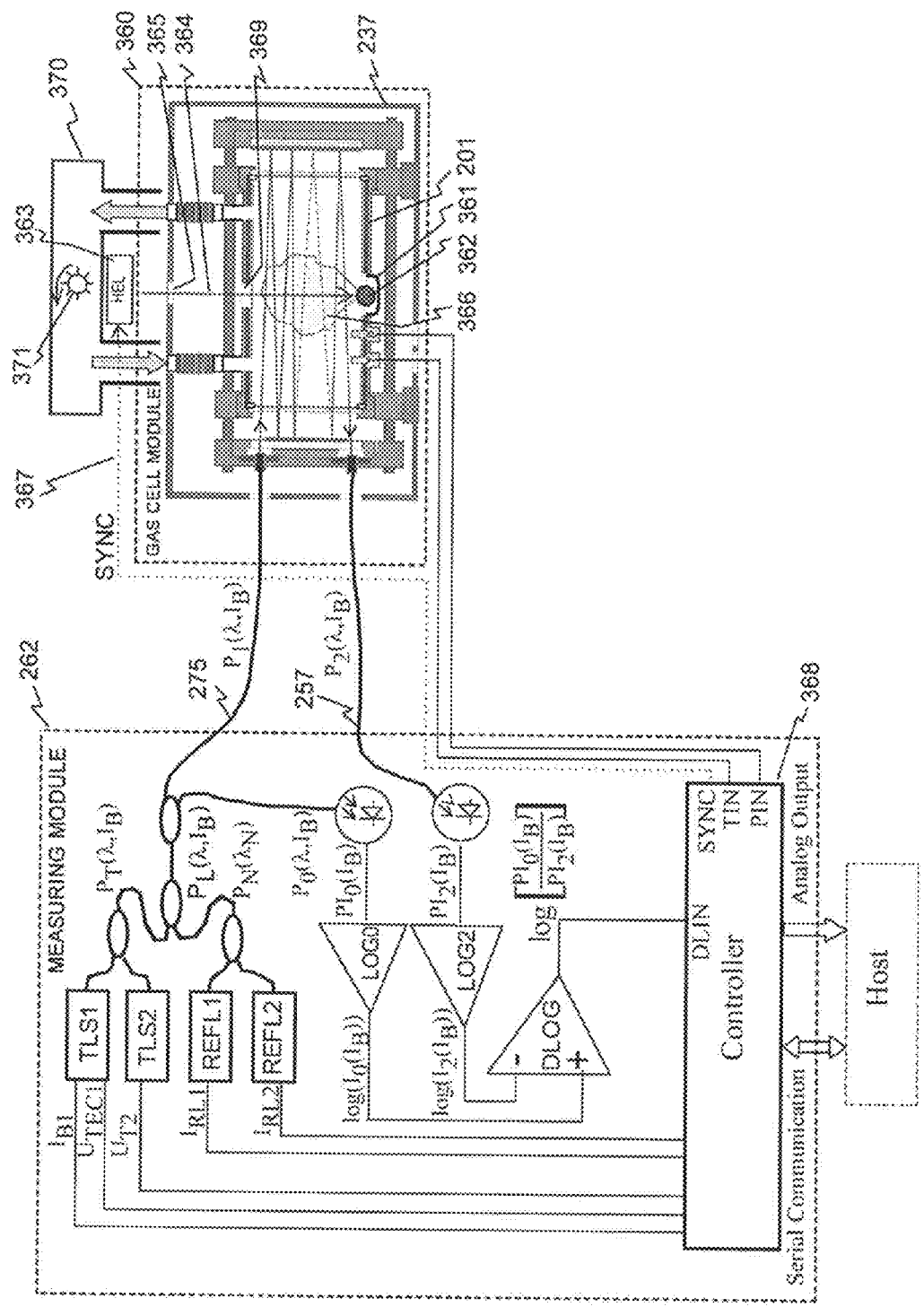
FIG. 3e is a schematic drawing of an embodiment of the apparatus of the present invention, wherein the measuring module is built with fiber optic elements.
Figure 3F:
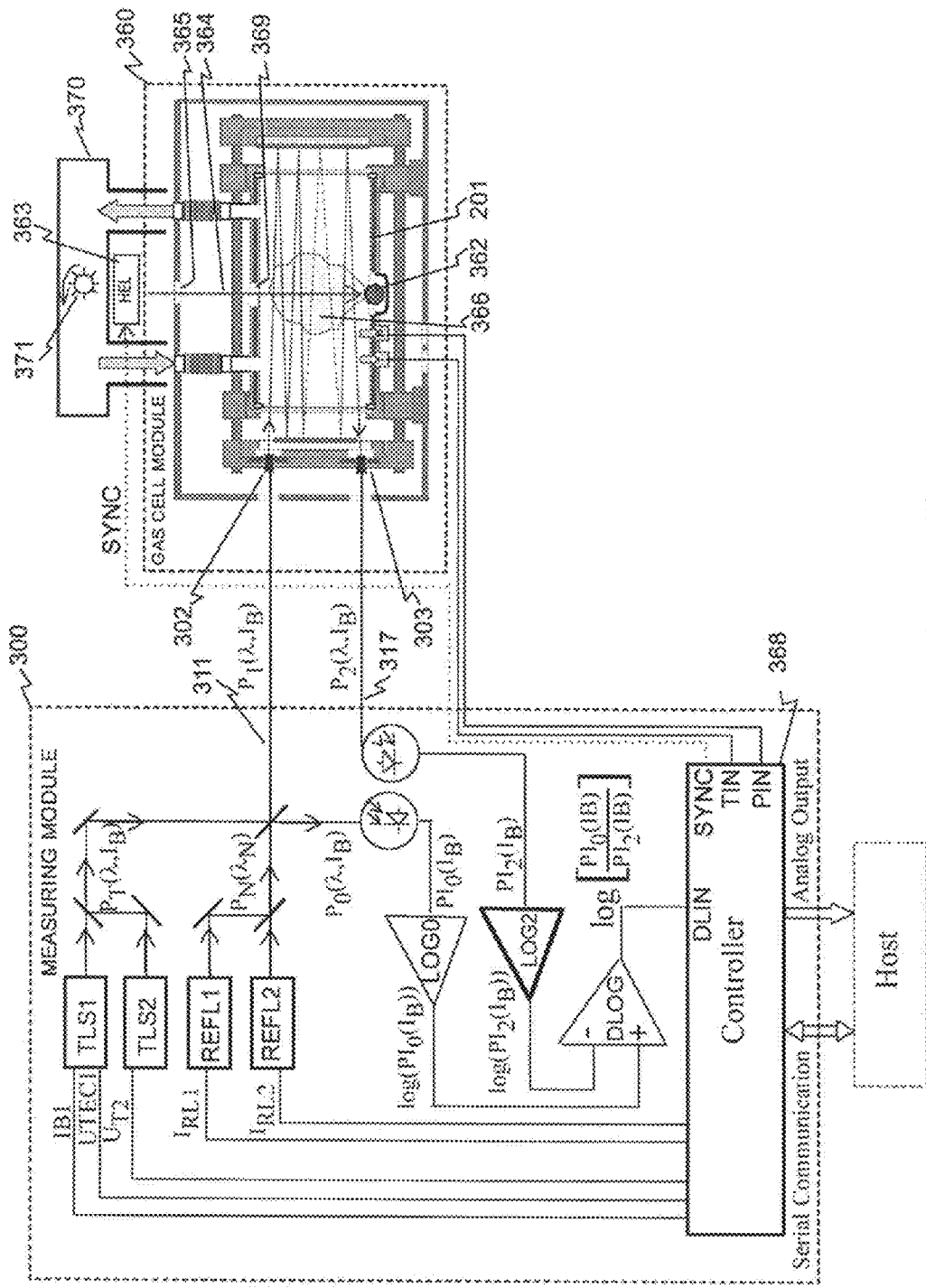
FIG. 3f is a schematic drawing of an embodiment of the apparatus of the present invention, wherein the measuring module is built with bulk optical elements.
Figure 3G:
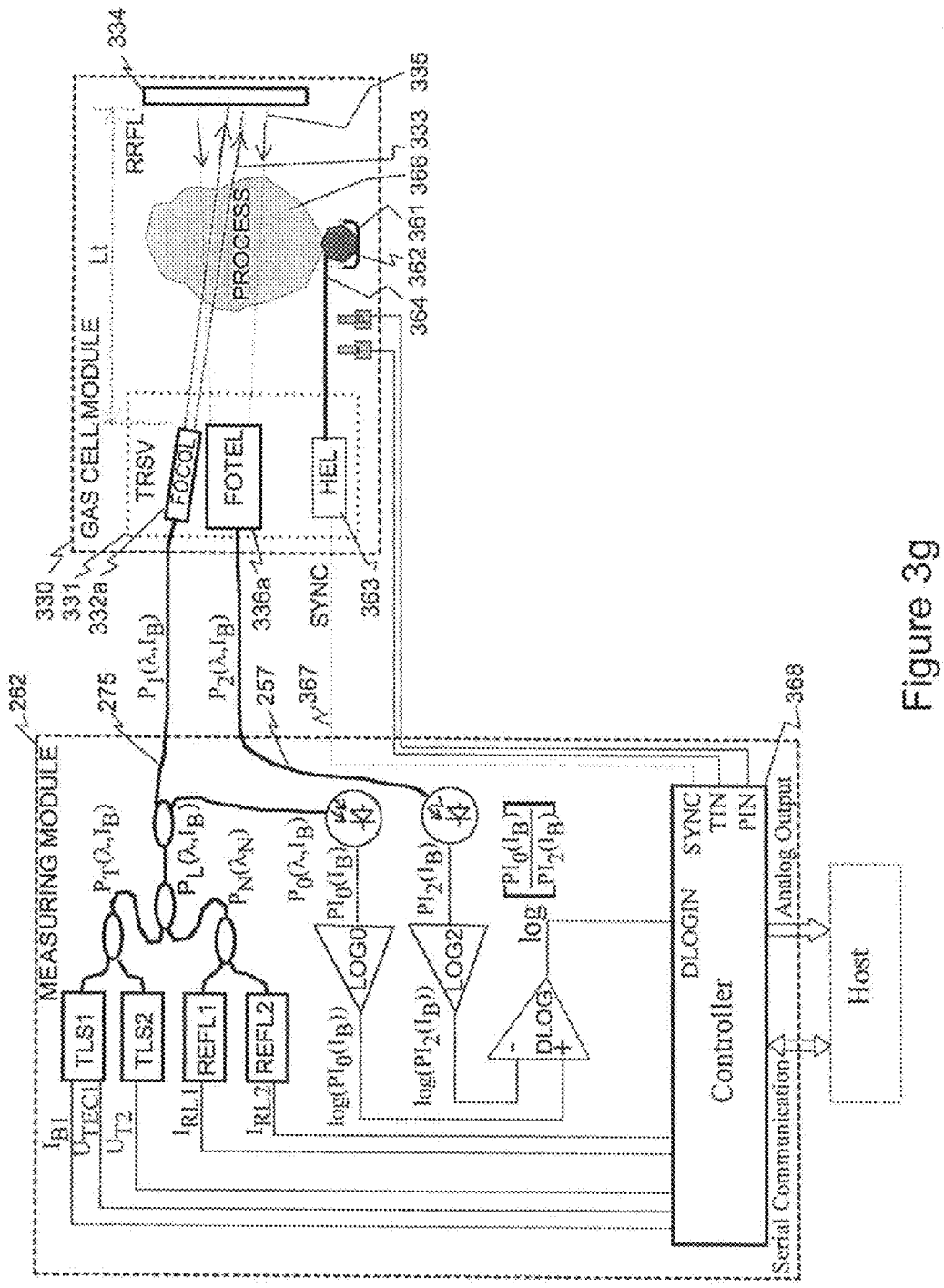
FIG. 3g is a schematic drawing of an embodiment of the apparatus of the present invention, wherein the measuring module is built with fiber optic elements.
Figure 3H:
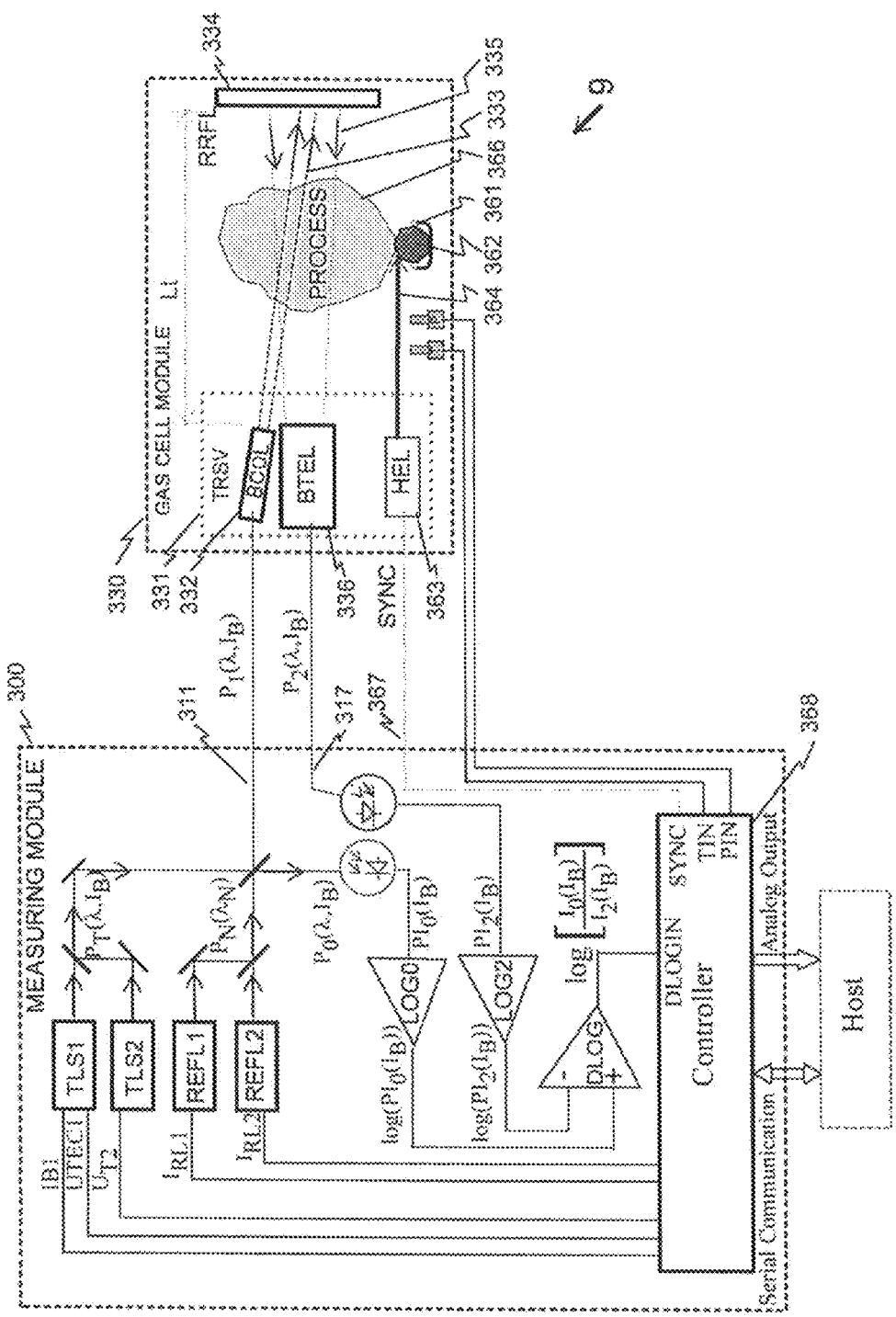
FIG. 3h is a schematic drawing of an embodiment of the apparatus of the present invention, wherein the measuring module is built with bulk optical elements.
Figure 3I:
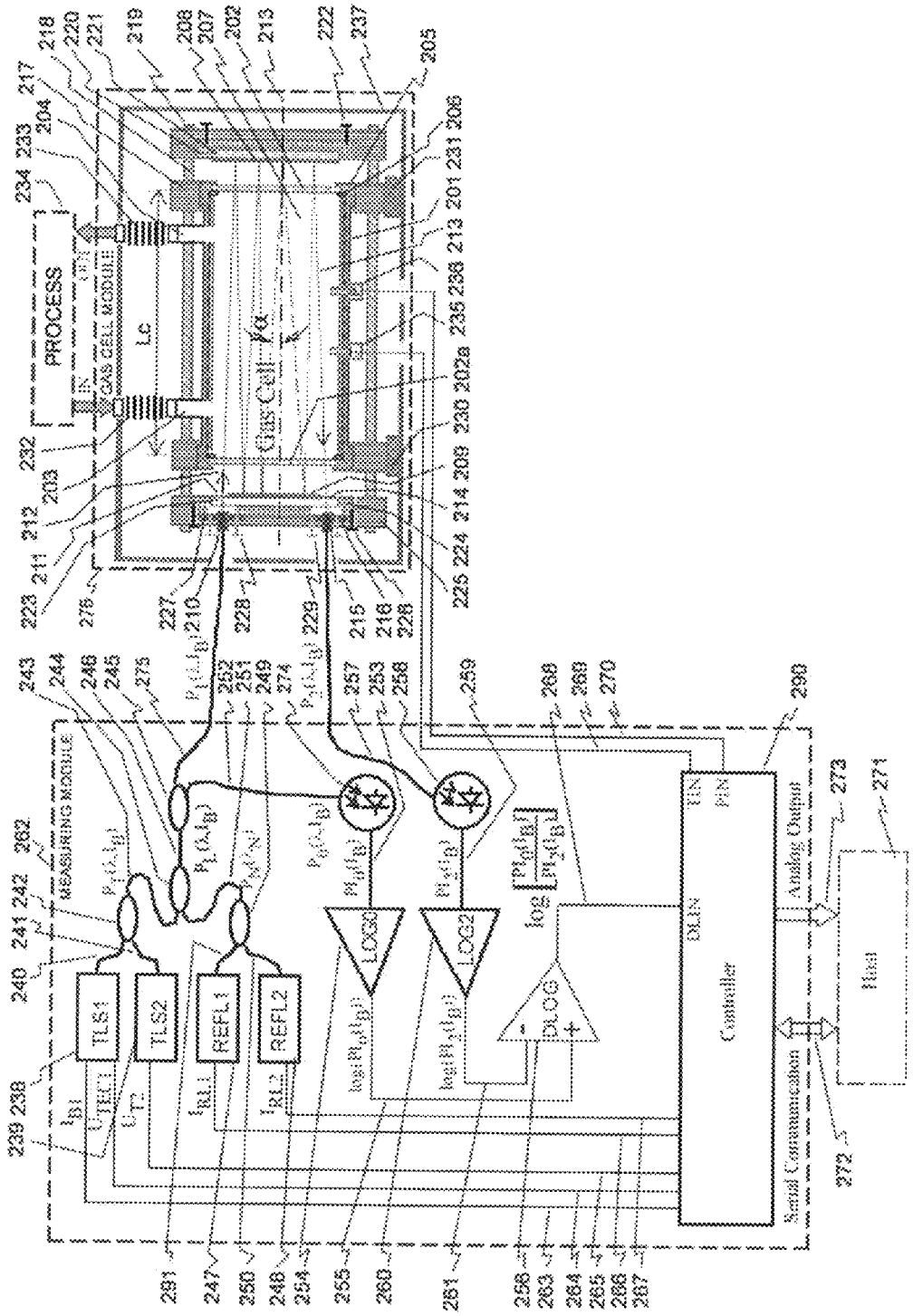
FIG. 3i is a schematic drawing of an embodiment of the apparatus of the present invention.

FIG. 3i is a schematic drawing of an embodiment of the apparatus of the present invention. In FIG. 3i the major modules of the apparatus, for example, such as the measuring module and the gas cell module, are delimited by dashed lines. The measuring module of the embodiment of the present invention shown in FIG. 3i incorporates an optical layout comprising a fiber optic configuration. The gas cell unit shown in FIG. 3i comprises a closed cell configuration with fiber optics input and output ports.

The apparatus 1 of the present invention, as shown in FIG. 3i, incorporates a gas cell 201 formed primarily of a corrosion resistant stainless steel tube having windows 202 attached at each end. The gas cell defines en enclosure that facilitates the measurement of an analyte. For example, the analyte may be water in gas phase in standard conditions, such as, for example at 25° C. and 100 kPa (see: National Bureau of Standards (NBS) (1982). "Table of Chemical Thermodynamic Properties". *Journal of Physics and Chemical Reference Data* 11 (Supplement 2)). The gas cell incorporates a gas intake port 203 and a gas exhaust port 204 that function to cause the analyte to flow through the gas cell. Each window 202 is mounted on the body of the gas cell. For example, each window may be mounted by a means, such as a cell cap 205. A gasket 206 may further be utilized in the mounting means for sealing purposes. Each cell cap 205 may be rigidly mounted in a cap holder 217. Embodiments of the present invention may incorporate multiple cap holders. For example, the embodiment of the invention shown in FIG. 3*i* incorporates two cap holders 217.

In embodiments of the present invention the cap holders may integrate with one or more rods to form the core of a cage system 219. For example, as shown in FIG. 3*i*, the cap holders may integrate with four rods 218. A skilled reader will recognize that a variety of cage system configurations may be incorporated in the present invention. For example, a cage system that may be purchased off the shelf, such as the 60 mm cage system available from Thorlabs (see: Thorlabs Cage Systems, http://www.thorlabs.com/navigation.cfm?guide_id=2002), may be utilized in the present invention. The cage system incorporated in embodiments of the present invention may be a customized cage system. The cage system is generally formed to provide several advantages, for example, such as mechanical stability and modularity.

The body of the gas cell 201 and the windows 202 and 202*a* therein delimit the measuring volume 207 of the gas cell. The analyte is contained within the gas cell and is thereby prevented from coming into contact with either of the reflective layers 208 and 209. The reflective layers may be low loss, and highly reflective layers. The reflective layers may be positioned parallel from each other, on opposite sides of the gas cell. The gas cell further prevents the analyte from contacting any optical elements of the apparatus.

A hack mirror mount 220 may be incorporated in the present invention to hold the back flat mirror substrate 221 that incorporates the low loss high reflective layer 208. In one embodiment of the present invention, the flat, high reflective layer 208 covers the entire working area of the flat substrate 221. This configuration of the combination of the reflective layer 209 and the flat substrate 221 is shown in FIGS. 2 and 5*c*. Screw elements 222 may be incorporated in the present invention to achieve optical alignment of the reflective layer 208. The optical alignment of the reflective layer 208 may achieve the multiple reflections of the incident beam 212 that cause the path of the incident beam to include multiple instances of the incident beam passing inside the closed gas cell. Pull screws 226 and push screws 604 shown in FIG. 6 may be incorporated in the present invention to be operable to achieve the alignment of the reflective layer 208. The alignment procedure applied to the use of the pull screws and push screws may be a procedure that is well known by persons skilled in the art of the present invention.

Figure 5A:
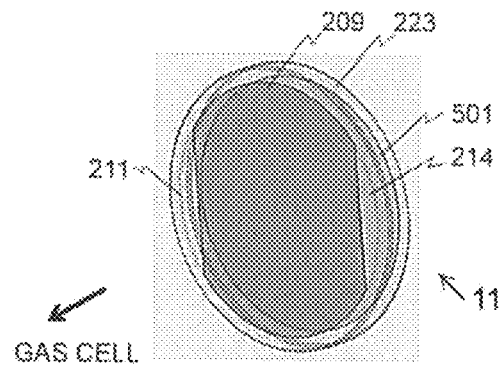
FIG. 5a is a perspective cross-section of an embodiment of the front mirror of the closed gas cell of the apparatus of the present invention.
Figure 6:
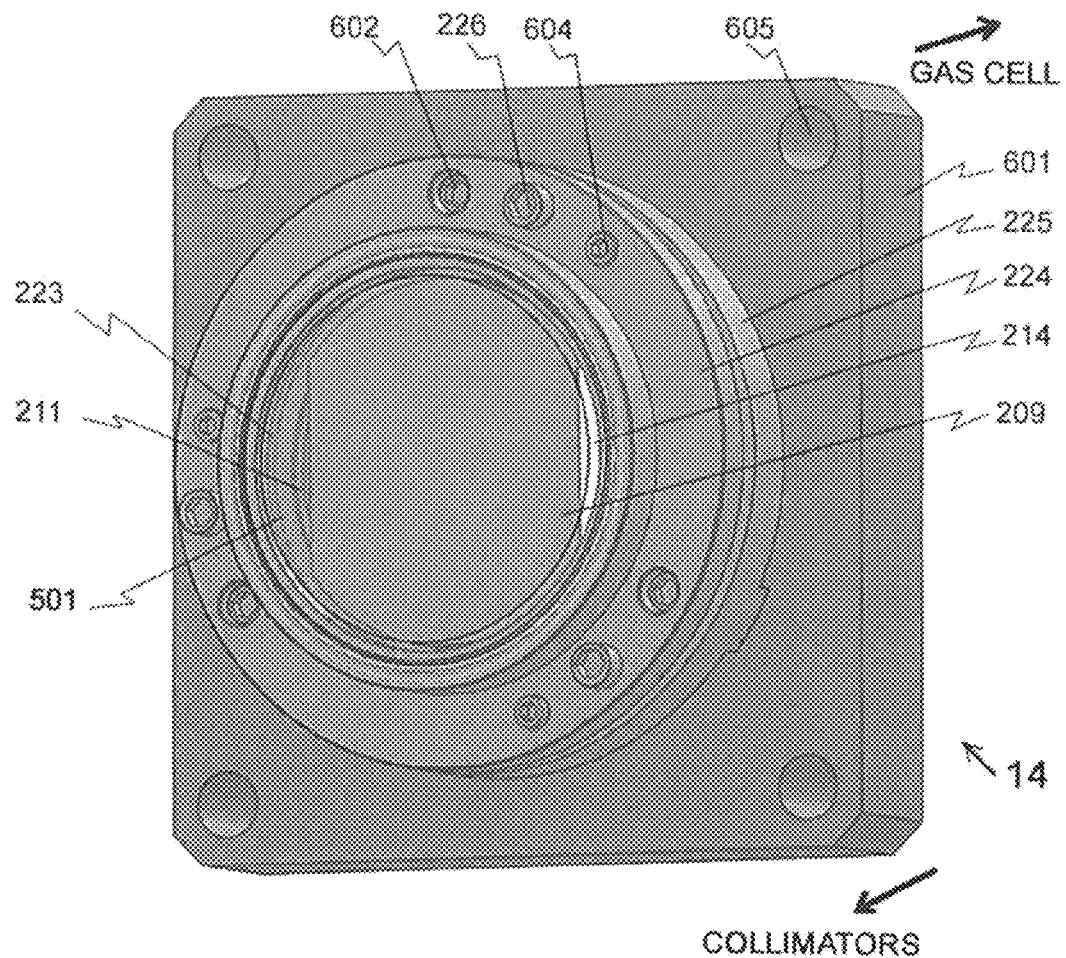
FIG. 6 is a side view of an embodiment of the front mirror assembly of the apparatus of the present invention.

The substrate 223 of the front mirror, as shown in FIG. 2 and FIG. 5*a*, incorporates on its front facing side highly transparent input optical ports 211 and 214 and a highly reflective low loss layer 209. The substrate 223 may be held rigidly in a particular position by the mirror holder 224, as shown in FIGS. 3*i* and 6. The mirror holder may be attached to the mirror mount 225 and to the mirror plate 601, as shown in FIG. 6. The mirror plate may be mounted in the cage system 219. For example, the mirror plate may be mounted to the cage system by way of one or more rods of the cage system passing through one or more holes 605 in the mirror plate, as shown in FIG. 6.

Pull screws and push screws may be utilized to achieve angular alignment of the reflective layer 209, and to lock the reflective layer in a specific position. For example, as shown in FIG. 6, three pairs of pull screws 226 and of push screws 604 may be incorporated in the present invention and be operable to achieve angular alignment and locking in position of the front reflective layer 209. The positioning of the reflective layer 209 may be such that the position of the reflective layer 209 causes the incident beam to achieve a path that includes multiple passes inside the gas cell. The present invention may further incorporate screws operable to shift and lock the mirror mount. For example, as shown in FIG. 6, three screws 602 may be operable to shift and lock in place the mirror mount 225 in a position towards the front mirror plate 601. The alignment procedure applied to the front substrate 223 may be a procedure that is well known by persons skilled in the art of the present invention.

Figure 7:
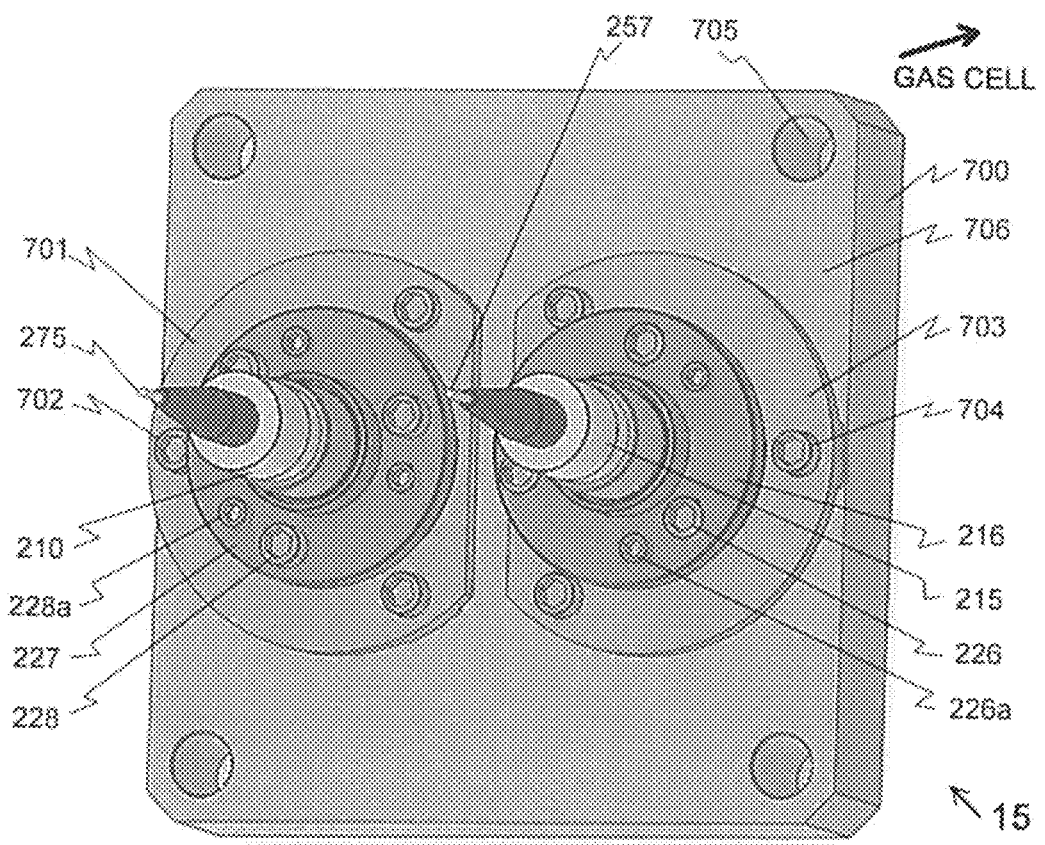
FIG. 7 is a side view of an embodiment of the collimators assembly of the apparatus of the present invention.

The input light beam 212 is generated and directed from an input fiber optic collimator 210. The collimator may be mounted in the input fiber collimator holder 227. The mounting means whereby the collimator is mounted so as to be incorporated in the present invention may incorporate pull screws 228, 229 and with push screws 228*a* operable to achieve angular alignment of the input fiber optic collimator 210 and to lock the collimator in a specific position on the collimator mount 701. An example of the mounting means for a collimator in an embodiment of the present invention is shown in FIG. 7, wherein screws 702 may be operable to translate the collimator mount 701 on the face 706 of the collimator plate 700. The screws 702 may further be operable to lock the collimator mount 701 in a particular position chosen by a user. An alignment procedure that is well known to persons skilled in the art may be applied to align the input fiber collimator in embodiments of the present invention.

The input fiber optic collimator 210 sends a collimated input light beam 212 through the input optical port 211. The light beam 212 may be directed through the gap between the parallel reflective layers 208 and 209. The light beam may be directed at a small incident angle α with respect to the axis 213 of the gas cell. For example, the incident angle may be between 0.1° and 1.5°, or may be another angle. The incident beam 212 may be reflected multiple times by each reflective layer 208 and 209. The reflections of the incident beam may cause the path of the incident beam to pass through the gas cell between the reflective layers 208 and 209 one or more times. The number of passes through the inside of the gas cell that the path of the incident beam incorporates is directly related to the incident angle α. The beam 212 is directed from the input optical port 211 and reflects between the reflective layers 208 and 209 until it passes through the output optical port 214 and is thereby rendered an output beam 213. The output beam is collected by the output fiber optic collimator 215.

The collimator may be incorporated in the present invention through a connection to a collimator holder 216. The collimator holder may be solidly attached to a collimator mount 703, for example, such as by way of an attachment means that incorporates one or more pull screws 226 and push screws 226*a*, for example, such as three pair of pull screws and push screws, as shown in FIG. 7. The attachment means may be operable to achieve optical alignment of the output fiber optic collimator 215 and to lock the collimator in a particular position, as chosen by the user. An output fiber collimator mount 703 may be attached to a collimator plate 700 with the mounting screws 704. The mounting screws may also be used also to lock the mount 703 in a particular position, as shown in FIG. 7. An alignment procedure that is well known to persons skilled in the art may be applied to align the output collimator in embodiments of the present invention.

The total interaction length $L_I$ between the light beam and the analyte inside the gas cell is:

$$L_I = N_T \cdot L_C \qquad (1)$$

where $L_C$ is the gas cell interior length defined by the spacing between the windows 202 and 202*a*, and $N_T$ is the number of passes of the optical beam inside the gas cell. In one embodiment of the present invention, $L_I$ can be adjusted within large limits by selecting the length $L_C$ and also by changing the number of passes $N_T$ by choosing the incidence angle α. The interaction length $L_I$=10 m can be achieved easily with $L_C$=250 mm and $N_T$=40 beam trips for an inside cell diameter of 38 mm.

The shock and vibration absorbers 230 and 231 and the bellows 232 and 233 may be operable to minimize the influence of the external mechanical actions upon the optical elements mounted inside the cage system 219. In embodiments of the present invention a rigid housing 237 may be incorporated in the present invention and be operable to protect mechanically the entirety of the gas cell module 276.

The gas mixture holder 234 can be of a variety of forms and configurations, for example, such as a pipeline carrying a gas mixture containing the analyte whereby the gas cell 201 is operable as a bypass and a portion of the gas mixture flowing through the pipeline is diverted into the gas cell. As another example, the gas mixture holder may be a container with a gas mixture that contains the analyte therein.

The term "process" can also be used to describe the gas mixture holder that can be incorporated in embodiments of the present invention. The term "gas mixture holder" is utilized herein for clarity to distinguish between the container from which the gas mixture is provided and otherwise introduced to the gas cell from any reference to processes, methods and functions of the present invention. The gas mixture holder may be a container, or may be an access means to a gas mixture, such as a pipeline, a valve or pipe extending from a pipeline, or any other object wherein a gas mixture may be contained or the flow of a gas mixture may be accessible so that the gas mixture may ultimately be directed into the gas cell.

Embodiments of the present invention may be utilized with virtually any gas mixture containing any analyte, providing that the windows 202 are transparent in the wavelength range containing at least the required absorption line of the analyte and that the windows are also chemically resistant to the corrosive action of the gas mixture containing the analyte. Technologies available today provide a wide choice of optical materials for gas cell windows for satisfying the requirements, for example, such as fused silica, sapphire, N-BK7, or other optical materials.

If the analyte is normally in liquid phase either single or embedded into a liquid matter, it will be brought to gas phase by evaporation, as is described herein. If the analyte is normally in solid form either single or embedded into a solid matter, the entire matter including the analyte will be brought to plasma phase or to vapor phase by using laser induced breakdown or LIB, and the analyte will be monitored using one of its absorption lines in plasma phase or in vapor phase as is described herein. For the purpose of providing an example of the function of the apparatus of the present invention and the method and system of the present invention, references are made herein to water as the analyte component of a natural gas mixture. However, a skilled reader will recognize that these references are for example purposes only. The present invention is operable with water analyte present in natural gas, but is further operable to monitor any analyte in gas phase embedded in any gas mixture in gas phase independent of the spectral range.

A temperature sensor 235 and a pressure sensor 236 may be integrated with the gas cell. The temperature sensor may be operable to measure the temperature of the gas mixture within the gas cell. The pressure sensor may be operable to measure the pressure of the gas mixture within the gas cell.

As shown in FIG. 3*i*, the measuring module 262 contains a continuous wave tunable laser source 238, referenced herein as the first tunable laser source ("TLS1"). The TSL1 may incorporate a distributed feedback ("DFB") laser (see: Eblana Photonics EP1854-DM laser series http://www.e-blanaphotonics.com/EP1854-DM-Series.php), and may be tunable across 2 nm range around 1847.104 nm, having a very narrow linewidth of about 2 MHz or 0.016 pm. TLS1 can be a variety of types of lasers, for example, such as a continuous wave tunable cascade laser, an external cavity tunable solid state laser, or another type of tunable laser. The measuring module can also incorporate an additional tunable laser source 239, referenced herein as the second tunable laser source ("TLS2"). The TSL2 may incorporate an optical amplifier and an optical filter, tunable across 40 nm wavelength interval or more with of 15 MHz or 0.06 pm linewidth (see: Miron N., "Tunable laser with tilted-mirrors interferometer and dynamic wavelength reference", *Proc. of SPIE*, 7195, 71952J-1-71952J-12, (2009)). TLS2 can be a variety of types of lasers, for example, such as a continuous wave tunable cascade laser, an external cavity tunable solid state laser, or another type of tunable laser.

For monitoring of a water analyte, only TLS1 may be required. TLS2 may be used for monitoring other analytes such as carbon dioxide, hydrogen sulfide and methane. The same monitoring unit can be utilized with TLS1 and TLS2. The output of TLS1 is delivered through the single mode optical fiber 240 to one input of the 50/50, 2×1 fiber optic combiner 242. The output of TLS2 is delivered through the single mode optical fiber 241 to the other input of the same 50/50 2×1 fiber optic combiner 242. The output 243 of the 2×1 fiber optic combiner 242 carrying the optical beam with tunable wavelength having $P_T(\lambda, I_B)$ optical power emitted by any active tunable laser is sent to the 50/50, 2×1 combiner 244 through the single mode optical fiber 243.

The reference laser ("REFL1") 247 emits a reference beam. The reference beam may be emitted with stabilized wavelength $\lambda_N$ through the single mode optical fiber 291 at one input of the 50/50, 2×1 fiber optic combiner 249. From the output 251 of the combiner 249, the reference beam with reference optical power $P_N(\lambda_N)$ enters the other input of the combiner 244 and exits the combiner through the output of the combiner 244. The reference beam may follow an optical path that is identical or virtually identical to the tunable wavelength optical beam described previously herein.

The wavelength $\lambda_N$ belongs to a spectral interval with very insignificant absorption by the analyte and also by all the other gases of the gas mixture containing the analyte. The wavelength $\lambda_N$ may be used for measuring the optical background noise. The background noise may be introduced by all optical components of the optical setup as well as by the photo detection channels. If the analyte is water and the gas mixture is natural gas, the wavelength $\lambda_N$=1550.12 nm, which falls into the International Telecommunication Union (ITU) grid of wavelengths for optical communications. In such an instance REFL1 is easy available at low cost.

For monitoring more than one analyte, an additional reference laser ("REFL2") 248, lasing on another single reference wavelength $\lambda_{N2}$, may be utilized in the present invention. REFL2 may deliver its reference output to the single mode optical fiber 250, and may further extend its reference output the other input of the 50/50, 2×1 fiber optic combiner 249. The single mode optical fiber 251 carries the reference wavelength output of the combiner 249, which may be a coupler, with reference optical power $P_F(\lambda_F)$ at the other input of the 50/50 optical combiner 244. The reference wavelength output may emerge on the fiber 246 and may then follow an optical path that is identical or virtually to that of the beam from the tunable laser (e.g., TSL1 or TSL2).

The optical fiber 246 is operable to carry or otherwise direct the interrogation beam. The interrogation beam may have either a tunable wavelength or a reference wavelength. A skilled reader will recognize that only one laser appearing in the diagram shown in FIG. 3i may be active at a time. A skilled reader will also recognize that the embodiment of the present invention shown in FIG. 3i may be configurable, so that one or more additional tunable lasers and/or one or more additional reference lasers may be integrated in the embodiment. Each of the additional tunable lasers and/or reference lasers integrated in the present invention may have associated optics and control electronics that are the same or similar to the optics and control electronics of the tunable lasers and reference lasers discussed herein.

The output of the fiber optic combiner 244 with optical power $P_L(\lambda,I_B)$ sends the interrogation beam through the single mode optical fiber 246 to the input of the 1×2 optical splitter 245. In one embodiment of the present invention, the splitter 245 is 99/1 type, meaning that 99% of the input beam goes to main output and 1% of the input beam goes to taper output, assuming zero internal loss. In embodiments of the present invention, $P_L(\lambda,I_B)$ can be either the power $P_T(\lambda,I_B)$ emitted either by TLS1, or by TLS2, or the power emitted either by REFL1 or by REFL2. The beam splitter 245 directs the reference power $P_0(\lambda,I_B)=(1-S_C)\cdot P_L(\lambda,I_B)$ where $S_C=0.99$, through the single mode optical fiber 252, on the reference photodiode 274. This generates the reference photocurrent 253 that is $PI_0(\lambda,I_B)$, going to the input of the logarithmic amplifier 254 ("LOG 0"). The LOG 0 generates the output voltage 255 as $UL_0=\log(I_0(I_B))$ that is directed to the non-inverting input of the DLOG differential amplifier 256.

The power $P_1(\lambda,I_B)=S_C\cdot P_L(\lambda,I_B)$, where $\lambda$ is the laser wavelength, $I_B$ is the laser bias current, $S_C=0.99$, from the splitter 245 is directed to the gas cell as input power. The input power is carried or otherwise directed by the single mode optical fiber 275 toward the input fiber optic collimator 210 at the input of the gas cell. A skilled reader will recognize that the split ratio 99/1 of the fiber optic splitter 245 may be altered in embodiments of the present invention.

The beam 213 with optical power $P_2(\lambda,I_B)$ collected by the output fiber optic collimator 215 as cell output optical power, is carried or otherwise directed by the single mode optical fiber 257 towards the output photodiode 258. The photodiode 258 generates the photocurrent 259 as $PI_2(I_B)$, at the input of the logarithmic amplifier 260 ("LOG 2"), producing the output voltage 261 as $UL_2=\log(I_2(I_B))$. The photocurrent is also applied to the non-inverting input of the DLOG differential amplifier 256.

The controller 290 monitors the operation of the measuring module 262. The controller generates: the bias current 263 as $I_{B1}$ for fast tuning of DFB laser TLS1; the voltage 264 as $U_{TEC1}$, utilized to set the initial wavelength of TLS1 in the absence of wavelength scanning by adjusting the control voltage of the thermoelectric cooler TEC embedded in TLS1; the voltage 265 as $U_{T2}$, utilized to tune the wavelength of the tunable laser TLS2; the bias current 266 as $I_{RL1}$ utilized as the current for the reference laser 247; the bias current 267 as $I_{RL2}$ utilized as the current for the reference laser 248. The controller converts to digital format signals such as: voltage 268 from the output of the referenced signal DLOG differential amplifier 256; voltage 269 from the output of the temperature sensor 235 and the voltage 270 from the pressure sensor 236. The controller communicates with the host 271 through the serial communication 272 and through the analog output 273. The host may be a remote monitoring unit collecting analyte concentration data from multiple apparatuses according to the present invention or similar monitoring units, or a human operating the present invention to monitor an analyte in the gas mixture in the gas cell. A skilled reader will recognize that additional signals may be generated by the controller, and that additional functions of the controller may be added to embodiments of the present invention.

As shown in FIG. 3a, in an embodiment of the present invention, the optical layout of the measuring module 300 may be comprised of bulk optical elements. The gas cell 201 may have a closed configuration. The input collimator 302 and the output collimator or telescope 303 may collect the beam 213 emerging from the gas cell, and the input collimator and output collimator may each comprise bulk optical elements. A cover 301 may be positioned over the gas cell to close the gas cell. A skilled reader will recognize that some optical elements of the measuring module may contain optical fibers. For example, some lasers may be pigtailed, and accordingly may incorporate some components operable to facilitate a transition from optical fibers to bulk optics. For clarity, a pigtailed optical component is a bulk optical element, for example, such as a lens coupled optically with an optical fiber into a single housing that can be used as a single optical component in the present invention.

The beam 304 from TLS1 laser 305 goes through the dichroic mirror 306, reflects again on highly reflective mirror 307 and is incident as beam 308 on the dichroic beam combiner and splitter 309. The beam 310 with reference optical power $P_0(\lambda,I_B)=(1-S_C)\cdot P_T(\lambda,I_B)$ where $S_C=0.99$ is incident on the reference photodiode 274, generating the reference photocurrent $PI_0(I_B)$. The beam 311 with the optical power $P_1(\lambda,I_B)=S_C\cdot P_T(\lambda,I_B)$ where $S_C=0.99$, goes to the bulk input collimator 302. In one embodiment of the present invention, $P_T(\lambda,I_B)$ denotes the power from any tunable laser, either TLS1 305 or TLS2 312. A skilled reader will recognize that the tunable lasers 305 and/or 312 shown in FIG. 3a may be a different type of tunable laser than the tunable lasers 238 and 239 shown in FIG. 3i. The beam emerging from the input collimator 302 is reflected multiple times between the reflective layers 208 and 209, passing into and through the gas cell 201 in each section of the path of the beam that is a reflection of the beam between the two reflective layers. The beam 213 that emerges from the gas cell and is no longer reflected between the two reflective layers is collected by the telescope 303.

The output beam 313 from TLS2 312 is reflected by the high reflectivity mirror 314 toward the dichroic mirror 306 emerging after the reflection occurs as beam 315. The beam then is directed by reflection to the high reflectivity mirror 307 and is reflected to the optical path 302. After reflection onto mirror 307, the beam directed from TLS2 follows the same optical path, or virtually the same optical path, as the beam directed from TLS1, until the incidence on the reference photodiode 274 and on the output photodiode 258.

When the reference wavelength laser REFL1 319 is activated, its output beam 318 is reflected by the high reflectivity mirror 320 as beam 321. The beam is reflected again by the mirror 316 as beam 317 with optical power $P_N(\lambda_N)$ incident on the dichroic beam splitter and combiner 309. The wavelength reference beam 310 with reference optical power $P_0(\lambda_N, I_B) = (1-S_C) \cdot P_F(\lambda_N)$ where $S_C = 0.99$, reflected by the beam splitter and combiner 309 is incident on the reference photodiode 274, generating the reference photocurrent $PI_0(I_B)$. The power $P_1(\lambda_N, I_B) = S_C \cdot P_N(\lambda_N)$, where $S_C = 0.99$, from the reference laser REFL1 goes through the dichroic combiner 308 on the same optical path 311 as did the beam originated from the laser TLS1, being now the beam incident on the input collimator 302. The emerging beam from the collimator 302 follows the same optical path, or virtually the same optical path, between the reflective layers 208 and 209 and inside the gas cell 201 as the beam from any tunable laser TLS1 or TLS2. The beam is collected by the telescope 303.

The output beam 322 from the wavelength reference laser REFL2 323 goes through the dichroic beam combiner 316 emerging as beam 317 which follows an identical optical path, or virtually identical optical path, to the beam generated by REFL1 319. A small fraction of the power of the wavelength reference beam 317 is directed as power reference beam 310 toward the reference photodiode 274. Most power of the wavelength reference beam 317 is directed as beam 311 toward the gas cell 201.

The telescope 303 collects the beam 213 emerging from the gas cell 201 and directs it as beam 317 with incident power $P_2(\lambda, I_B)$ to the output photodiode 258, producing the photocurrent $PI_2(I_B)$.

In all the embodiments of the present invention, only one laser is active at a time. For example, only one of the following lasers is active in an embodiment of the present invention at a time: TLS1, or TLS2, or REFL1, or REFL2.

As shown in FIG. 3b, an embodiment of the present invention may incorporate a measuring module 262 built with fiber optic elements and an open gas cell module 330. All of the elements of the measuring module 262 shown in FIG. 3b have the same functionality as the elements of the measuring module 262 shown in FIG. 3i.

The gas cell unit of FIG. 3b may have an open configuration that incorporates a pig-tailed fiber optic input collimator and a pig-tailed output fiber optic collimator or telescope. (As discussed herein, a pigtailed component is one that is a bulk component, such as a lens coupled optically with an optical fiber, contained within the same housing and used as a single optical component.)

The open gas cell module 330 works in free air without restricting the measuring volume, in a similar manner to the gas cell module 276 as in FIG. 3i. The transceiver 331 ("TRSV"), is incorporated in the gas module 330. The TRSV contains the bulk optical collimator 332a ("BCOL") that generates the collimated light beam 333. The collimated light beam propagates in free space toward the retro reflector 334 ("RRFL"). The retro reflector 334 comprising an array of cube corners, or a light scattering surface, that reflects the beam with low losses or with high losses. The beam is reflected dominantly in the direction of the incident beam 333. The beam 335 is collected by the pigtail telescope 336. The pigtail telescope is incorporated in the transceiver 331 so as to be mounted in the proximity of the collimator 332.

The output beam of the pigtail telescope 336 passes through the single mode optical fiber 257 and has a path that reaches the measuring module 262.

The spacing $L_t$ between the collimator 332 and the retro reflector 334 can be between 0.25 m and several hundred meters, depending on the power of the lasers TLS1, TLS2, REFL1 and REFL2 of the measuring module 262. The gas mixture holder 337 integrated in the present invention between the transceiver 331 and the retro reflector 334 may contain one or more analytes that may be a variety of types of analytes, for example, such as water ($H_2O$), methane ($CH_4$), ethane ($C_2H_6$), ethylene ($C_2H_4$), propane ($C_3H_8$), propylene ($C_3H_6$), isobutene ($C_4H_{10}$), butane ($C_4H_{10}$), hydrogen ($H_2$), hydrogen sulfide ($H_2S$), sulfur dioxide ($SO_2$), carbon monoxide (CO), carbon dioxide ($CO_2$), hydrogen cyanide (HCN), oxygen ($O_2$), carbonyl sulfide (COS), sulfide ($S_2^-$), sulfate ($SO_4^{2-}$), chloride ($Cl^-$), or other analytes of interest, including analytes that are of interest either as air pollutants and/or as leaks coming expelled from industrial and biological activity. A skilled reader will recognize that the monitoring unit of embodiments of the present invention may be operable to monitor either a single analyte or multiple analytes.

As shown in FIG. 3c, embodiments of the present invention may incorporate a measuring module 262 built with fiber optic elements (as shown in FIG. 3i) and a closed gas cell module 350. The gas cell module may be coupled with or otherwise attached to or integrated with an evaporator 351. The configuration of the present invention shown in FIG. 3c is operable to monitor the analyte 352 which is normally in liquid phase. The heater 353 driven by the HCTRL line 356, causes the analyte 352 to be expressed as a vapor phase 354, and the heater in its application to expressing the analyte as a vapor phase is monitored by the controller 357 through use of the signal from the temperature sensor 359. The analyte may be monitored in liquid phase at standard conditions of temperature and pressure. In one embodiment of the present invention, the fan 355 re-circulates the analyte vapors 354 through the gas cell 201 in a manner that continuous or virtually continuous.

The measuring module 262 sends the optical beam 275 to the gas cell and receives the light from the gas cell, in a manner that is the same, virtually the same, or similar to that described in reference to FIG. 3i.

As shown in FIG. 3d, embodiments of the present invention may incorporate a measuring module 300 comprising bulk optical elements that are the same, virtually the same or similar to those described in relation to measuring module 300 of FIG. 3a. The volume of the closed gas cell module 350 comprises a bulk input collimator and a bulk output collimator or telescope operable to communicate with the liquid evaporator 351. The liquid evaporator contains the analyte in liquid phase that is converted to gas phase. The analyte in gas phase is circulated to the gas cell.

An optical beam 311 is directed to the closed gas cell module 350. The closed gas module is connected, integrated with, or otherwise attached to a liquid evaporator 351. The liquid evaporator is heated by the element 353. The liquid evaporator receives from the gas cell module 350 the optical beam 317, in a manner that is the same, virtually the same or similar to that described in reference to FIG. 3c. The fan 355 provides a continuous gas flow of analyte vapors 354 through the gas cell 201, in a manner that is the same, virtually the same or similar to that described in reference to FIG. 3c. The controller 357 drives the heating element 353 through HCTRL line 356 and monitors the temperature through the operation of the temperature sensor 359.

As shown in FIG. 3e, embodiments of the present invention may incorporate a measuring module 262 comprising fiber optic elements in a manner that is the same, virtually the same or similar to the measuring module described and shown in FIG. 3i. The measuring module is attached to a closed gas cell module 360 in a manner that is the same, virtually the same or similar to the measuring module described and shown in FIG. 3i. The closed gas cell 201 incorporates a nacelle 361 that contains the probe 362 operable to embed the analyte in solid phase in standard conditions. The analyte may be embedded in solid phase in standard conditions in a known manner (see: National Bureau of Standards (NBS) (1982). "Table of Chemical Thermodynamic Properties". *Journal of Physics and Chemical Reference Data* 11 (Supplement 2)).

The high energy laser 363 ("HEL") sends its pulsed beam 364 through the optical port 365 of the housing 237 and also through the optical port 369 of the gas cell 201. The laser induced breakdown ("LIB") produced by the laser beam 364 on the probe 362 produces sequentially plasma in a known manner (see: Hahn D. W., Omenetto N. "Laser-induced Breakdown Spectroscopy (LIBS), Part I: Review of Basic Diagnostics and Plasma-Particle Interactions: Still-Challenging Issues within the Analytical Plasma Community", *Applied Spectroscopy*, 64, 12, 2010), and subsequently produces vapors. Both plasma and vapor of the analyte embedded in the probe 362 will be called analyte mixture 366. The SYNC signal 367 from the controller 368 triggers the HEL 363. The fan 371 refreshes the content of the gas cell 201. The fan is integrated in the chamber 370 which is connected to the gas cell. The chamber may be operable as a buffer chamber.

As shown in FIG. 3f, embodiments of the present invention may incorporate a measuring module 300 comprising bulk optical elements in a manner that is the same, virtually the same or similar to the measuring module described and shown in FIG. 3d. The measuring module is attached to a closed gas cell module 360 in a manner that is the same, virtually the same or similar to the measuring module described and shown in FIG. 3e. The measuring module 300 generates the beam 311 incident on the gas cell module 360, and receives the beam 317 from the gas cell module 360. The closed gas cell module 360 incorporates optical ports 365 and 369 for directing the optical beam 364 produced by the high energy laser 363. The high energy laser 363 is used to produce plasma and vapors, which are forms of the analyte mixture 366, by LIB from the probe 362 containing the analyte. The fan 371 refreshes the content of the gas cell 201 through the chamber 370.

As shown in FIG. 3g, embodiments of the present invention may incorporate a measuring module 262 comprising built with fiber optic in a manner that is the same, virtually the same or similar to the measuring module described and shown in FIG. 3i. The measuring module is attached to a gas cell module 330 with open gas cell configuration that is the same, virtually the same or similar to the measuring module described and shown in FIG. 3b. The gas cell module 330 may be comprised of a pigtailed input fiber optic collimator and a pigtailed output fiber collimator or telescope. The high energy laser 365 ("HEL") focuses its output beam 364 to the solid probe 362. The SYNC pulse 367 from the controller 368 of the measuring module 262 triggers the HEL to generate the high energy beam 364. The high energy beam initially produces the plasma and subsequently produces the vapors of the analyte. The plasma and vapors of the analyte are forms of the analyte mixture 366. The single mode optical fiber 275 carries the light from the measuring module to the fiber optics collimator 332a, which sends a collimated input beam 333 into the free space between the collimator 332a towards the retro reflector 334 ("RRFL"), passing through the analyte mixture 366. The beam 335 is reflected back by the retro reflector 334 and passes through the analyte mixture 366 again. The beam is collected by the fiber optic telescope 336a coupled to the single mode fiber 257. Once collected the beam is directed to the measuring module 262.

As shown in FIG. 3h, embodiments of the present invention may incorporate a measuring module comprising bulk optical elements 300 in a manner that is the same, virtually the same or similar to the measuring module described and shown in FIG. 3a. The measuring module is attached to an open gas cell module 330 that is the same, virtually the same or similar to the measuring module described and shown in FIG. 3b. The controller 368 provides SYNC signal 367 operable to trigger the high energy laser 363 ("HEL") in a manner that is the same, virtually the same or similar to the measuring module described and shown in FIG. 3f. The solid probe 362 containing the analyte is located in the nacelle 361. The focused high energy laser beam 364 emitted by the HEL produces by LIB successively plasma and vapors containing the analyte embedded in the probe 362. Either plasma or the vapors containing the analyte are forms of the analyte mixture 366. The embodiment of the present invention monitors either the plasma or the vapors of the analyte, or both the plasma and the analyte through the resonant absorption of the laser beams 333 and 335 by the analyte.

The embodiments of the present invention of FIGS. 2 and 3a-3h incorporate a gas cell wherein single side collimators are integrated. The embodiment of the present invention shown in FIG. 4 incorporates a gas cell wherein opposed collimators are integrated.

Figure 4:
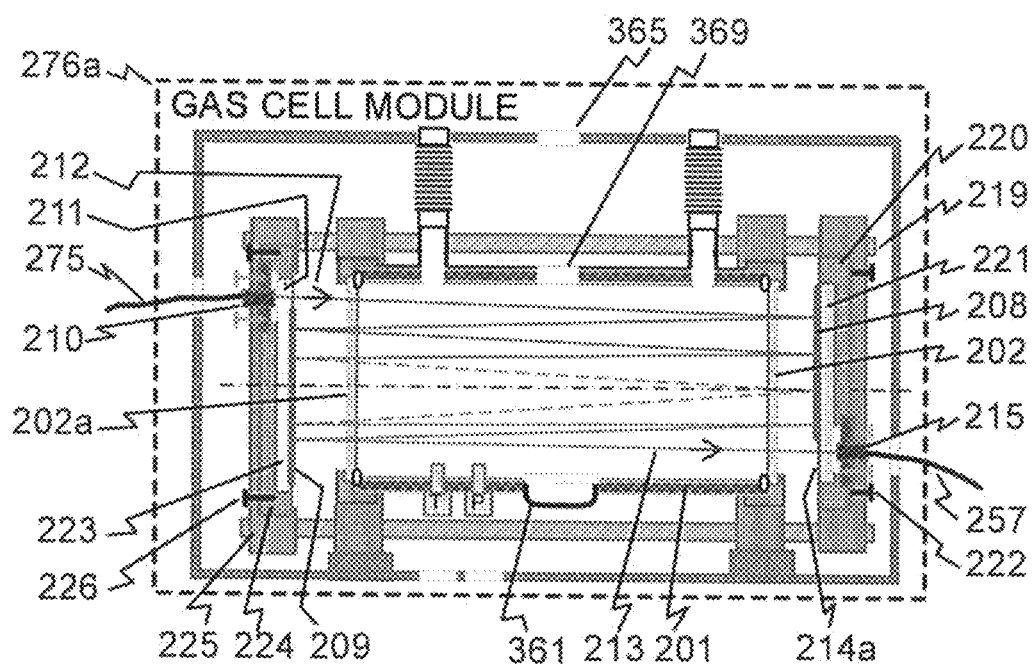
FIG. 4 is a schematic drawing of an embodiment of the closed gas cell of the apparatus of the present invention.

As shown in FIG. 4, embodiments of the present invention may incorporate a closed gas cell 201 wherein an input fiber optic collimator 210 and an output fiber optic collimator 215 are incorporated so as to be positioned on opposite ends of the gas cell 201. A skilled reader will recognize that fiber optic collimators 210 and 215 can be replaced by collimators comprising bulk optical elements having the same functionality or virtually the same functionality or similar functionality to that described herein in reference to FIG. 3i. The gas cell module may be encompassed by an enclosure 276a, as shown in FIG. 4. A mirror 214a may be integrated in the gas cell module.

The closed gas cell as shown in FIG. 4 may differ from the closed gas cell as shown in FIG. 3i in at least the following manners: the output fiber optic collimator may be located on the opposite end of the gas cell than the input fiber optic collimator; and both the front mirror and the back mirror may be identical, having their optical ports aligned with the positions of the respective fiber optic collimators. The closed gas cell further incorporates a nacelle 361, and optical ports 365 and 369 that are the same, virtually the same or similar in configuration and function as is described herein in relation to FIGS. 3e and 3f. A skilled reader will recognize that closed gas cell configuration as shown in FIG. 4 may be integrated in embodiments of the present invention as shown in FIGS. 2, 3c and 3e to replace the closed gas cells of such embodiments. A skilled reader will also recognize that the gas cell as shown in FIG. 4 may comprise bulk optics in the manner of the gas cell as shown in FIGS. 3a, 3d, 3f and 3h, so that the fiber optic collimators of FIG. 4 are replaced with their bulk optics counterparts as shown and described for FIGS. 3a, 3d, 3f and 3h.

Embodiments of the present invention may incorporate a three dimensional ("3D") front mirror 11, as shown in FIG. 5a. The front mirror may be integrated with a gas cell module 276 that incorporates a closed gas cell 201 having collimators positioned solely on one side of the gas cell, as shown and described in FIG. 3i. The highly reflective layer 209 and the highly transparent optical ports 211 and 214 of the mirror substrate 223 may be oriented toward the gas cell. The other face of the substrate 223 incorporates an anti-reflective layer 501. The anti-reflective layer may completely cover the area of the highly reflective layer 209 and of the optical ports 211 and 214. The anti-reflective layer 501 is operable to minimize the absorption of the incident beam 212 and the absorption of the emerging beam 213 at their propagation through the front mirror 11. The front mirror may be a mirror such the mirror 11, as shown in FIG. 5a. (Incident beam 212 and emerging beam 213 are shown in FIG. 3i.) The anti-reflective layer is further operable to prevent the stray rays from passing through the highly reflective layer 209 and returning back to the highly reflective layer 209. The anti-reflective layer of the front mirror 11 may be an anti-reflective coating.

Figure 5B:
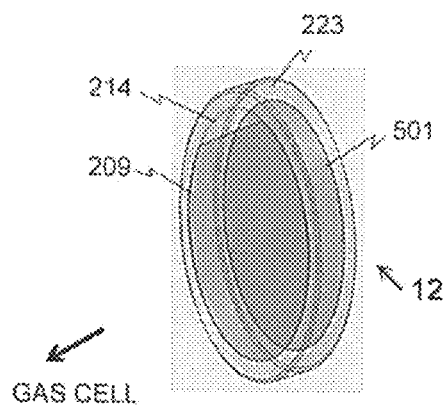
FIG. 5b is a perspective cross-section of an embodiment of the front mirror and the back mirror of the gas cell of the apparatus of the present invention.
Figure 5C:
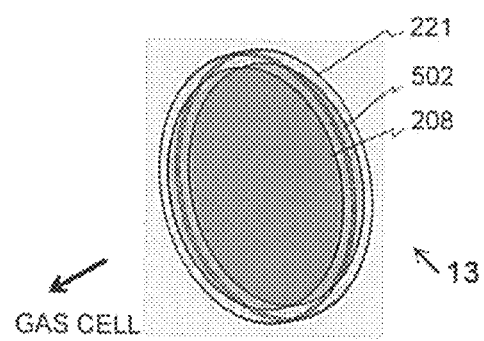
FIG. 5c is a perspective cross-section of an embodiment of the back mirror of the closed gas cell of the apparatus of the present invention.

Embodiments of the present invention may incorporate a 3D mirror 12, as shown in FIG. 5b. The 3D mirror 12 may be integrated with a closed gas cell configured so as to integrate an input collimator and an output collimator, said input collimator and output collimator being positioned on opposite sides of the gas cell. A 3D mirror 12 may be integrated at each end of the gas cell 201.

The front side of the mirror substrate 223 may incorporate solely one highly transparent optical port 214 and a highly reflective layer 209. The back side of the substrate 223 may incorporate an anti-reflective layer 501. The mirror 12 may be integrated in the gas cell as the front mirror and the mirror 12 may also be integrated in the gas cell as the back mirror. The mirror 12 is integrated with the gas cell on either, or both, the front end and the back end of the gas cell, so as to be positioned such that the highly reflective layer 209 is facing the gas cell 201. The optical port 214 of the mirror 12 is respectively aligned with the input collimator 210 and with the output collimator. The anti-reflective layer of the 3D mirror 12 may be an anti-reflective coating.

Embodiments of the present invention may incorporate a 3D back mirror 13, as shown in FIG. 5c. The back mirror 13 may be integrated with a gas cell module 276 that incorporates a closed gas cell 201. The closed gas cell having an input collimator and an output collimator positioned therein so that the input collimator and the output collimator are each positioned on the same side of the gas cell. The back mirror 13 may be integrated with the gas cell as the back mirror 221 of the gas cell. When integrated with the gas cell the back mirror 13 may be positioned so that the highly reflective layer 208 of the mirror 13 is facing the gas cell 201. The anti-reflective layer 502 of the back mirror 13 may be an anti-reflective coating.

Embodiments of the present invention may incorporate a front mirror assembly 14, as shown in FIG. 6. The front mirror assembly may be integrated with a closed gas cell 201 having optical collimators positioned on the same side of the gas cell. The front mirror assembly may incorporate a mirror plate 601, locking screws 602, and pull screws 226. The mirror substrate 223 may incorporate a highly reflective layer 209, transparent optical ports 211 and 214 and an anti-reflective layer 501. A mirror 223 having a highly reflective coating 209 is directed toward the gas cell and is rigidly held in position by the mirror holder 224 attached to the mirror mount 225. The front mirror assembly may be positioned so that the highly reflective layer 209 faces the gas cell 201 on the back side of the view so that the anti-reflective coating 501 is on the front. Pairs of push screws 604 and pull screws 226 are utilized to maintain the position and relationship of the mirror mount, mirror holder and the mirror. For example, three pairs of pull screws 603 and push screws 604 may be used to achieve angular alignment of the highly reflective layer 209 and to lock it in the aligned position.

Input optical port 211 operable to receive input beam into the gas cell, and output optical port 214 operable to direct the output beam exiting from the gas cell should match the positions of the input collimator 210 and of the output collimator 215, respectively. A skilled reader will recognize the manner of use of the pull screws 226 and the push screws 604 to achieve optical alignment of the reflective layer 209 to produce multiple reflections of the input beam 212 between the reflective layers 208 and 209.

The mirror mount 225 is rigidly attached to the mirror plate 601 with three locking screws 602. The screws 602 are used for alignment of the transparent ports 214 with the respective fiber collimators 210 and 215 by shifting the mirror mount 225 perpendicular to the axis 213 of the gas cell. The screws 602 also lock the mount 225 to the mirror plate 601. The holes 605 are used for mounting the mirror plate 601 to the cage system 219 in a manner shown in FIG. 8. A skilled reader will also recognize that the front mirror assembly 14 may be used to mount any of the mirrors 11, 12 and 13 as shown in FIGS. 5a-5c into the cage system on either the front end or the back end of a gas cell. A skilled reader will further recognize that the screws 222 have the same function as the push screws 226.

Embodiments of the present invention may incorporate a collimators plate assembly 15 as shown in FIG. 7. The collimators plate assembly 15 may be integrated with a closed gas cell 201 so that the optical collimators are positioned to be on the same side of the gas cell. The collimators plate assembly 15 incorporates a collimator plate 700, collimator mounts 701 and 703, and locking screws 702 and 704. The input fiber collimator holder 227 is attached to the input collimator mount 701 with the pull screws 228 and push screws 228a to achieve a solid mounting. The pull screws and push screws may be utilized to achieve optical alignment and to lock the fiber optic input collimator in a particular position.

The collimator mount 701 is attached to the collimator plate 700 in a solid manner by an attachment means, for example, such as three mounting screws 702. The collimator plate 700 has holes 705 integrated therein for the purpose of mounting the plate 700 to the cage system 219, in the manner shown in FIG. 8. A person skilled in the art will recognize that positions of the input collimator 227 (and its associated hardware) and the output fiber optic collimator 215 (and its associated hardware) are interchangeable within embodiments of the invention, and that this interchangeability of the positions will not affect the functionality of the collimators plate assembly 15. A skilled reader will further recognize that a gas cell comprising fiber optic collimators positioned on opposite sides of the gas cell will incorporate one collimator plate assembly 15.

The collimators plate assembly 15 can be utilized in relation to the input collimator 210 and to the output collimator 215. The discussion herein is related to the utilization of the collimators plate assembly 15 with the input collimator 210, but the utilization of the collimators plate assembly 15 with the output collimator 215 is achieved in a similar manner, as will be recognized by a skilled reader.

The input fiber optic collimator 210 is attached into the fiber collimator holder 227. The fiber collimator holder is attached to the fiber collimator mount 701 by an attachment means, for example, such as three pair of push screws 228a and pull screws 228. The attachment means may be operable to achieve the angular alignment of the collimator 210 and to lock it in a particular position in accordance with a known method.

The collimator mount 710 is translated perpendicular to the axis 213 of the gas cell and is locked in the final position with the screws 702. Similarly, the output fiber optic collimator 215 is attached to the fiber optic collimator holder 216 by the collimator mount 703. The collimator mount 703 is attached in a locked position to the outer collimator plate 706. The fiber optic collimators 210 and 215 are aligned to achieve the optical setup, as shown in FIG. 8. A skilled reader will recognize that the collimator assembly (as shown in FIG. 7) is utilizable in the front mirror assembly (as shown in FIG. 6) and in a back mirror assembly 610 (as shown in FIG. 8). A skilled reader will also recognize that the mirror assembly 610 is the same as the mirror assembly 601, whereby the mirror shown in FIG. 5a can be replaced by the mirror shown in FIG. 5. A skilled reader will further recognize that the gas cell configuration with opposing positioned fiber collimators (as shown in FIG. 4) may incorporate the front and back mirror assemblies as shown in FIG. 6, with the mirror as shown in FIG. 5b, and the collimator assembly at each end is as shown in FIG. 7 having only one fiber optic collimator mounted.

An embodiment of the gas cell assembly 16 of the present invention, as shown in FIG. 8, may incorporate a gas cell module 276. (Notably, solely the base plate 805 is shown in FIG. 8 as integrated as part of the housing 237. This depiction is for the purpose of clarity.) The gas cell assembly 16 may further incorporate cage bases 801 and 802 operable to mount shock and vibration absorbers 230, a fitting 803 operable for attaching the gas cell 201 to a gas mixture holder through the bellows 232, a fitting 804 operable for attaching the gas cell 201 to the gas mixture holder through the bellows 233, a base plate 805 operable for holding the entire gas cell assembly 16, and the other elements shown in FIG. 8.

B. Methods of Operation

Embodiments of the present invention may have particular functionalities and operabilities, some of which have been previously discussed. As an example of the operation of an embodiment of the present invention, the discussion in this section will pertain to the operability and method of an embodiment of the present invention as shown in FIG. 3i. A skilled reader will recognize that other and additional operabilities and methods are possible for embodiments of the present invention.

The description of the operation of the present invention in this section will further specifically reference monitoring the water ($H_2O$) as analyte in a natural gas mixture, that is primarily composed of methane ($CH_4$) between 70% to 90% and also of other gases such as ethane ($C_2H_6$), propane ($C_3H_8$), butane ($C_4H_{10}$), carbon dioxide ($CO_2$), oxygen ($O_2$), nitrogen ($N_2$), hydrogen sulfide ($H_2S$), water ($H_2O$) and traces of several rare gases such as argon (Ar), helium (He), neon (Ne), xenon (Xe) and also other gases. A skilled reader will recognize that other analytes in other gas mixtures may be monitored by embodiments of the present invention. Embodiments of the present invention may be utilized to monitor any analyte that is incorporated in any gas mixture.

When monitoring the water in natural gas, an aspect of the gas mixture that is of primary importance is the methane content of the gas mixture. The description of the method of the present invention for monitoring the analyte water in a gas mixture will be in the context that the gas mixture incorporates methane.

The absorption spectrum of atoms and molecules of matter consist of discrete resonant absorption lines, each absorption line having an absorption peak, regardless of whether the phase of the atoms and molecules is a gas, or liquid or solid phase. A transmission spectrum is complimentary to the absorption spectrum. The transmission spectrum will incorporate transmission dips that correspond to absorption peaks. The terms "absorption peak" and "transmission dip" are used interchangeably herein and a skilled reader will understand that for each absorption peak there will be a corresponding transmission dip, and vice versa.

Analyte monitoring in accordance with a method of the present invention involves multiple requirements. For example, for monitoring an analyte such as water vapors within a natural gas mixture at standard conditions (see: National Bureau of Standards (NBS) (1982). "Table of Chemical Thermodynamic Properties". *Journal of Physics and Chemical Reference Data* 11 (Supplement 2)), the analyte must be in the gas phase. Therefore, the analyte must be in a gas phase and achieved the required monitoring temperature and pressure. If the analyte is not in the gas phase the analyte or the mixture containing the analyte must be brought to gas phase. The analyte may be induced into a gas phase through various methods, including evaporating the analyte from a liquid phase, or by applying laser induced breakdown ("LIB") to an analyte in a solid phase.

Another requirement is that within a chosen spectral region, the analyte and each component of the gas mixture must have spectra with distinct, non-overlapping resonant absorption lines. Each absorption line must have a unique resonant absorption peak, or transmission dip, among the absorption spectra of all gases of the mixture.

Figure 9A:
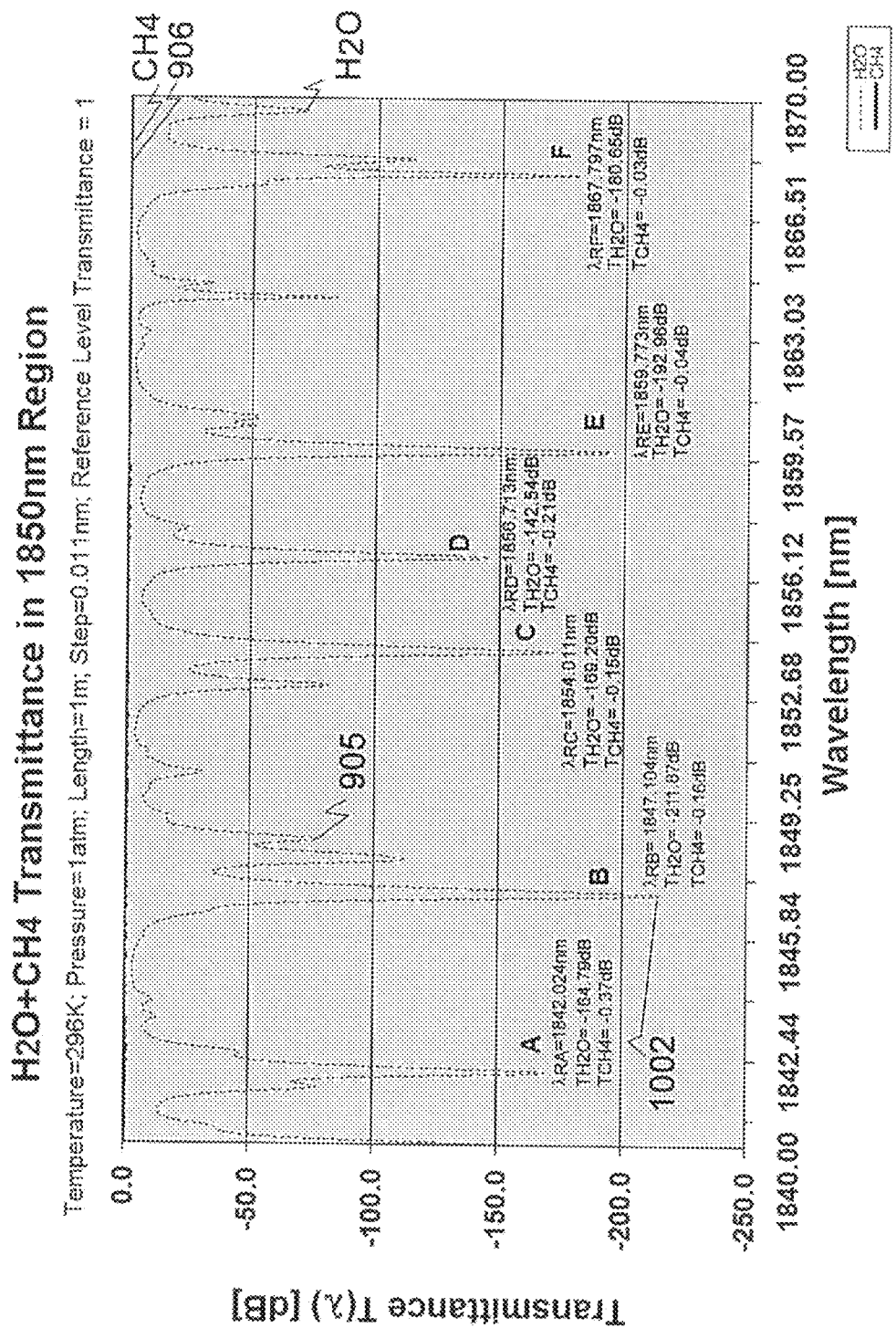
FIG. 9a is a graph showing transmittance of water vapors and of methane in 1850 nm region in accordance with an embodiment of the present invention.

FIG. 9a shows a transmittance graph plotting water vapors ($H_2O$) and methane ($CH_4$) in the spectral region between 1840 nm and 1870 nm, at absolute temperature T=297K, pressure p=1 atm, interaction length L=1 m using data from HITRAN on the Web http://hitran.iao.ru/molecule/bands/mol/1. In other words FIG. 9a shows a transmittance graph of water vapors and of methane from 1840 nm to 1870 nm in logarithmic scale for transmittance referenced to unity $T(\lambda)=1$, or to zero absorption. A skilled reader will recognize that gas parameters, such as temperature and pressure, change the absorption linewidth lines but do not change the absorption peak wavelength at any interaction length. The transmittance shown on the graph in FIG. 9a is in dB with reference level at zero absorption or unity transmittance. The main transmittance dips or absorption peaks are labeled as A, B, C, D, E and F. The corresponding values for peak wavelengths that are $\lambda_{RA}$, $\lambda_{RB}$, $\lambda_{RC}$, $\lambda_{RD}$, $\lambda_{RE}$ and $\lambda_{RF}$, water absorption $T_{H2O}$ and methane absorption $T_{CH4}$ values are shown on the graph for each main absorption peak. In the wavelength range shown in FIG. 9a, water absorption on labeled peaks is much higher than the methane absorption. As examples, these values will be utilized in the equations below to exemplify the transmittance dip 1002, which as the lowest transmittance of −211.87 dB in the spectral region, being between 1840 nm and 1870 nm. The wavelength sweep range of the tunable laser TLS1 is narrow enough not to reach the dip 905 which may corrupt the measurement if it is reached. The methane transmittance in the spectral range 906, as shown in FIG. 9a, is very close to 0 dB. The absorption property in relation to the water and the methane will be used in embodiments of the present invention for the purpose of monitoring water as analyte in natural gas mixture.

Embodiments of the present invention may measure conditions of non-overlapping absorption lines, such that the measurements collected include a measurement of the peak absorption of a single absorption line of the analyte. The peak absorption of a single absorption line of the analyte is proportional with the analyte density within a delimited volume at measured pressure and temperature of the gas mixture. The preferred absorption peak wavelength may be $\lambda_R=1847.104$ nm in an embodiment of the present invention. A skilled reader will recognize that other absorption peak wavelengths may be utilized in other embodiments of the present invention, and that any absorption peak in any spectral range can be used in the present invention, provided that at the selected absorption peak there is insignificant absorption by the other gases of the gas mixture.

A skilled reader will recognize that the transmittance in dB given by $T=10 \cdot \log(P_2/P_1)$. $P_1$ is the laser beam power at the gas cell entrance (e.g., of laser beam 212), and that $P_2$ is the laser beam power at the gas cell exit (e.g., of laser beam 213).

Figure 9B:
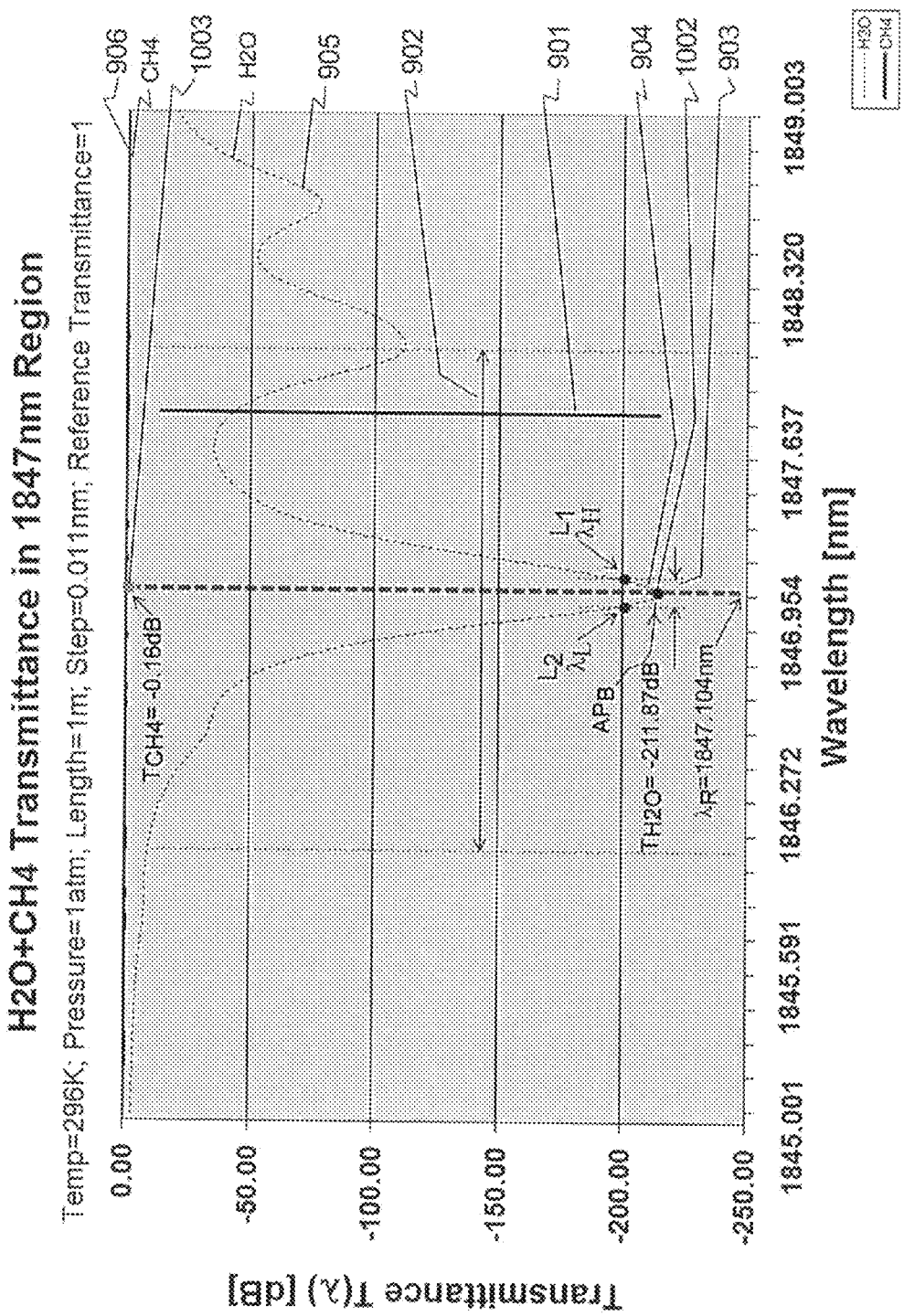
FIG. 9b is a graph showing transmittance of water vapors and of methane gas in 1847 nm region in accordance with an embodiment of the present invention.

FIG. 9b shows a transmittance graph of water vapors and of methane gas in 1847 nm region in logarithmic scale referenced to unity transmittance $T(\lambda)=1$, or to zero absorption from data provided by built with data from HITRAN on the Web http://hitran.iao.ru/molecule/bands/mol/l, obtained in the conditions specified on the graph. The graph shows very strong absorption of water $T_{H2O}=-211.87$ dB (indicated by reference number 1002) and very weak absorption of methane $T_{CH4}=-0.16$ dB at $\lambda_R=1847.104$ nm (indicated by reference number 906). The points $L_1$ and $L_2$ on the transmittance graph of water are about 11 dB higher than the transmittance dip, or about 11 dB below the absorption peak $AP_B$ 1002 shown on the graph. The higher transmittance dip 905 will be out of the wavelength sweep range of the tunable laser TLS1 238. There is a robust transmittance gap 904 of about 11 dB between the transmittance dip and the points $L_1$ and $L_2$ for reliable detection of the absorption peak.

Figure 9C:
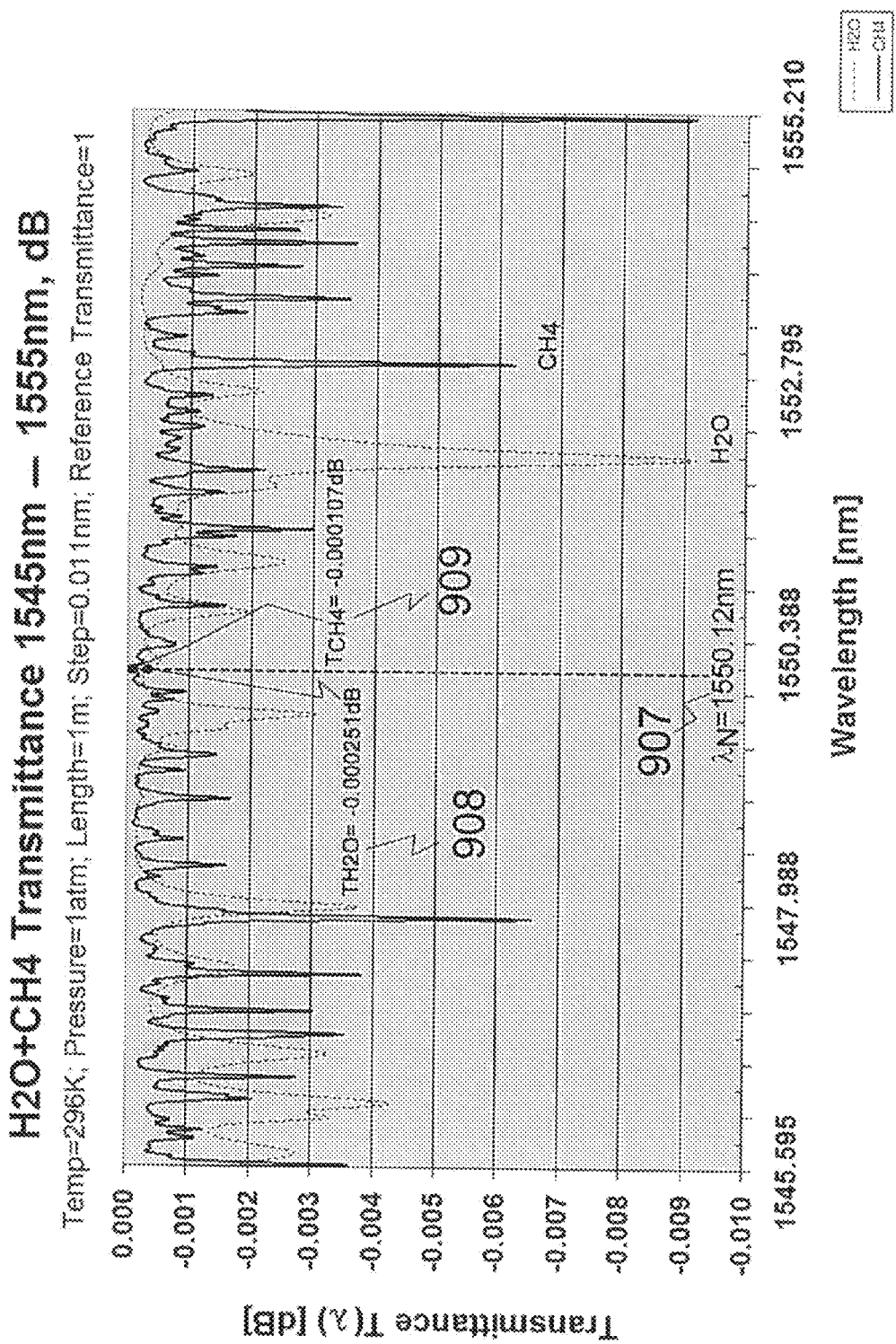
FIG. 9c is a graph showing transmittance of water vapors and of methane gas in 1545 nm-1555 nm region in accordance with an embodiment of the present invention.

FIG. 9c shows a transmittance graph of water vapors and of methane in 1550 nm region from data provided by reference by HITRAN on the Web http://hitran.iao.ru/molecule/bands/mol/l, obtained in the conditions specified on the graph. The reference laser REFL1 is lasing on the reference wavelength $\lambda_N=1550.12$ nm (as indicated by reference number 9007), where the water transmission 908 is $T_{H2O}=-0.000251$ dB and methane transmission 909 is TCH4=-0.000107 dB The method of embodiments of the present invention involves sweeping a wavelength of a tunable laser source or TLSx, where x=1, 2 used as a light source within a gas mixture to determine the absorption peak of an analyte incorporated in the gas mixture, such as a water analyte. The mass of the analyte contained within a defined volume is derived from the value of the absorption peak, in accordance with equation (15).

As shown in FIG. 3i, the optical power $P_T(\lambda,I_B)$ 243 from TLS1 238 is directed so as to enter into one input of the beam combiner 244. The beam from the reference laser REFL1 247 is directed to the other input of the beam combiner, either through the optical fiber 241, or from REFL2 248 through the optical fiber 241. When TLS1 238 is active, none of the other lasers 239, 247 and 248 are active. Therefore, $P_L(\lambda,I_B)$ is directed from TLS1 248 with a certain loss. However, the loss does not affect the method of the present invention.

The wide band WDM splitter 245 with the split ratio $S_C$ and $S_R=(1-Sc)$ divides $P_L(\lambda,I_B)$ into $P_1(\lambda,I_B)$ directed towards the gas cell and $P_0(\lambda,I_B)$ having a path towards to the reference photodiode 274. In one embodiment of the present invention, $S_C=0.99$, and may further include losses in the splitter 245. Accordingly, the optical power at the input collimator 210 of the gas cell is $P_1(\lambda,I_B)=S_C \cdot P_L(\lambda,I_B)$ and the optical power incident on the reference photo diode 274 is $P_0(\lambda,I_B)=(1-S_C) \cdot P_L(\lambda,I_B)$. $S_C$ is practically constant across the tuning range required for finding the resonant absorption peak.

In the embodiment of the present invention shown in FIG. 3i, all the power losses from the input fiber 275 to the output fiber 257 not related to the analyte absorption at the resonant wavelength R are considered background of the absorption performed by analyte at $\lambda_R$. The background includes mainly the loss in the input collimator 210, the loss at each reflection on the reflective layers 208 and 209, the losses in the windows 202, and the beam collection and propagation losses from the output beam 213 to the photodiode 258. Equation (1) herein is utilized to determine the total interaction length $L_1$ between the light beam and the analyte inside the gas cell 201. $P_2(\lambda,I_B)$ is the optical power of the output beam 213 emerging from the gas cell, collected by the output collimator 212 and incident on the photodiode 258.

In one embodiment of this invention, as shown in FIG. 3i, TLS1 shown is a tunable DFB laser (for example, such as a tunable DFB laser described in Eblana Photonics EP1854-DM laser series http://www.eblanaphotonics.com/EP1854-DM-Series.php). A person skilled in the art will recognize that a tunable DFB laser may contains in a single housing a laser diode, a feedback photodiode, a thermoelectric cooler or TEC and a negative temperature coefficient NTC thermistor. A tunable DFB laser wavelength is shown in FIG. 9b as laser line 901, having about 0.00 pm linewidth. The center wavelength can be set arbitrarily at any value within 2 nm tuning interval 902, either by heating or by cooling the laser diode using the embedded TEC (for example, using a method described in Eblana Photonics EP1854-DM laser series http://www.eblanaphotonics.com/EP1854-DM-Series.php).

Thermal tuning has large time constants which can be in hundreds of milliseconds range. The same laser line 901 can be swept in across a 0.110 nm interval 903 in a microseconds range, as shown in FIG. 9b, by changing the bias current $I_B$ of the laser diode. In accordance with the method of the present invention, the resonant peak of any absorption line may be determined by setting a bias wavelength by thermal means using TEC, followed by fast wavelength sweep through the laser bias current (as discussed in relation to FIG. 9a, 9b and FIGS. 10a, 10b, 10c, 10d and 10e), in relation to the absorption peak B (as shown in FIG. 9a), with resonant wavelength $\lambda_R=1847.104$ nm. The method of determining the absorption peak is applicable to determining any peak absorption independent of the resonance wavelength and the analyte.

Figure 10A:
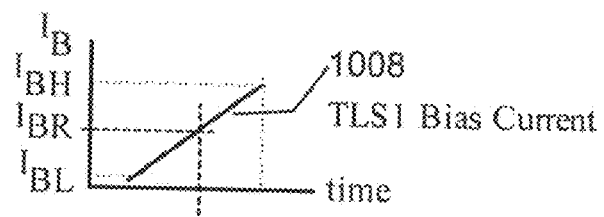
FIG. 10a is a graph of TLS bias current in accordance with an embodiment of the present invention.
Figure 10B:
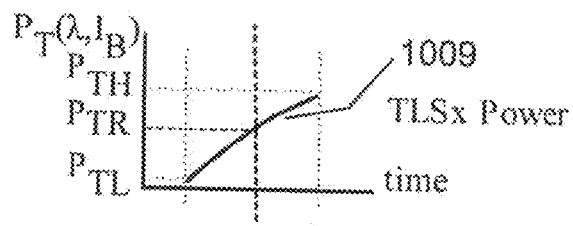
FIG. 10b is a graph of TLS output power in accordance with an embodiment of the present invention.
Figure 10C:
FIG. 10c is a graph of TLD output wavelength in accordance with an embodiment of the present invention.

Embodiments of the present invention may be operable to produce a graph, for example, such as in the format shown in FIGS. 10a, 10b and 10c, showing one or more of: TLSx bias current 1008 during fast tuning with bias current; TLSx output power 1009 during fast tuning with bias current; or TLSx wavelength 1010 during fast tuning with bias current. A skilled reader will recognize that the present invention can produce or otherwise generate other graphs, tables, charts, graphics, text, and other formats of information to be provided to a user.

To determine the absorption peak of the analyte, only the tunable laser 238 is active, and all the other lasers, such as indicated by reference numbers 239, 247 and 248 are turned off.

Figure 10D:
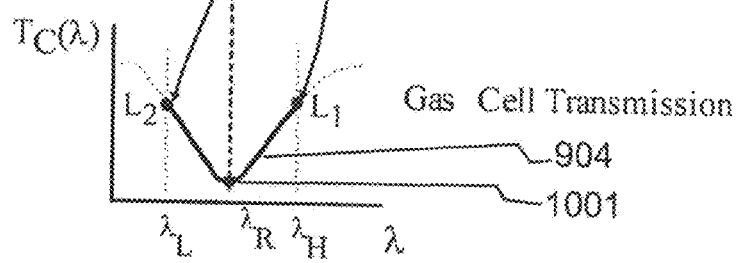
FIG. 10d is a graph of cell transmittance in accordance with an embodiment of the present invention.

As an initial step to determine the absorption peak or the transmission dip, the controller 290, using the signal $U_{TEC1}$ or 264, sets by thermal means the wavelength $\lambda_{L1}$ of DFB laser 238, to the point $L_1$ with wavelength $\lambda_H$ about 50 pm higher than the resonant wavelength $\lambda_R$. The status of DFB laser 238 (corresponding to the point $L_1$ in FIG. 9b) is defined by several parameters, such as the low bias current $I_B$ (as shown in FIG. 10a), the low optical power $P_{TL}$ (as shown in FIG. 10b), and the high wavelength λH (as shown in FIGS. 10c and 10d). There are no wavelength constraints for $\lambda_{L1}$ other than to be reasonably higher than the resonance wavelength $\lambda_R$. Also, there are no constraints on tuning linearity. $\lambda(I_B)$ must be only monotonic.

While being maintained as a constant the DFB laser temperature used for setting $\lambda_{L1}$, the wavelength sweep through the absorption peak of the analyte is achieved by monotonic increase of the bias current $I_B$ of the DFB laser 238 from the low value $I_{BL}$ to the high value $I_{BH}$ (as shown in FIG. 10a). By increasing $I_B$ from $I_{BL}$ to $I_{BH}$, the optical power $P_T(\lambda, I_B)$ 243 generated by the DFB laser 238 increases monotonically from $P_{TL}$ to $P_{TH}$ (as shown in FIG. 10b). Its lasing wavelength decreases monotonically from its high value $\lambda_H$ to its low value $\lambda_L$ (as shown in FIG. 10c).

All the graphs, as shown in FIGS. 10a-10c, are well known to those knowledgeable in the art and are presented also in M. Fukuda, M. Nakao, K. Sato, Y. Kondo, "1.55 mm Tunable DFB Laser with Narrow Linewidth and Higher Power", *IEEE Photonics Technology Letters*, 1, 1 (January 1989), p 6).

As the TLS1 wavelength moved from $\lambda_H$ to $\lambda_L$, the TLS1 wavelength goes through the resonance absorption wavelength $\lambda_R$ at the bias current $I_{BR}$, where the absorption in the gas cell reaches its maximum value. The density of analyte molecules $N_W$ at $\lambda_R$ is in accordance with that set out in H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf; J. L. Jimenez, "Lecture 6: Spectroscopy and Photochemistry II", *Atmospheric Chemistry* CHEM-5151/ATOC-5151, Spring 2005, http://cires.colorado.edu/jimenez/AtmChem/CHEM-5151_S05_L6.pdf.

FIG. 10a shows a diagram of TLS bias current $I_B(t)$ that may be applied by embodiments of the present invention for sweeping the wavelength (see: M. Fukuda, M. Nakao, K. Sato, Y. Kondo, "1.55 mm Tunable DFB Laser with Narrow Linewidth and Higher Power", *IEEE Photonics Technology Letters*, 1, 1 (January 1989), p 6; H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf).

FIG. 10b shows a diagram of the TLS output power $P_T(\lambda, I_B)$ function of the bias current $I_B(t)$ that may be applied in embodiments of the present invention (see: M. Fukuda, M. Nakao, K. Sato, Y. Kondo, "1.55 mm Tunable DFB Laser with Narrow Linewidth and Higher Power", *IEEE Photonics Technology Letters*, 1, 1 (January 1989), p 6; H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf).

FIG. 10c shows a diagram of the TLD output wavelength that may be applied in embodiments of the present invention when sweeping the bias current $I_B(t)$ (see: M. Fukuda, M. Nakao, K. Sato, Y. Kondo, "1.55 mm Tunable DFB Laser with Narrow Linewidth and Higher Power", *IEEE Photonics Technology Letters*, 1, 1 (January 1989), p 6; H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf).

FIG. 10d shows a diagram of the cell transmittance with dip $T_C(\lambda)$ 1001 detailed on dip region 904 that may be applied in embodiments of the present invention. (The diagram is not to scale.)

Figure 10E:
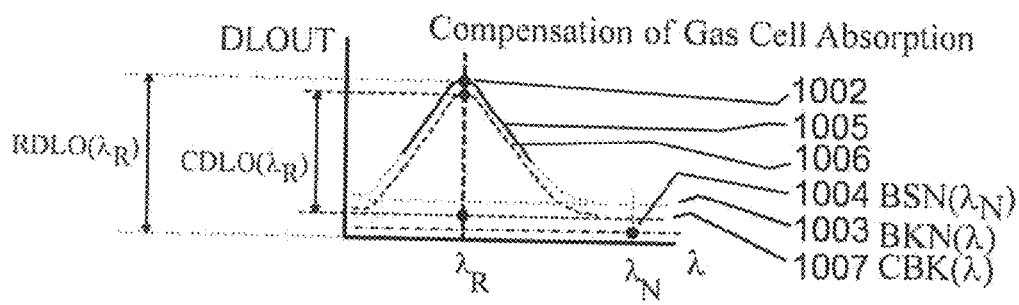
FIG. 10e is a graph of $RDLO(\lambda_R)$, $CDLO(\lambda_R)$ at resonant absorption wavelength of the analyte in accordance with an embodiment of the present invention.

FIG. 10e shows diagrams of the RDLO($\lambda_R$), CDLO($\lambda_R$) at resonant absorption wavelength of the analyte $\lambda_R$, compensated background CBK(λ), background noise BKN(λ) and BSN($\lambda_N$). As shown in FIG. 10e, RDLO($\lambda_R$) (as indicated by reference number 1005) at the output of the DLOG amplifier is represented, CDLO($\lambda_R$) (as indicated by reference number 1006) after subtracting the noise NDLO($\lambda_N$) is represented, and CBK(λ) (as indicated by reference number 1007) as the residual noise still remaining after subtracting NDLO($\lambda_N$) is represented.

The density of analyte mols $N_W$ is (see: M. Fukuda, M. Nakao, K. Sato, Y. Kondo, "1.55 mm Tunable DFB Laser with Narrow Linewidth and Higher Power", *IEEE Photonics Technology Letters*, 1, 1 (January 1989), p 6; H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf):

$$N_W = \frac{-1}{\sigma(\lambda_R) \cdot L_l} \cdot \ln\left[\frac{P_2(\lambda_R, I_{BR})}{P_1(\lambda_R, I_{BR})}\right] \quad (2)$$

where $P_1(\lambda_R, I_{BR})$ is the input optical power in the gas cell 201 at resonance wavelength $\lambda_R$, $P_2(\lambda_R, I_{BR})$ is the optical output power from the gas cell 201 at resonance wavelength $\lambda_R$ incident on the photodiode 258 and $\sigma(\lambda_R)$ is the absorption cross-section of the analyte at $\lambda_R$, expressed as is in accordance with equations in H. Hirayama, "Lecture Note on Photon Interactions and Cross Sections", *International Conference on Radiation Physics, Particle Transport Simulation and Applications*, Lisbon, Portugal, 23-26 Oct. 2000 http://rcwww.kek.jp/research/shield/photon_r.pdf:

$$\sigma(\lambda_R) = \frac{M_W}{N_A} \cdot \mu_C(\lambda_R) \quad (3)$$

where $M_W$ is the molecular weight of the analyte (which is water in one embodiment of this invention), $N_A = 6.022 \cdot 10^{23}$ is Avogadro's number, $\mu_C(\lambda_R) = \mu(\lambda_R)/\rho$ [cm²/g] is the mass attenuation coefficient at $\lambda_R$ which is in accordance with equations from Mass Attenuation Coefficient https://en.wikipedia.org/wiki/Mass_attenuation_coefficient, and ρ is analyte mass density.

In the embodiment shown in FIG. 3i, the output of the tunable laser TLS($\lambda, I_B$) (as indicated by reference number 238), and of the reference laser REFL($\lambda_N$) 247, are merged by the coupler CPL1, 244, into the same optical fiber 246, carrying the power denoted $P_L(\lambda, I_B)$. For both the tunable and reference lasers, $\lambda$ is the wavelength and $I_B$ is the bias current. In one embodiment of this invention, only one laser is active at a time; therefore $P_L(\lambda, I_B)$ can come either from the tunable laser 238, or from the reference laser 247. In the equations herein below, it will be used only $P_L(\lambda, I_B)$, which however, will not contribute to absorption in the gas cell. This is correct from the physical standpoint, because all optical elements work in linear range for laser beam power below 10 mW, in embodiments of the present invention.

In embodiments of the present invention, as shown in FIG. 3i, the optical power at the input of the gas cell $P_1(\lambda_R, I_{BR})$ is derived from the fiber 275 connected at the output of the fiber optic splitter 245. The optical power from TLS1 is available as $P_L(\lambda_R, I_{BR})$ in optical fiber 246 at the input of the splitter 245. The optical power $P_1(\lambda_R, I_{BR})$ at the input in the gas cell is:

$$P_1(\lambda, I_B) = S_C \cdot P_L(\lambda, I_B) \qquad (4)$$

In one embodiment of the present invention, the split coefficient $S_C = 0.99$.

The power in the optical fiber 257 pigtailed with the output collimator 215, $P_2(\lambda_R, I_{BR})$:

$$P_2(\lambda, I_B) = T_C(\lambda) \cdot S_C \cdot P_L(\lambda, I_B) \qquad (5)$$

where $T_C(\lambda)$ is the transmittance of the gas cell.

By combining the equations (2), (3), (4) and (5) the density of the analyte mols contained inside the gas cell can be expressed by;

$$N_W = \frac{-1}{\sigma(\lambda_R) \cdot L_l} \cdot \ln[T_C(\lambda_R)] \qquad (6)$$

where $\lambda_R$ is the wavelength of the tunable laser at the absorption peak of the analyte. If the analyte is water, the absorption peak can be at $\lambda_R = 1847.104$ nm. The equation (6), that may be valid at any wavelength $\lambda$, is independent of the laser beam power.

In embodiments of the present invention, equation (6) also incorporates the broadband optical losses of optical elements, for example, such as the optical elements shown in FIG. 3i, such as the optical splitter 245, the input collimator 210, the gas cell windows 202 and 202a, the reflective layers 208 and 209, the output fiber collimator 215, and the noise of the gases in the gas cell at any wavelength $\lambda$ into a spectral region containing $\lambda_R$, named further background noise $BKN(\lambda)$ (indicated as reference number 1003).

For eliminating the influence of the optical power in measuring the transmission through the gas cell 201 at any wavelength $\lambda$, including at the resonant wavelength $\lambda_R$ of the analyte, a reference beam is utilized that has power $P_0(\lambda, I_B)$ derived from $P_L(\lambda, I_B)$ by the beam splitter 245 through the optical fiber 252. The reference beam that is utilized is that beam at a point that is prior to the beam entering into the gas cell 201. At any wavelength $\lambda$, the power $P_0(\lambda, I_B)$ (indicated as reference number 252, as shown in FIG. 2a) that is directed toward the reference photodiode $PD_0$ denoted 274 is:

$$P_0(\lambda, I_B) = (1 - S_C) \cdot P_L(\lambda, I_B) \qquad (7)$$

Assuming that the photodiode has constant responsivity $R_D$ in the spectral range of the tunable laser 238 and of the reference laser 247, the photocurrent $PI_0(I_B)$ (indicated as reference number 253) that is generated by the photodiode 274 relies only on the bias current $I_B$:

$$PI_0(\lambda, I_B) = R_D \cdot (1 - S_C) \cdot P_L(\lambda, I_B) \qquad (8)$$

In one embodiment of the present invention, the logarithmic amplifier $LOG_0$ (indicated as reference number 254) converts the input current $PI_0(\lambda, I_B)$ to the output voltage $UL_0$ (indicated as reference number 255):

$$UL_0 = C_L \cdot \log [R_D \cdot (1 - S_C) \cdot P_L(\lambda, I_B)] \qquad (9)$$

The output voltage is directed to the non-inverting input of the DLOG differential amplifier (indicated as reference number 256). $C_L$ is a current-to-voltage conversion constant of the logarithmic amplifier, which is a constant of the logarithmic amplifier.

The photocurrent $PI_2(I_B)$ (indicated as reference number 259) generated by the output photodiode 258 as coupled with the gas cell output is:

$$PI_2(\lambda, I_B) = R_D \cdot S_C \cdot T_C(\lambda) \cdot P_L(\lambda, I_B) \qquad (9)$$

In one embodiment of the present invention, the logarithmic amplifier $LOG_2$ (indicated as reference number as 260) converts the input current $PI_2(\lambda, I_B)$ to the output voltage $UL_2$ (indicated as reference number 261):

$$UL_2 = C_L \cdot \log [R_D \cdot S_C \cdot T_C(\lambda) \cdot P_L(\lambda, I_B)] \qquad (10)$$

The output 268 of the DLOG is the difference $UL_2 - UL_0$ given by:

$$RDLO(\lambda) = -C_L \cdot \log \left[ \frac{1 - S_C}{S_C} \cdot T_C(\lambda) \right] \qquad (11)$$

$C_L$ is a constant, for example, such as may be specified by the manufacturer of the logarithmic amplifier.

At the resonant wavelength $\lambda_R$, the gas cell transmission reaches its minimum value $T_C(\lambda_R)$ (as indicated by reference number 1001 in FIG. 10d), which can span up to six decades or more. The connection of the LOG 0 output at the inverting input of DLOG and of LOG 2 output at the non-inverting input of DLOG consistently generates a peak $RDLO(\lambda_R)$ at the resonance absorption $T_C(\lambda_R)$:

$$RDLO(\lambda_R) = -C_L \cdot \log \left[ \frac{1 - S_C}{S_C} \cdot T_C(\lambda_R) \right] \qquad (12)$$

In one embodiment of the present invention, the logarithmic amplifier may be LOG 114 amplifier manufactured by Texas Instruments Inc. (see: LOG 114, "Single Supply, High Speed, Precision Logarithmic Amplifier", *Texas Instruments Inc.*, http://www.ti.com/lit/ds/sbos301a/sbos301a.pdf), with $C_L = 0.37$.

The density of mols $N_W$ inside the gas cell at $\lambda_R$ can be computed using $T_C(\lambda_R)$ derived from $RDLO(\lambda_R)$ value measured with high accuracy (for example, such as 16-bits or more) by the controller 290:

$$T_C(\lambda_R) = \frac{S_C}{1 - S_C} \cdot 10^{-\frac{RDLO(\lambda_R)}{C_L}} \qquad (13)$$

In the equation (13), $C_L$ value is guaranteed by the manufacturer of the logarithmic amplifier. $S_C$ may be specific for each individual coupler 245, but can be found from the equation (14), measuring $RDLO(\lambda_N)$ when the tunable laser 238 is turned off and the reference laser 247 is turned on. In this case, the transmittance $T_C(\lambda_N) = 1$ with negligible error.

$$S_C = \left[1 + 10^{-\frac{RDLO(\lambda_R)}{C_L}}\right]^{-1} \quad (14)$$

$S_C$ computed with the equation (14) by the controller 290 is stored into a non-volatile memory for further use for computing the raw mass of the analyte $rm_W$ at $\lambda_R$ using the equation (15) herein. The storage by the controller and computing by the controller may occur during the normal operation of embodiments of the apparatus of the present invention.

From the equations (4) through (12), the raw mass of the analyte $rm_W$ measured at $\lambda_R$ inside the gas cell 201 with volume $V_C$ is:

$$rm_W = K \cdot \left[\frac{RDLO(\lambda_R)}{C_L} \cdot \ln(10) - \ln\left(\frac{S_C}{1-S_C}\right)\right] \quad (15)$$

Where K is a calibration constant of the apparatus:

$$K = \frac{M_W}{N_A} \cdot \frac{V_C}{\sigma(\lambda_R) \cdot L_I} \quad (16)$$

defined during the calibration of the apparatus built according to this invention.

The partial pressure $p_W$ of the analyte inside the gas cell can be computed using the general equation of gases and the raw mass of the analyte $rm_W$:

$$p_W = \frac{rm_W}{M_W} \cdot \frac{T_{MX}}{V_C} \cdot R \quad (17)$$

Where $T_{MX}$ is the temperature of the gas mixture inside the gas cell measured with the temperature sensor 235 and R=8.314462 J/(mol·K) is the gas constant (in accordance with the gas constant, as provided at https://en.wikipedia.org/wiki/Gas_constant).

Figure 11:
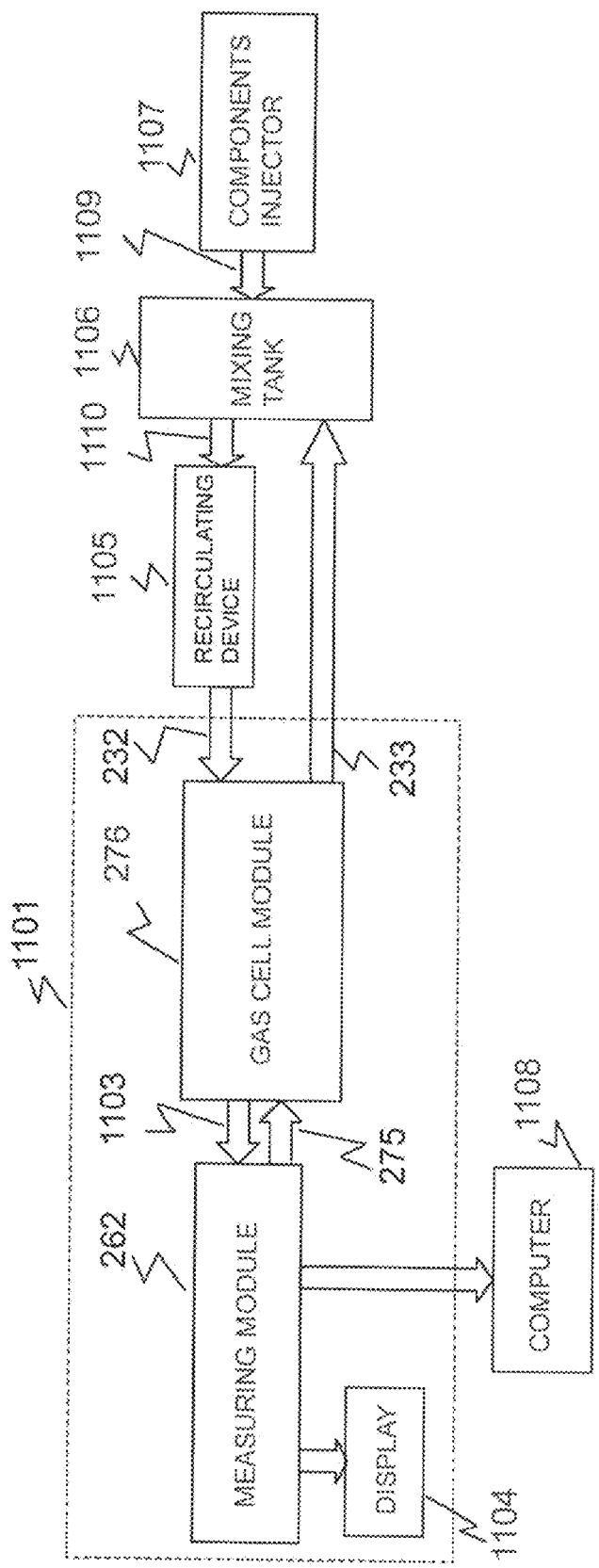
FIG. 11 is a schematic drawing of an embodiment of the calibration configuration of an apparatus of the present invention.

An example of a calibration of the apparatus is shown in FIG. 11. The apparatus to be calibrated consists of the gas cell module 276 and the measuring module 262. A connection 1103 between the gas cell module and the measuring module is formed by the optical fiber 275 and the elements as follows: optical fiber 257, signal TIN 269, and signal PIN 270. The measuring module is attached to a display 1104 and a computer 1108. The computer may be any computing device, for example, such as a laptop computer, a desktop computer, a tablet, a smart phone, or any other computer device. In embodiments of the present invention the display may be integrated with the computer. The attachment or other connection between the measuring module and the computer and the measuring module and the display may be a wired or wireless connection.

The intake port 232 of the gas cell module 276 is connected to a gas re-circulating device 1105. The gas re-circulating device further connected to a mixing tank 1106. The mixing tank is connected to a components injector 1107. The exhaust port 233 of the gas cell module is connected to the mixing tank 1106. The re-circulating device 1105 runs continuously when the apparatus of the present invention is in use, as the re-circulating device is operable to facilitate flow of gas from the mixing tank 1106 through the gas cell module.

A user of the apparatus may inject or otherwise supply an analyte concentration into the mixing tank 1106. For example, the user may utilize a components injector 1107 to inject the analyte concentration into the mixing tank. The measuring module 262 continuously determines the peak absorption of the analyte, in accordance with the methods disclosed herein. The measuring module further determines the raw mass of the analyte $rm_W$ in the gas cell, in accordance with equation (15). The measuring module is also operable to continuously provide the results of its determinations to be displayed to a user on the display 1104, and to the memory, storage or another element of the computer 1108.

To each analyte concentration inputted by the operator into the mixing tank 1106, there corresponds a raw mass of the analyte $rm_W$ in the gas cell 276. The calibration procedure generates a data stream for RDLO and another data stream for $rm_W$. The controller is operable to generate a graph, such as in the same format as the graph 1111 as shown in FIG. 11*b*. The controller is further operable to store the generated graph and other data relating to the equations and the operations of the apparatus, and that is collected by the sensors and other elements of the present invention as described herein, in the memory of the controller 290. All stored data is accessible by the controller to be utilized by the controller or to be relayed or otherwise provided by the controller to a user. As shown in FIG. 11*b*, the graph may represent a linear function, and each measured $RDLO_x$ may correspond to only one value $rm_{W_x}$.

$rm_W$ reported at each reading can be utilized by the present invention in several manners, for example, such as:

(i) utilized directly for monitoring the mass of the analyte inside the gas cell; and/or (ii) utilized to compute the partial pressure PA of the analyte inside the gas cell The calibration of the present invention may be performed at an initial point in time and a particular location, for example, such as before the first use of the apparatus and method and in an environment such as a factory. The calibration may be repeated periodically at intervals, for example, such as three to five year intervals during the life of the apparatus. The calibration results and output will be stored in the controller memory, for example, such as non-volatile memory. The stored data will include at least analyte mass $rm_W$ at each $RDLO(\lambda_R)$ reading.

The gas cell transmission is independent of the optical power injected into the optical fiber 246 in accordance with the requirements for the differential swept wavelength absorption spectroscopy ("DSWAS") method that at least measures the beam power in logarithmic scale. When the beam power is measured on a linear scale the measurement is ratiometric. The optical power of all lasers remains small enough so as not to produce non-linear effects on the optical path. A skilled reader will recognize that there are other scales whereby the beam power may be measured.

$RDLO(\lambda_R)$ may also contain the background noise BKN ($\lambda$) (as indicated by reference number 1003 in FIG. 10*e*). The gas cell volume $V_C$ and gas cell length $L_C$ are measurable entities. The Avogadro number $N_A$ and the molecular weight of the water as analyte $M_W$ may for example be derived from the tables of physical constants.

As shown in FIG. 9*b*, a graph generated by the present invention may indicate water absorption $T_{H2O}(\lambda_R)$=211.87 dB (as indicated by reference number 1002) and the methane absorption $T_{CH4}(\lambda_R)$=−0.16 dB (as indicated by reference number 906) at $\lambda_R$=1854.104 nm. These values are provided in accordance with use of the present invention in the conditions specified in FIG. 9b. A skilled reader will recognize that these values may vary in accordance with other uses of the present invention made in other conditions than those relating to the values shown in FIG. 9b.

$T_{CH4}(\lambda_R)$ is the methane contribution of the background noise BKN($\lambda$) (as indicated as reference number 1003 in FIG. 10*e*). The negative sign of $T_{CH4}(\lambda_R)$ was discarded because of the phase change introduced by DLOG amplifier 256. The methane absorption at $\lambda_R$ is generated by various mechanisms such as elastic collisions between molecules and other mechanisms as will be recognized by those skilled in the art. For high concentrations of the analyte (such as is shown in FIG. 9*b*), methane absorption $T_{CH4}(\lambda_R)=0.16$ dB in the background noise BKN($\lambda$) does not have significant impact on analyte measuring accuracy. For very low analyte concentrations in parts-per-billion (ppb) range and below, the 0.16 dB value remains constant and can be an important contribution of noise. BKN($\lambda$) can drastically reduce analyte detection capability at very low concentrations. The raw analyte mass $rm_W$ computed in accordance with equation (15) from RDLO($\lambda_R$) includes background noise BKN($\lambda_R$) which is the contribution of all of the gas mixture noise, the optical layout noise and the photo detection noise, being bias noise BSN($\lambda_R$) (as indicated by reference number 1004 in FIG. 10*e*). The bias noise must be subtracted from RDLO ($\lambda_R$) to increase the sensitivity of analyte detection of the present invention.

At least one reference laser REFL1 may be operable to emit a single wavelength $\lambda_N$ in the spectral region where there is extremely low absorption in an analyte, for example, such as a water analyte, and also extremely low absorption in the most dominant component of the gas mixture, for example, such as methane. As shown in FIG. 9*c*, the transmittance of both water and methane in 1550 nm region using data from reference HITRAN on the Web http://hitran.iao.ru/molecule/bands/mol/1, may result in values, such as the following: at $\lambda_N=1550.12$ nm, which belongs to the ITU grid for optical communications, water transmittance is $T_{H2O}(\lambda_N)=0.00251$ dB, and methane transmittance $T_{CH4}(\lambda_N)=0.000107$ dB. Both water transmittance and methane transmittance are much lower than the methane residual transmission at the resonant absorption in water $T_{CH4}(\lambda_R)=0.16$ dB (as shown in FIG. 9*b*). In one embodiment of the present invention, NLDO($\lambda_N$) is the output 268 of the DLOG amplifier 256, when only REFL1 is active, generating $\lambda_N$ for measuring the residual loss of the optical path. The compensated absorption of the analyte CLDO($\lambda_R$), is the difference:

$$CLDO(\lambda_R) = RLDO(\lambda_R) - NLDO(\lambda_N) \quad (18)$$

which subtracts the baseline noise BLN($\lambda_N$) from the raw absorption at $\lambda_R$.

DSWAS applies these calculations and steps discussed herein for the purpose of removing the residual loss of the optical system from the analyte raw absorption measurement, and determining the result of this removal.

Within the power ranges below 10 mW the absorption measurement in the gas cell is independent on the optical power of the laser at any wavelength, including within the tuning range of TLS and at any reference wavelength $\lambda_N$.

One or more reference wavelengths $\lambda_N$ are utilized in the present invention. Such reference wavelengths are generated by activating the reference laser REFL1 247. Laser REFL1 will be activated when all the other lasers, such as TLS1 238, TLS2 239, and REFL2 248, are inactive. When the controller activates laser REFL1 it disables the other lasers. As shown in FIG. 2, the output 291 of REFL1 247 passes through the beam combiners 249 and 244 before entering into the optical fiber 246, as does the TLS1 beam. When REFL1 is active, $P_L(\lambda, I_B)$ is the optical power directed from REFL1. From the point from which the REFL1 is directed it follows an identical optical path through all optical components, the gas cell 201, and up to the photodiodes 258 and 274, as the optical path described herein as the path of an active TLS1 238. All equations from (1) through (16) are applicable to the use of REFL1.

Differences between the operation of REFL1 and the operation of TLS1 (as described herein) include the following: (1) there is no wavelength sweep when REFL1 is in operation; (2) the resonance wavelength $\lambda_R$ must be replaced with $\lambda_N$ when REFL1 is in operation; (3) there is no peak detection, just analog to digital conversion of the output of DLOG amplifier 256 for finding NLDO($\lambda_N$) used further for calculating the noise compensated value CDLO($\lambda_R$) as shown in the equation (16) when REFL1 is in operation.

The compensated mass of the analyte is expressed by:

$$cm_W = K \cdot \left[ \frac{CDLO(\lambda_R)}{C_L} \cdot \ln(10) + \log\left(\frac{S_C}{1 - S_C}\right) \right] \quad (19)$$

where the calibration constant K is defined by the equation (16).

The compensated mass of the analyte $cm_A$ independent of its concentration and of the other gases of the gas mixture is determined through the utilization of Equation (19) by the controller.

A skilled reader will recognize the applicability of equation (19) for the purpose of determining the volume concentration of an analyte, for example, such as a water analyte, within a gas mixture, for example, such as natural gas mixture, contained in the gas cell with $V_C$ volume at gas mixture temperature $T_{MX}$ measured with the temperature sensor 235 and at the total pressure of gas mixture $p_{MX}$ measured with the pressure sensor 236.

In one embodiment of the present invention, a single unit for monitoring multiple analytes such as methane ($CH_4$), water ($H_2O$), carbon dioxide ($CO_2$), hydrogen sulfide ($H_2S$) and eventually other analytes is utilized. The tunable laser must cover a broad range of 40 nm or more, such as is described in Miron N., "Tunable laser with tilted-mirrors interferometer and dynamic wavelength reference", *Proc. of SPIE*, 7195, 71952J-1-71952J-12, (2009), or an equivalent range. The tunable laser may be broadly tunable. The tunable laser that is broadly tunable may be TLS2 239 in embodiments of the present invention. The use of the broadly tunable laser is applied in an identical manner, or a virtually identical manner, to utilizations of the present invention to determine multiple analytes and to determine a single analyte. To avoid an ambiguous result, in the present invention a single spectral absorption line is used for each analyte, and the spectral absorption line must be unique among all absorption lines of the gas mixture.

The controller 290 sends a tuning signal $U_{T2}$ to TLS2 to activate TLS2 to sweep the wavelength. If required, an additional reference laser REFL2 248 can be used for measuring more than one background noise BLN($\lambda_{N2}$). The optical fibers 241 are operable to direct TLS2 output to the optical path described herein upon the activation and operation of TLS1. Also, the controller 290 may generate the control signal $U_{T2}$ 265 that is operable to tune TLS2 and the controller may generate a bias current $I_{RL2}$ that is operable to activate the reference laser REFL2. The equation (15) is utilized by the controller to determine the mass of each analyte.

The controller 290 of the measuring module 262 is operable to generate the signals $I_{B1}$ 263 and $U_{TEC1}$ 264 and such signals are operable to control the tunable laser TLS1 238. The controller is operable to generate a control signal $U_{T2}$ 265 that is operable to control the tunable laser TLS2 239. The controller is operable to generate the bias current $I_{RL1}$ 266 that is operable to control the reference laser REFL1 247. The controller is operable to generate the bias current $I_{RL2}$ 267 that is operable to control reference laser REFL2 248. The controller is operable to receive the signal DLIN 268 from the referenced signal differential amplifier DLOG 256. The controller is operable to receive the signal TIN 269 from the temperature sensor 235 proportional with the temperature of the analyte. The controller is operable to receive the signal PIN 270 from the pressure sensor 236 proportional with the total pressure $p_{MX}$ in the gas cell 201. The controller 290 may be operable to determine the concentration of the analyte in the gas mixture flowing through the gas cell 201 and may utilize the compensated mass $cm_W$ of the analyte, the gas cell volume $V_C$, the gas mixture temperature $T_{MX}$ and the gas mixture pressure $p_{MX}$ to produce such a determination.

The controller 290 is operable to communicate with a host 271 through the serial communication 272 and to send to the host the analog voltage 273.

Figure 12:
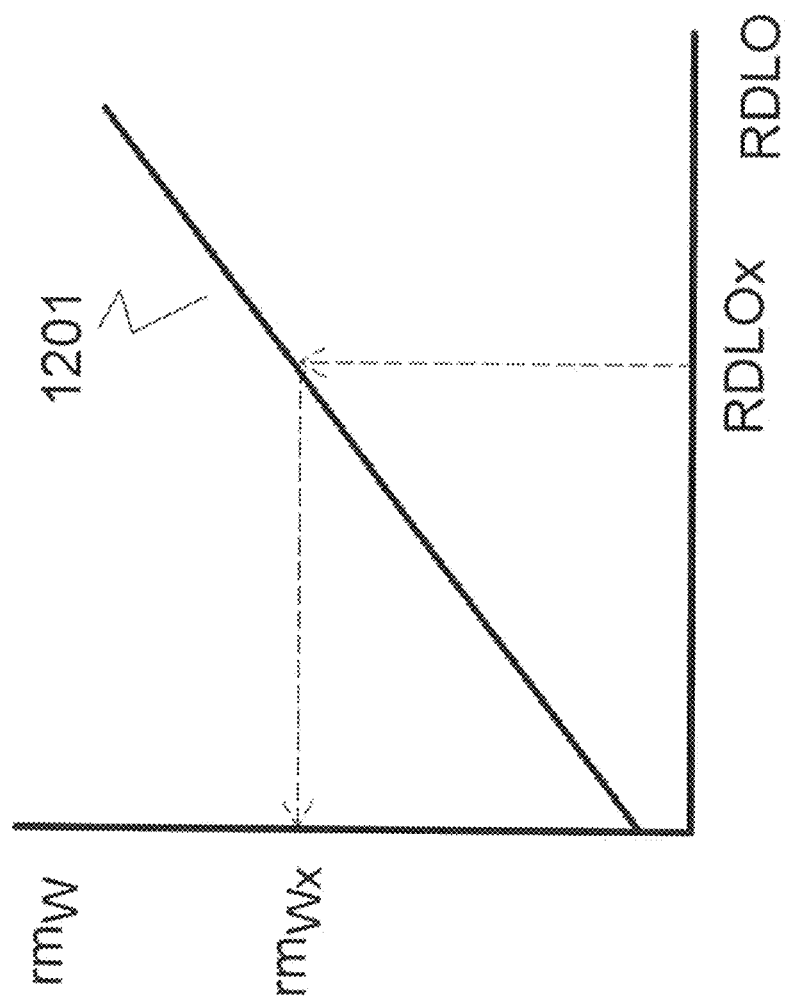
FIG. 12 is graph showing an example of calibration results.

As shown in FIG. 12, the calibration may be depicted in a graph format 1201.

In the drawings the measuring module and the gas cell module are shown having a gap in between. Some embodiments of the present invention may incorporate a gap of varying sizes between the measuring module and the gas cell module. The measuring module and the gas cell module may be located distantly from each other in some embodiments of the present invention. In other embodiments of the present invention the measuring module and the gas cell module may be attached, be proximate to each other so as to not have any gap therebetween, or be housed together in a single housing. Both modules must be incorporated in embodiments of the present invention for the embodiments to function as discussed herein.

The gas cell module incorporates a laser beam and an analyte, the laser beam being operable to interact with the analyte at a wavelength whereby a resonant absorption of the analyte occurs that can be utilized for measuring the analyte concentration. The laser beam being further operable at a wavelength whereby there is very low absorption in the gas cell, and can be utilized for measuring the background noise introduced by noise and by the photo detection channels in the manner described herein.

The gas cell module further incorporates temperature and pressure sensors operable to each provide a signal to the measuring module that is utilized by the measuring module in the manner discussed herein.

The measuring module incorporate components that function to operate elements of the gas cell module, as described herein. The measuring module further incorporate components that are operable to receive data and signals produced by components of the gas cell module. The data and signals received by the measuring module are utilized by the components of the measuring module to undertake determinations and produce output for the user, including text, graphics, reports, and other output.

The measuring module operates the laser beam so that the swept wavelength laser beam is provided to the gas cell module in an appropriate spectral range for the operation of the present invention. The measuring module is operable to detects the absorption peak, determine the raw mass of the analyte, measure the combined background noise of the optics and of the photo detection channels, determine the compensated mass of the analyte, display locally the analyte concentration on a display that is either integrated in the controller or that is connected to the controller by a wired or wireless connection. The measuring module is further operable to send the data or other information pertaining to the concentration of the analyte to a remote host, through a wired or wireless communication means. The data or other information pertaining to the concentration of the analyte may be further processed by the remote host. In some embodiments of the present invention the measuring module may be connected to or integrate storage, wherein data and other information collected and generated by the present invention may be stored. The measuring module may further provide data and other information to remote storage means, for example, such as to the remote host that may be operable to store such data and information. The remote host may utilize the data and information in any manner, and may generate analog signals proportional with the analyte concentration. The remote host may communicate such analog signals to the measuring module.

It will be appreciated by those skilled in the art that other variations of the embodiments described herein may also be practiced without departing from the scope of the invention. It should be apparent to those skilled in the art that the foregoing is illustrative only and not limiting, having been presented by way of example only. All the features disclosed in this specification (including any accompanying claims, abstract and drawings) may be replaced by alternative features serving the same purpose, equivalent or similar purpose, unless expressly stated otherwise. Therefore, numerous other embodiments of the modifications thereof are contemplated as falling within the scope of the present invention as defined by the appended claims and equivalents thereto.

What is claimed is:

1. An apparatus operable to measure the content of one or more gas analytes within a gas mixture, said apparatus comprising:
   a. a measuring module, comprising:
      i. a controller operable to activate a laser beam generator to generate a laser beam;
      ii. a processor operable to determine the content of the one or more gas analytes within the gas mixture based upon information collected from one or more sensors;
      iii. a DLOG differential amplifier connected at its non-inverting input to the reference logarithmic amplifier, and connected at is inverting input to the signal logarithmic amplifier, said DLOG differential amplifier being operable to generate a referenced absorption signal proportional to the difference between reference voltage at output from reference logarithmic amplifier and signal voltage at output of the signal logarithmic amplifier; and
      iv. the controller being operable to: receive analog signals from the DLOG differential amplifier, and at least one of the one or more sensors; convert analog input voltages to digital output; generate control signals for the one or more tunable lasers and for the one or more reference lasers; communicate with a host processor; and perform determinations; and b. a gas cell module connected to the measuring whereby information and commands are transferable between the measuring module and the gas cell module, said gas cell module comprising:

iii. a closed gas cell containing the gas mixture and the one or more analytes, said closed gas cell having two transparent windows therein on opposite sides of the closed gas cell;

iv. two mirrors having reflective surfaces facing each other positioned on opposite sides of the closed gas cell and each being positioned proximate to one of the transparent windows;

v. the laser beam generator operable to generate or direct a laser beam, said laser beam generator being positioned in proximity to one of the two mirrors, when generated the laser beam being directed towards the mirror on the side of the closed gas cell opposite the laser beam generator, the laser beam being directed so is reflected one or more times between the two mirrors, and in each reflection it passes through all of following: the window in the closed gas cell closest to the laser beam generator; the gas mixture inside the closed gas cell; and the other window in the closed gas cell, the laser beam generator further being operable to send laser beam input power information to the measuring module; and vi. a laser beam output operable to receive the laser beam after it has been reflected and send laser beam output power information to the measuring module;

vii. the one more sensors being operable to sense and transfer information pertaining to the laser beam, the gas mixture, and the one or more analytes interaction with the laser beam; and wherein the measuring module utilizes the input laser power information and the output laser beam power information to determine the absorption of the one or more analytes.

2. The apparatus of claim 1, wherein the gas cell module further comprises:

a. the laser beam generator being an input collimator;

b. a low loss input optical port positioned as integrated in the mirror proximate to the input collimator;

c. the laser beam output being a low loss optical output port positioned as integrated in the mirror opposite the mirror wherein the low loss input optical port is integrated;

d. the laser beam being a collimated input optical beam that is directed through the low loss input optical port at an incidence angle that is in relation to a gas cell axis of the gas cell so that the one or more reflections of the input optical beam between the mirrors gradually direct the collimated input optical beam towards the low loss optical output port;

e. an output collimator operable to collect the optical beam passing through the low loss output optical port; and f. the one or more sensors including the following: a temperature transducer operable to emit a signal proportional to a temperature of at least one of one or more the analytes; and a pressure transducer operable to emit a signal proportional to the pressure of at least one of one or more the analytes.

3. The apparatus of claim 1, wherein the gas cell module further comprises:

a. the laser beam generator being an input collimator;

b. a low loss input optical port and the laser beam output being a low loss optical output being positioned as integrated in the mirror proximate to the input collimator;

c. the laser beam being a collimated input optical beam that is directed through the low loss input optical port at an incidence angle that is in relation to a gas cell axis of the gas cell so that the one or more reflections of the input optical beam between the mirrors gradually direct the collimated input optical beam towards the low loss optical output port;

d. an output collimator operable to collect the optical beam passing through the low loss output optical port; and e. the one or more sensors including the following: a temperature transducer operable to emit a signal proportional to a temperature of at least one of one or more the analytes; and a pressure transducer operable to emit a signal proportional to the pressure of at least one of one or more the analytes.

4. The apparatus of claim 1, wherein the measuring module further comprises:

a. the processor receiving information from the gas cell module being operable to determine a single absorption line of the analyte that is unique among all the absorption lines of the gases contained in the gas cell;

b. one or more tunable lasers operable in a spectral interval broader than the absorption line width of the analyte to deliver one or more tunable laser beams through one of the following: a tunable laser single mode optical fiber, or a laser beam generator comprising bulk optic elements;

c. one or more reference lasers operable to generate a single line delivery of one or more reference beams through one of the following: a reference laser single mode optical fiber, or a laser beam generator comprising bulk optic elements;

d. a beam combiner operable to merge into a single laser source optical fiber, the one or more tunable laser beams and the one or more reference laser beams as a combined beam, said single laser source propagating through one of the following: the optical fibre, or bulk optical elements;

e. a beam splitter operable to receive the combined beam having a tap output through which a fraction of optical power of the combined beam is directed as a fraction beam and a main output through which the balance of the optical power of the combined beam is directed as an output beam, said output beam being directed to the gas cell;

f. a reference photodiode operable to receive the fraction beam;

g. a signal photodiode operable to receive the laser beam from output of the gas cell;

h. a reference logarithmic amplifier operable to convert to reference voltage a high dynamic range photocurrent generated by the reference photodiode;

i. a signal logarithmic amplifier operable to convert to signal voltage a high dynamic range photocurrent generated by the signal photodiode;

k. a real time clock; and l. a non-volatile memory operable to store data that is determinations and information generated by the apparatus.

5. The apparatus of claim 1, wherein the closed gas cell is formed of corrosion resistant material shaped in a tubular form and the windows are positioned at each end of the tubular form on an optical axis of the tubular form, said optical axis being collinear with a geometric axis of the tubular form, said tubular form incorporating a gas input port whereby the gas mixture enters the gas cell, and a gas output port operable as a gas exhaust for the gas mixture, and said closed gas cell being operable to prevent contact of the one or more analytes with optical elements of the apparatus, and said closed gas cell being positioned between the mirrors so as to be perpendicular to each mirror.

6. The apparatus of claim 1, wherein the mirrors are positioned to be parallel and each comprise a circular mirror substrate having a reflective flat surface coated with a low loss coating, and having an anti-reflective surface another surface coated with a low loss antireflective coating, the reflective surface of one mirror incorporating one or more transparent optical ports operable to direct input and output laser beams.

7. The apparatus of claim 1, wherein a display is connected to the measuring module, whereby output information generated by the measuring module is communicated to a user.

8. The apparatus of claim 1, wherein the measuring module is formed of bulk optical components.

9. An apparatus for measuring the content of one or more gas analytes within a gas mixture, said apparatus comprising:
  a. a measuring module, comprising:
    i. a controller operable to activate a laser beam generator to generate a laser beam;
    ii. a processor operable to determine the content of the one or more gas analytes within the gas mixture based upon information collected from one or more sensors;
    iii. a DLOG differential amplifier connected at its non-inverting input to the reference logarithmic amplifier, and connected at is inverting input to the signal logarithmic amplifier, said DLOG differential amplifier being operable to generate a referenced absorption signal proportional to the difference between reference voltage at output from reference logarithmic amplifier and signal voltage at output of the signal logarithmic amplifier; and
    iv. the controller being operable to: receive analog signals from the DLOG differential amplifier, and at least one of the one or more sensors; convert analog input voltages to digital output; generate control signals for the one or more tunable lasers and for the one or more reference lasers; communicate with a host processor; and perform determinations; and
  b. an open gas cell module comprising:
    v. an open gas cell wherein the gas mixture and the one or more analytes are present;
    vi. a reflecting target positioned on one side of the open gas cell;
    vii. the laser beam generator operable to generate or direct a laser beam, said laser beam generator being positioned opposite to the reflecting target having the one or more analytes between the laser beam generator and the reflecting target, the laser beam being directed from the laser beam generator towards the reflecting target and being reflected from the reflecting target, said laser beam generator being operable to send laser beam input power information to the measuring module; and
    viii. a telescope integrated with a transceiver, said telescope being operable to collect the laser beam reflected by the reflective target and to send laser beam output power information to the measuring module; and
  wherein the measuring module utilizes the input laser power information and the output laser beam power information to determine the absorption of the one or more analytes.

10. The apparatus of claim 9, wherein the open gas cell having at one end the transceiver that is an optical transceiver composed of an input collimator and an output collimator, the input and output collimators facing the reflective target that is a retro-reflector.

11. The apparatus of claim 9, wherein the open gas cell is defined as the space between the reflecting target and the transceiver and can contain any of the following: the one or more analytes; vapors of the one or more analytes; or plasma or liquid containing the one or more analytes.

12. The apparatus of claim 9, wherein the open gas cell module further incorporates one or more converting elements operable to convert the plasma or the liquid to a gas mixture.

13. A method for measuring the content of one or more gas analytes within a gas mixture and monitoring the mass of the one or more analytes, said method comprising the steps of:
  a. generating a laser beam from a laser beam generator and gathering the input power of the laser beam;
  b. directing the laser beam through a gas cell having a gas mixture containing the one or more analytes therein, the laser beam further being directed to a reflective surface, said reflective surface being operable to reflect the laser beam through the gas cell at least one more time;
  c. gathering the output power of the laser beam at the point when the laser beam passes from the gas cell for the last time, by way of at least the following steps:
    i. obtaining a maximum analog voltage at the output of a DLOG differential amplifier dependent on the transmittance of at least one of the one or more analytes at a resonance wavelength;
    ii. converting of a peak voltage at the output of the DLOG differential amplifier to a digital value with high resolution representing a non-compensated resonant peak absorption by at least one of the one or more analytes;
    iii. storing the non-compensated resonant peak absorption into a temporary peak register, said non-compensated resonant peak absorption containing a background noise;
  d. transferring the output power and input power to a measuring module;
  e. one more sensors generating sensor information related to the laser beam, the gas mixture, and the one or more analytes interaction with the laser beam, and the one or more sensors transferring such sensor information to the measuring module; and
  f. the measuring module utilizing the input power, the output beam and any of the sensor information to determine the absorption of the one or more analytes.

14. The method of claim 13, further comprising the steps of:
  a. sweeping a tunable laser beam wavelength from a minimum wavelength to a maximum wavelength in a spectral region containing the absorption line of the analyte, and sensing the non-compensated resonant peak absorption of the tunable laser beam upon completion of the sweeping, said non-compensated resonant peak absorption of the tunable laser beam being proportional to analyte absorption;

b. disabling the tunable laser and activating at least one reference laser, said at least one reference laser lasing in a spectral range wherein at least one of the one or more analytes are located, and further lasing in a spectral range wherein other gases of the gas mixture contained in the gas cell have negligible absorption, said reference laser beam utilizing the same optical path, the same photodiodes, logarithmic amplifiers, the DLOG differential amplifier and other components as the tunable laser beam; and c. converting the output of the DLOG differential amplifier to high resolution numerical value representing the background noise, and storing said high resolution numerical value in a temporary background noise register.

15. The method of claim 13, wherein the gas cell is a closed gas cell or an open gas cell.

16. The method of claim 13, further comprising the steps of the measuring module:

a. determining a compensated absorption utilizing at least one of the one or more analytes by subtracting background noise stored in a temporary background noise register from a peak absorption stored in the temporary peak register; and b. determining the mass of at least one of the one or more analytes contained in the gas cell utilizing a compensated absorption of the at least one of the one or more analytes, temperature and pressure of the at least one of the one or more analytes, volume of the gas cell, and constants of the one or more sensors as collected by the during a calibration process.

17. The method of claim 13, further comprising the steps of:

a. determining a peak absorption of at least one of the one or more analytes to a wavelength accuracy limited by a linewidth of the laser beam that is generated by a tunable laser in operation;

b. determining a wavelength and a peak absorption value of at least one of the one or more analytes independent of other gases in the gas cell and of total pressure of the gas mixture in the gas cell; and c. determining statistical information utilizing one or more true absorption values for increasing the sensitivity of the instrument.

18. The method of claim 13, further comprising the step of utilizing one absorption line of at least one of the one or more analytes that overlap partially with another absorption line of other gas components contained in the gas cell.

19. The method of claim 18, wherein any one or more of the following:

a. a laser source is utilized that matches a selected absorption line of at least one of the one or more analytes as the laser generator;

b. a laser generator is utilized that is one or more tunable lasers generators for generating multiple tunable laser wavelengths in different narrow spectral ranges;

c. the laser beam is multiple laser beams including laser beams that are tunable in a narrow tuning range and laser beams that are tunable in a broad tuning range;

d. the multiple laser beams covering a broad tuning range; and e. multiple reference laser are utilized for measuring background noise.

20. The method of claim 13, utilizing a measuring module comprising bulk optical elements, further comprising the steps of:

a. combining the laser beams that are tunable laser beams and a reference laser beam into a combined laser source beam, said tunable laser beams being generated by a tunable laser generator and said reference laser beam being generated by a reference laser generator;

b. transmitting a sample of the laser source beam to a reference photodiode and transmitting the laser source beam content other than the sample to an input collimator of the gas cell;

c. collimating the laser beam directed to the gas cell; and d. collecting the laser beam emerging from the gas cell and sending it to a signal photodiode.

\* \* \* \* \*